(12) United States Patent
Laurance

(10) Patent No.: US 10,229,245 B2
(45) Date of Patent: Mar. 12, 2019

(54) METHOD FOR BIOLOGICAL DATA ANALYSIS

(75) Inventor: Megan E. Laurance, San Francisco, CA (US)

(73) Assignee: QIAGEN Redwood City, Inc., Redwood City, CA (US)

(*) Notice: Subject to any disclaimer, the term of this patent is extended or adjusted under 35 U.S.C. 154(b) by 1106 days.

(21) Appl. No.: 14/236,056

(22) PCT Filed: Aug. 2, 2012

(86) PCT No.: PCT/US2012/049391
§ 371 (c)(1),
(2), (4) Date: Sep. 4, 2014

(87) PCT Pub. No.: WO2013/019987
PCT Pub. Date: Feb. 7, 2013

(65) Prior Publication Data
US 2014/0372953 A1    Dec. 18, 2014

Related U.S. Application Data

(60) Provisional application No. 61/574,539, filed on Aug. 3, 2011.

(51) Int. Cl.
| *G06F 3/048* | (2013.01) |
| *G06F 19/26* | (2011.01) |
| *G06F 19/28* | (2011.01) |
| *G06F 3/0481* | (2013.01) |
| *G06F 3/0484* | (2013.01) |

(52) U.S. Cl.
CPC .......... *G06F 19/26* (2013.01); *G06F 3/04817* (2013.01); *G06F 3/04842* (2013.01); *G06F 19/28* (2013.01)

(58) Field of Classification Search
None
See application file for complete search history.

(56) References Cited

U.S. PATENT DOCUMENTS

| 2003/0177112 A1* | 9/2003 | Gardner ................ G06F 19/28 |
| 2003/0220820 A1* | 11/2003 | Sears ................ G06Q 50/24 705/3 |
| 2004/0002818 A1* | 1/2004 | Kulp ................ G01N 33/68 702/20 |
| 2004/0061702 A1 | 4/2004 | Kincaid |
| 2004/0126840 A1 | 7/2004 | Cheng et al. |
| 2004/0241730 A1 | 12/2004 | Yakhini et al. |
| 2005/0216459 A1* | 9/2005 | Vailaya ................ G06F 19/28 |
| 2006/0036368 A1 | 2/2006 | Chen et al. |
| 2006/0036425 A1 | 2/2006 | Le Cocq et al. |
| 2007/0198653 A1 | 8/2007 | Jarnagin et al. |
| 2010/0185984 A1 | 7/2010 | Wright et al. |

OTHER PUBLICATIONS

Cline, M.S. et al., "Integration of biological networks and gene expression data using Cytoscape," *Nature Protocols*, vol. 2, No. 10, pp. 2366-2382 (Oct. 1, 2007).

(Continued)

*Primary Examiner* — William C Trapanese
(74) *Attorney, Agent, or Firm* — Sterne, Kessler, Goldstein & Fox P.L.L.C.

(57) ABSTRACT

The invention provides computer systems and methods for visualization and analysis of relationships between biological data.

2 Claims, 40 Drawing Sheets

(56) References Cited

OTHER PUBLICATIONS

Gietzen, D. et al., "Ingenuity Pathways Analysis (IPA) of Large Datasets," retrieved from http://www.usc.edu/hsc/nml/assets/bioinfo/IPA/Data_Analsyis_TrainingHandouts.pdf, Ingenuity Systems, 19 pages (Copyright 2010).
Lex, A. et al., "Caleydo: Design and Evaluation of a Visual Analysis Framework for Gene Expression Data in its Biological Context," *IEEE Pacific Visualization Symposium*, pp. 57-63 (Mar. 2, 2010).
Supplementary Partial European Search Report, for European Patent Appl. No. 12820124.1, dated Jan. 29, 2015, 6 pages.
Supplementary European Search Report, for European Patent Appl. No. 12820124.1, dated May 26, 2015, 15 pages.
International Search Report based on PCT/US2012/049391 dated Oct. 22, 2012.

\* cited by examiner

FIG. 5(C)

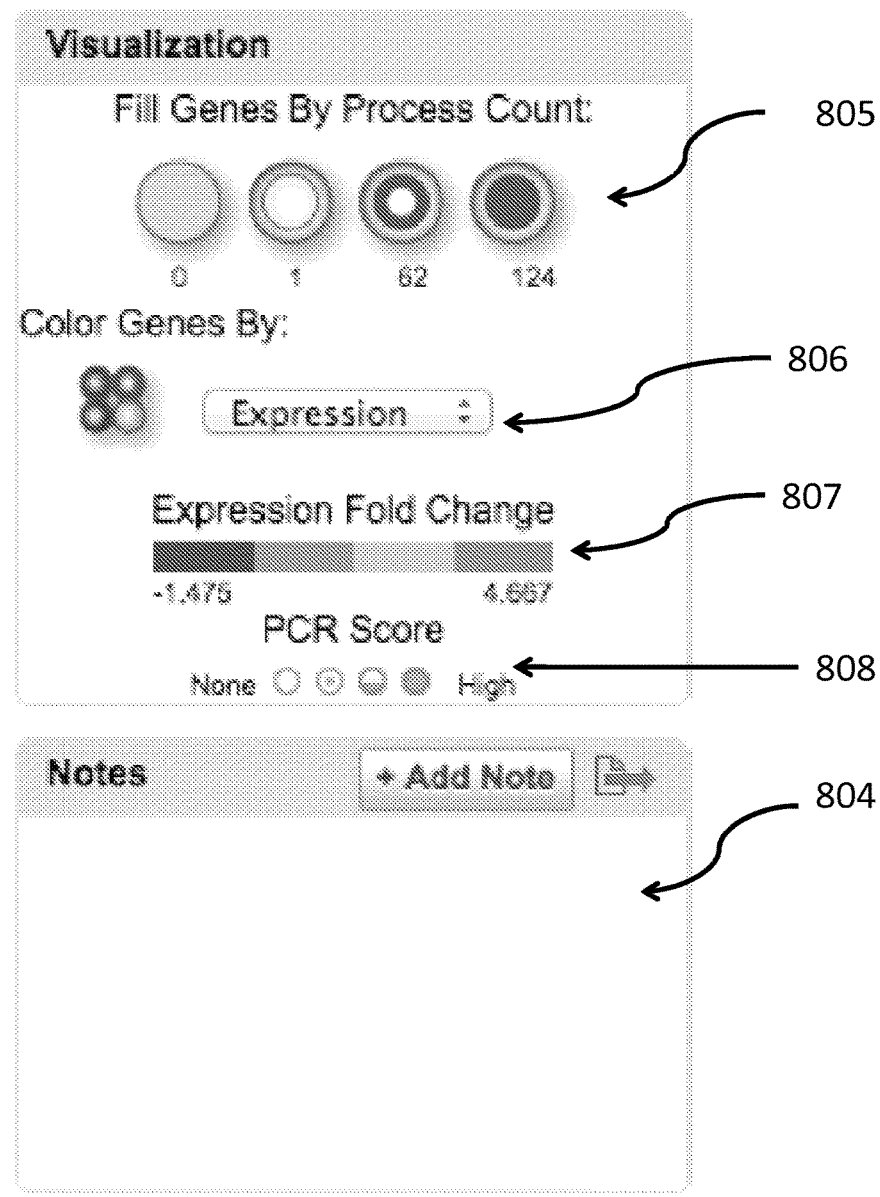

METHOD FOR BIOLOGICAL DATA ANALYSIS

CROSS-REFERENCE

This application claims priority under 35 U.S.C. § 119(e) to U.S. Provisional Patent Application No. 61/574,539 filed on Aug. 3, 2011 entitled "METHODS AND SYSTEMS FOR BIOLOGICAL DATA ANALYSIS." This application is herein incorporated by reference in its entirety.

INCORPORATION BY REFERENCE

Every patent, patent application, and non-patent publication recited herein is incorporated by reference in its entirety as if each patent, patent application and non-patent publication had been incorporated by reference individually.

BACKGROUND OF THE INVENTION

Modern molecular biology allows the analysis of millions of data points.

As molecular biological techniques have allowed researchers to generate larger and larger data sets solutions to assist in the visualization and interpretation of those data have often lagged. Often researchers use programs which are not purpose designed for the interpretation of biological data, such as Microsoft Excel. Where purpose built software does exist it often fails to relate data generated by a researcher with outside facts. For such an approach to be widely accepted a user interface that allows easy interpretation, manipulation, and analysis of large data sets is needed. Thus there remains a need for methods of combining the biological data sets with ontological databases built from private and public information sources, for instance published scientific articles.

SUMMARY OF THE INVENTION

In a first aspect, the present invention provides for a computer system for genomic data visualization comprising: (a) a data analysis module that is configured to (i) receive a user supplied data set; (ii) analyze the user supplied biological data set in association with an ontological database; and (iii) provide an output; and (b) a graphical user interface (GUI) configured to receive the output; wherein the GUI comprises a plurality of views; wherein at least one of the plurality of views is configured to provide a visualization of all or a subset of the output; wherein the visualization uses data icons and feature icons; wherein the data icons individually represent at least one datum originating from the user supplied biological data set and at least one visual metric of the data icon represents a data value provided by the output; wherein the feature icons individually represent at least one feature originating from the ontological database and at least one visual metric of the feature icon represents a feature value provided by the output; wherein the graphical user interface is configured to allow a user to apply a filter by interacting with a data or feature icon; wherein the filter is applied co-dependently in the plurality of views; and wherein the computer system comprises a stand alone computer, a multi-component computer, or a networked computer. In some embodiments, at least one view of the plurality of views is configured to display at least a second feature originating from the ontological database and wherein the at least one feature and the at least second feature comprise biological properties associated with the user supplied biological data set. In some embodiments, the at least one feature originating from the ontological database comprises a biological property. In some embodiments, the data icons further utilize at least a second visual metric representing one or more types of feature values provided by the output. In some embodiments, the one or more types of features are selected from the group consisting of pathways, processes, interactions, and diseases. In some embodiments, the visual metrics are customizable. In some embodiments, the graphical user interface is further configured to allow the user to assign the one or more types of data information to the at least one visual metric utilized by the data icons. In some embodiments, the graphical user interface is further configured to allow the user to assign the one or more types of feature information to the at least one visual metric utilized by the feature icons. In some embodiments, the graphical user interface is further configured to change the visualization of the one or more types of biological properties based on the filter co-dependently in a plurality of views. In some embodiments, the filter changes the visualization of data icons or feature icons. In some embodiments, the at least one visual metric utilized by the data icons is selected from the group consisting of color, color hue, color brightness, color saturation, shadowing, shape, a first text, a second text, a third text, a first dimension, a second dimension, a third dimension, location on the graph, distance from a predefined spot on the graph, icon-icon distance and clustering. In some embodiments, the at least one visual metric utilized by the feature icons is selected from the group consisting of color, color hue, color brightness, color saturation, shadowing, shape, a first text, a second text, a third text, a first dimension, a second dimension, a third dimension, location on the graph, distance from a predefined spot on the graph, icon-icon distance and clustering. In some embodiments, the graphical user interface is configured to allow a user to access the plurality of views by interacting with view selection icons on the graphical user interface. In some embodiments, the data value provided by the output is selected from the group consisting of expression fold change, numerical rank of p-vales, copy number, methylation status, single nucleotide polymorphism status, a PCR rank score and data quality metrics. In some embodiments, the feature value provided by the output is selected from the group consisting of isoforms, molecular function, number of diseases, processes, or interactions, cell location, mutation status drug target status, biomarker status, upstream interaction, downstream interaction, bi-directional interaction or binding interaction, connectivity rank score, biorank score, and total number of connected factors. In some embodiments, the feature value comprises a degree of association with one or more features with the user supplied biological data set. In some embodiments, the at least one view of the plurality of views displays data icons grouped in one or more elliptical areas. In some embodiments, the at least one view of the plurality of views displays feature icons outside of the one or more elliptical areas. In some embodiments, at least one of the one or more elliptical areas comprises a circular area. In some embodiments, in at least one view of the plurality of views, the data icons represent an involvement of a data icon associated data point from the user provided biological data set in a pathway. In some embodiments, in at least one view of the plurality of views, the data icons represent a number of pathways, wherein a data icon associated data point from the user provided biological data set is involved. In some embodiments, in at least one view of the plurality of views, the data icons represent an involvement of a data icon associated data point from the user provided biological data set in a process. In some embodiments, in at least one view of the plurality of views, the data icons represent a number of processes, wherein a data icon associated data point from the user provided biological data set is involved. In some embodiments, in at least one view of the plurality of views, the data icons represent an involvement of a data icon associated data point from the user provided biological data set in a disease. In some embodiments, in at least one view of the plurality of views, the data icons represent a number of diseases, wherein a data icon associated data point from the user provided biological data set is involved. In some embodiments, in at least one view of the plurality of views, the data icons represent an involvement of a data icon associated data point from the user provided biological data set in an interaction. In some embodiments, in at least one view of the plurality of views, the data icons represent a number of interactions, wherein a data icon associated data point from the user provided biological data set is involved.

In a second aspect, the invention provides for a computer system for genomic data visualization comprising: (a) a data analysis module that is configured to (i) receive a user supplied data set; (ii) analyze the user supplied biological data set in association with an ontological database; and (iii) provide an output; and (b) a graphical user interface (GUI) configured to receive the output and further configured to provide a visualization of all or a subset of the output; wherein the visualization uses data icons and feature icons; wherein the data icons individually represent at least one datum originating from the user supplied biological data set and at least one visual metric of the data icon represents a data value provided by the output; wherein at least two features originating from the ontological database are represented by the feature icons and at least one visual metric of each feature icon represents a feature value provided by the output; wherein the graphical user interface is configured to allow a user to apply a filter by interacting with a data or feature icon; and wherein the computer system comprises a stand alone computer, a multi component computer, or a networked computer. In some embodiments, the data icons are displayed grouped in one or more elliptical areas. In some embodiments, feature icons are displayed outside of the one or more elliptical areas. In some embodiments, at least one of the one or more elliptical areas comprises a circular area. In some embodiments, the at least two features originating from the ontological database comprise biological properties associated with the user supplied biological data set. In some embodiments, the at least two features originating from the ontological database comprise a biological property. In some embodiments, the data icons further utilize at least a second visual metric representing one or more types of feature values provided by the output. In some embodiments, the one or more types of features are selected from the group consisting of pathways, processes, interactions, and diseases. In some embodiments, the visual metrics are customizable. In some embodiments, the graphical user interface is further configured to allow the user to assign the one or more types of data information to the at least one visual metric utilized by the data icons. In some embodiments, the graphical user interface is further configured to allow the user to assign the one or more types of feature information to the at least one visual metric utilized by the feature icons. In some embodiments, the graphical user interface is further configured to change the visualization of the one or more types of biological properties based on the filter. In some embodiments, the filter changes the visualization of data icons or feature icons. In some embodiments, the at least one visual metric utilized by the data icons is selected from the group consisting of color, color hue, color brightness, color saturation, shadowing, shape, a first text, a second text, a third text, a first dimension, a second dimension, a third dimension, location on the graph, distance from a predefined spot on the graph, icon-icon distance and clustering. In some embodiments, the at least one visual metric utilized by the feature icons is selected from the group consisting of color, color hue, color brightness, color saturation, shadowing, shape, a first text, a second text, a third text, a first dimension, a second dimension, a third dimension, location on the graph, distance from a predefined spot on the graph, icon-icon distance and clustering. In some embodiments, the graphical user interface (GUI) further comprises a plurality of views providing a visualization of all or a subset of the output and the GUI is configured to allow a user to access the plurality of views by interacting with view selection icons on the GUI. In some embodiments, in at least one view of the plurality of views, the data icons represent an involvement of a data icon associated data point from the user provided biological data set in a pathway. In some embodiments, in at least one view of the plurality of views, the data icons represent a number of pathways, wherein a data icon associated data point from the user provided biological data set is involved. In some embodiments, in at least one view of the plurality of views, the data icons represent an involvement of a data icon associated data point from the user provided biological data set in a process. In some embodiments, in at least one view of the plurality of views, the data icons represent a number of processes, wherein a data icon associated data point from the user provided biological data set is involved. In some embodiments, in at least one view of the plurality of views, the data icons represent an involvement of a data icon associated data point from the user provided biological data set in a disease. In some embodiments, in at least one view of the plurality of views, the data icons represent a number of diseases, wherein a data icon associated data point from the user provided biological data set is involved. In some embodiments, in at least one view of the plurality of views, the data icons represent an involvement of a data icon associated data point from the user provided biological data set in an interaction. In some embodiments, in at least one view of the plurality of views, the data icons represent a number of interactions, wherein a data icon associated data point from the user provided biological data set is involved. In some embodiments, the data value provided by the output is selected from the group consisting of expression fold change, numerical rank of p-vales, copy number, methylation status, single nucleotide polymorphism status, a PCR rank score and data quality metrics. In some embodiments, the feature value provided by the output is selected from the group consisting of isoforms, molecular function, number of diseases, processes, or interactions, cell location, mutation status drug target status, biomarker status, upstream interaction, downstream interaction, bi-directional interaction or binding interaction, connectivity rank score, biorank score, and total number of connected factors. In some embodiments, the feature value comprises a degree of association with one or more features with the user supplied biological data set.

In a third aspect, the invention provides for a system for genomic data manipulation comprising: (a) a graphical user interface made up of a multitude of user selectable icons representing biological properties of interest; (b) one or more additional icons representing a user supplied biological data set; and (c) an ontological database, which is integrated with the icons and which stores information for associating the user supplied biological data set and the biological properties of interest; wherein a level of association between a data point within the user supplied biological data set and one of the biological properties of interest is displayed on the graphical user interface with the set of biological properties of interest using a visual metric; and wherein the system comprises a stand alone computer, a multicomponent computer, or a networked computer. In one embodiment, the system's biological properties of interest are selected from the group consisting of protein function, homology, phenotype, gene expression, copy number, localization, or association with disease. In one embodiment, the system has a: (a) the user selectable icons representing biological properties of interest are in a circular pattern on the graphical user interface; and (b) the additional icons representing the user supplied biological data set are located within the circle.

In a fourth aspect, the invention provides for a system for biological data analysis comprising: (a) a graphical user interface comprising; (i) a first set of icons associated with a set of biological properties from an ontological database; and (ii) a second set of icons associated with a user provided biological data set; and (b) an analysis module determining at least one association between the biological properties and the biological data set; wherein at least one of the icon sets display the at least one association using at least one visual metric on at least a portion of the icon. In one embodiment, the system's content of the user provided biological data set is gene expression, genotyping, sequencing, single nucleotide polymorphism, copy number variation, haplotyping, genomic structure, protein expression, protein modification, protein-protein interaction, protein localization, or drug response or a combination thereof. In one embodiment, the system has the biological properties which are biological pathways, biological processes, biological or chemical functions, cellular locations, phenotypes, associations with diseases or disease states, locations within a genome, co-expression profiles, co-localization profiles, associations with tissues, associations with developmental stages or networks, or a combination thereof. In one embodiment, the system has an ontological database which links the contents of a user provided biological data set to biological properties. In one embodiment, the system has an ontological database which is amended by supplemental information from a user. In one embodiment, the system has a restricted access is provided to one or more user(s) to the amended database. In one embodiment, the system has the ontological database which is installed at a user site. In one embodiment, the system has ontological database which is installed on a remote computer server to the user site. In one embodiment, the system has the graphical user interface which is comprised of one or more input fields that accept a search query, which is used to conduct a search in the ontological database. In one embodiment, the system has visual metric is selected from the group of visual attributes consisting of color, color hue, shadowing, shape, a first text, a second text, a third text, a first dimension, a second dimension, a third dimension, location on the graph, distance from a predefined spot on the graph, icon-icon distance and clustering. In one embodiment, the system has at least one visual metric associated with at least one icon is adjusted upon a computer mediated user interaction with the icon. In one embodiment, the system has set of icons associated with the biological properties is subjected to at least one filter, wherein the set of icons associated with the biological properties is filtered to a subset. In one embodiment, the system has a set of icons associated with the user provided biological data set is subjected to at least one filter, wherein the set of icons associated with the user provided biological data set is filtered to a subset. In one embodiment, the system has a filter which is based on the filtering applied to the set of icons associated with the biological properties. In one embodiment, the system has a filter which is based on the content of the user provided biological data set. In one embodiment, the system has a filter which is based on a computer mediated user interaction with at least one icon. In one embodiment, the system has a filter which is based on a script. In one embodiment, the system's script comprises one or more step(s) from prior user interaction with the system. In one embodiment, the system's graphical user interface is furthered comprised of at least one input field accepting at least one user provided criterion as an auxiliary input. In one embodiment, the system's auxiliary input is entered by a user selecting from a list of auxiliary input options that are provided on the graphical user interface. In one embodiment, the system's the auxiliary input is entered by the user in the form of plain text. In one embodiment, the system's input is interpreted using natural language processing. In one embodiment, the system has a filter applied to the set of icons associated with the biological properties is determined using the at least one auxiliary input. In one embodiment, the system's filter applied to the set of icons associated with the user provided biological data set is determined using the at least one auxiliary input. In one embodiment, the system has at least one association between the biological properties and the user provided biological data set is determined for a subset of biological properties and a subset of user provided biological data set that are associated with the subset of remaining icons after the icons are subjected to at least one filter. In one embodiment, the system at least one association between the biological properties and the user provided biological data set is determined using the at least one auxiliary input. In one embodiment, the system has at least one filter is removed, wherein the filtering associated with the filter is reversed. In one embodiment, the system is further comprised of one or more data processing module(s) converting the user provided biological data set to an accepted data format by the graphical user interface. In one embodiment, the system has a plurality of data processing modules process the user provided biological data set sequentially and at least one data processing module accepts an output from another data processing module as an input.

In a fifth aspect, the invention provides for a method comprising the steps of: providing to a user a code to access an ontological database equipped to analyze a user provided biological data set, wherein the ontological database is stored in a stand alone computer, a multicomponent computer, or a networked computer; and wherein (a) the code is provided upon the purchase of a product, wherein the product is used to generate the data set; (b) the code allows for repeated analysis of the data set using the ontological database; and (c) the user provided data set is a processed biological data set or any other data set.

In a fifth aspect, the invention also provides for a method comprising the steps of: providing to a user a code to access an ontological database equipped to analyze a user provided biological data set, wherein the ontological database is stored in a stand alone computer, a multicomponent computer, or a networked computer; and wherein (a) the code is provided upon the purchase of a product, wherein the product is used to generate the data set; (b) the code allows for repeated analysis of the data set using the ontological database; and (c) the user provided data set is an unprocessed biological data set. In one embodiment, the method's analysis step comprises scoring and displaying the level of association for individual members within the user provided data set with a set of properties stored in the ontological database. In one embodiment, the method's ontological database comprises interrelated information for (a) biological pathways, biological processes, biological or chemical functions, cellular locations, phenotypes, associations with diseases or disease states, locations within a genome, co-expression profiles, co-localization profiles, associations with tissues, associations with developmental stages or networks, and (b) gene expression, genotyping, sequencing, single nucleotide polymorphism, copy number variation, haplotyping, genomic structure, protein expression, protein modification, protein-protein interaction, protein localization and drug response.

In a sixth aspect, the invention provides for a method comprising the steps of: (a) obtaining a code associated with a product or service necessary to generate a biological data set; (b) generating the biological data set or any other data set; (c) using the code to unlock tools to access an ontological database to analyze the data set wherein the ontological database is stored in a stand alone computer, a multicomponent computer, or a networked computer; and (d) analyzing the data set. In one embodiment, the method is further comprised of selecting a therapy related to the biological data set based upon the analysis of the data set.

In a seventh aspect, the invention provides for a method comprising the steps of: (a) determining a set of experimental design criteria; (b) inputting the experimental design criteria into a system for prioritizing experimental results; (c) generating a biological data set using the experimental design criteria; (d) inputting the biological data set into the system for prioritizing experimental results; and (e) initiating a program whereby the system for prioritizing experimental results queries an ontological database for relationships based upon the experimental design criteria, compares the relationships to the biologic data set generated using the experimental design criteria, and prioritizes the biological data set based upon the comparison; wherein the system for prioritizing experimental results comprises a stand alone computer, a multicomponent computer, or a networked computer. In one embodiment, the method's generating the biological data set comprises sequencing a nucleotide, gene expression determination by qualitative RT-PCR, gene chip hybridization, mass spectrometry data, antibody readout of gene expression products such abundance, phosphorlaytion status or activation state.

In some embodiments the invention provides a system for genomic data manipulation comprising: a) a graphical user interface made up of a multitude of user selectable icons representing biological properties of interest; b) additional icons representing a user supplied biological data set; and c) an ontological database, which is integrated with the icons and which stores information for associating the user supplied biological data set and the biological properties of interest; wherein a level of association between a data point within the user supplied biological data set and one of the biological properties of interest is displayed on the graphical user interface with the set of biological properties of interest using a visual metric. In some embodiments the biological properties of interest comprise protein function, homology, phenotype, gene expression, copy number, localization, isoform or association with disease. In some embodiments the user selectable icons representing biological properties of interest are in a circular pattern on the graphical user interface; and the additional icons representing the user supplied biological data set are located within the circle.

In some embodiments the invention provides a system for biological data analysis comprising: a) a graphical user interface comprising; i) a first set of icons associated with a set of biological properties from an ontological database; and ii) a second set of icons associated with a user provided biological data set; and b) an analysis module determining at least one association between the biological properties and the biological data set; wherein at least one of the icon sets display the at least one association using at least one visual metric on at least a portion of the icon. In some embodiments the content of the user provided biological data set is gene expression, genotyping, sequencing, single nucleotide polymorphism, copy number variation, methylation status, haplotyping, genomic structure, protein expression, protein modification, protein-protein interaction, protein localization, or drug response or a combination thereof. In some embodiments the biological properties are biological pathways, biological processes, biological or chemical functions, cellular locations, phenotypes, associations with diseases or disease states, locations within a genome, co-expression profiles, co-localization profiles, associations with tissues, associations with developmental stages or networks, or a combination thereof. In some embodiments the ontological database links the contents of a user provided biological data set to biological properties. In some embodiments the ontological database is amended by supplemental information from a user. In some embodiments a restricted access is provided to one or more user(s) to the amended database. In some embodiments the ontological database is installed at a user site. In some embodiments the ontological database is installed on a remote computer server to the user site. In some embodiments the graphical user interface comprises one or more input fields that accept a search query, which is used to conduct a search in the ontological database. In some embodiments the visual metric is selected from the group of visual attributes consisting of color, color hue, shadowing, shape, a first text, a second text, a third text, a first dimension, a second dimension, a third dimension, location on the graph, distance from a predefined spot on the graph, icon-icon distance and clustering. In some embodiments at least one visual metric associated with at least one icon is adjusted upon a computer mediated user interaction with the icon. In some embodiments the set of icons associated with the biological properties is subjected to at least one filter, wherein the set of icons associated with the biological properties is filtered to a subset. In some embodiments the set of icons associated with the user provided biological data set is subjected to at least one filter, wherein the set of icons associated with the user provided biological data set is filtered to a subset. In some embodiments the filter is based on the filtering applied to the set of icons associated with the biological properties. In some embodiments the filter is based on the content of the user provided biological data set. In some embodiments the filter is based on a computer mediated user interaction with at least one icon. In some embodiments the filter is based on a script. In some embodiments the script comprises one or more step(s) from prior user interaction with the system. In some embodiments the graphical user interface further comprises at least one input field accepting at least one user provided criterion as an auxiliary input. In some embodiments the auxiliary input is entered by a user selecting from a list of auxiliary input options that are provided on the graphical user interface. In some embodiments the auxiliary input is entered by the user in the form of plain text. In some embodiments the input is interpreted using natural language processing. In some embodiments the filter applied to the set of icons associated with the biological properties is determined using the at least one auxiliary input. In some embodiments the filter applied to the set of icons associated with the user provided biological data set is determined using the at least one auxiliary input. In some embodiments the at least one association between the biological properties and the user provided biological data set is determined for a subset of biological properties and a subset of user provided biological data set that are associated with the subset of remaining icons after the icons are subjected to at least one filter. In some embodiments the at least one association between the biological properties and the user provided biological data set is determined using the at least one auxiliary input. In some embodiments at least one filter is removed, wherein the filtering associated with the filter is reversed. In some embodiments the system further comprises one or more data processing module(s) converting the user provided biological data set to an accepted data format by the graphical user interface. In some embodiments a plurality of data processing modules process the user provided biological data set sequentially and at least one data processing module accepts an output from another data processing module as an input.

In some embodiments the invention provides a method comprising the steps of: providing to a user a code to access an ontological database equipped to analyze a user provided biological data set, wherein a) the code is provided upon the purchase of a product, wherein the product is used to generate the data set; b) the code allows for repeated analysis of the data set using the ontological database; and c) the user provided data set is a processed biological data set.

In some embodiments the invention provides a method comprising the steps of: providing to a user a code to access an ontological database equipped to analyze a user provided biological data set, wherein a) the code is provided upon the purchase of a product, wherein the product is used to generate the data set; b) the code allows for repeated analysis of the data set using the ontological database; and c) the user provided data set is an unprocessed biological data set. In some embodiments the analysis comprises scoring and displaying the level of association for individual members within the user provided data set with a set of properties stored in the ontological database. In some embodiments the ontological database comprises interrelated information for a) biological pathways, biological processes, biological or chemical functions, cellular locations, phenotypes, associations with diseases or disease states, locations within a genome, co-expression profiles, co-localization profiles, associations with tissues, associations with developmental stages or networks, and b) gene expression, genotyping, sequencing, single nucleotide polymorphism, isoform, copy number variation, haplotyping, genomic structure, protein expression, protein modification, protein-protein interaction, protein localization and drug response.

In some embodiments the invention provides a method comprising the steps of: a) obtaining a code associated with a product or service necessary to generate a biological data set; b) generating the biological data set; c) using the code to unlock tools to access an ontological database to analyze the data set; and d) analyzing the data set. In some aspects of the invention, the method further comprises selecting a therapy related to the biological data set based upon the analysis of the data set. In some aspects of the invention, the method further comprises selecting a biomarker related to the biological data set based upon the analysis of the data set. In some aspects of the invention, the method further comprises selecting a drug target related to the biological data set based upon the analysis of the data set.

In some embodiments the invention provides a method comprising the steps of: a) determining a set of experimental design criteria; b) inputting the experimental design criteria into a system for prioritizing experimental results; c) generating a biological data set using the experimental design criteria; d) inputting the biological data set into the system for prioritizing experimental results; and e) initiating a program whereby the system for prioritizing experimental results queries an ontological database for relationships based upon the experimental design criteria, compares the relationships to the biologic data set generated using the experimental design criteria, and prioritizes the biological data set based upon the comparison. In some embodiments the generating the biological data set comprises sequencing a nucleotide.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5(C) depicts an embodiment of the "Summary" module illustrating the graphical user summary of "Top Results base on Key Words" 580 and in the lower plane the results are divided into "Top Pathways", "Top Processes" and "Top Diseases" 585.

FIG. 8(C) depicts an embodiment of the "Processes" module illustrating the graphical user interface to allow the user to analyze the process graph from a computer interface pull-down menu 806.

FIG. 11(A) depicts an embodiment of the system illustrating the graphical user interface being accessed by a user in a "Gene Table" view 1101.

DETAILED DESCRIPTION OF THE INVENTION

Figure 1:
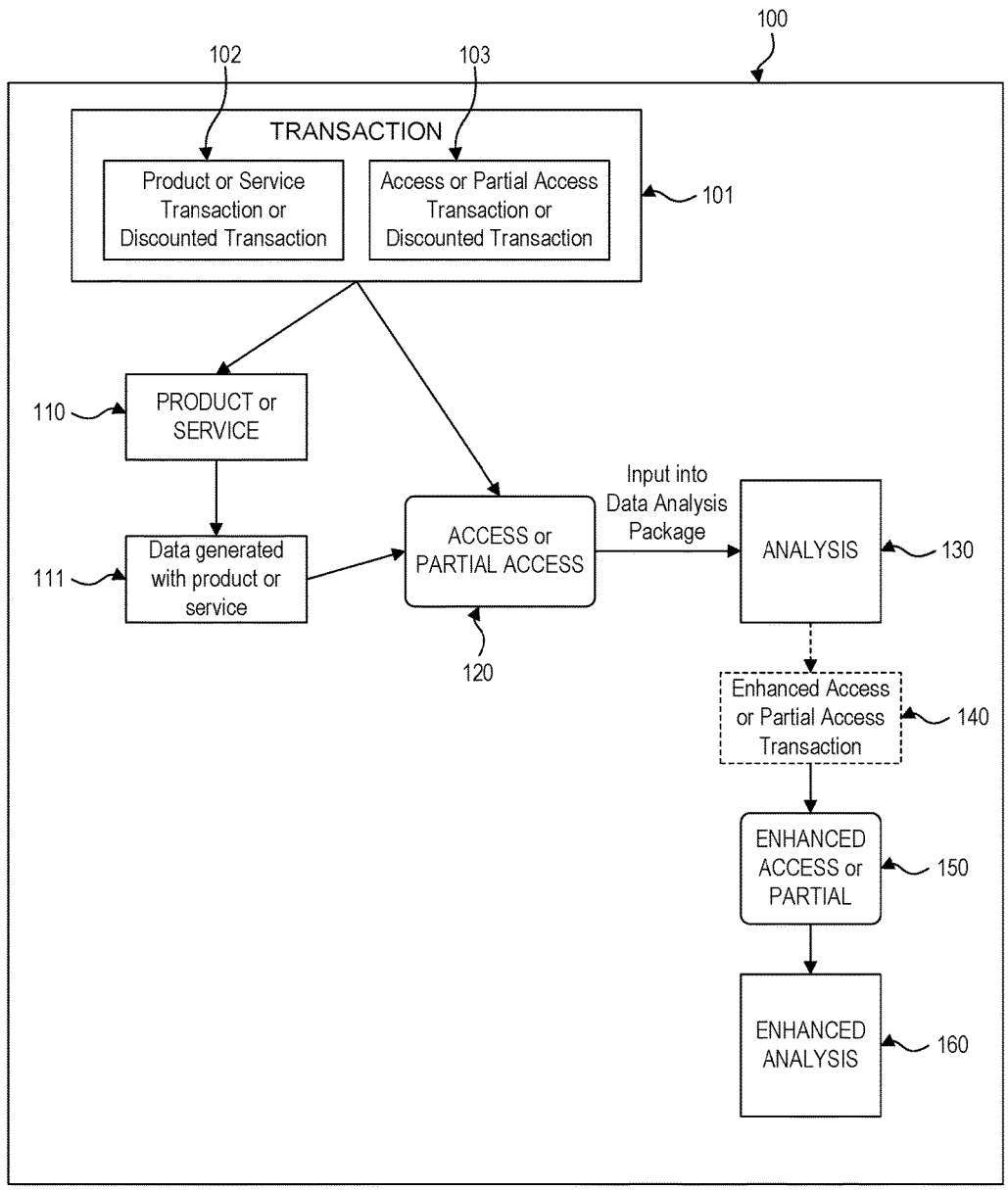
FIG. 1 depicts an embodiment of the system including a transactional model for granting a user access to a data analysis package.

Systems and methods for analysis and display of data comprising a graphical user interface are described herein. A data analysis system for improved visualization of user provided data in light of information from a database is provided. The user provided data set can be, for example, a biological data set. A highly interactive visual element for iconized visualization of data points/members of the data set can be incorporated into the data analysis system. Icons representing data points/members and visualizing values associated to the same are described. Additional icons representing features, for example biological properties, which are associated with the user provided data set are also provided. Methods for filtering operations are provided for facile, dynamic visualization of data points and features associated with the data points. Methods are provided for real-time entry of user input in line with the analysis workflow. A preconfigured and integrated ontological database provides information to a workflow and statistical pipeline. Accordingly, scoring algorithms automatically correlate user provided input with user a provided data set utilizing information from the ontological database and prioritizing the most relevant findings in light of the user provided input. Methods for a transactional bundling model are also provided. Accordingly, the bundling relates transactions involving the purchase of a product or service that is used to generate a data set with transactions involving access to a data analysis package that is used to visualize or analyze the data set.

The methods and systems in various embodiments of the invention comprise computer systems for storing and accessing genomics information and for computational analysis of complex relationships among the stored concepts. Such methods and systems may comprise a computer system, e.g., any type of system that comprises stored, e.g., digitized, data and typically enabling entry, query, display and analysis of the stored data. Such computer system can be a stand alone computer, a multi-component computer, e.g., one in which the stored data are physically remote from the user interface, networked computers, etc. Any known method or module in the art for updating, querying, displaying, and analyzing the contents of the databases described herein will be useful, e.g., software and hardware for electronically searching fields, categories or whole databases.

User Interface

The systems and methods of the invention allow for the use of user interfaces facilitating the interaction with the computer systems by the user described herein.

In various aspect of the invention, direct interfaces allow users to manipulate objects presented to them, using actions that correspond to the physical world. Graphical user interfaces (GUI) accept input via devices, such as computers keyboards, mouses, touchpads, microphones, or cameras. GUIs provide graphical output which is projected on a screen such as a computer monitor, or from a projector. The graphical outputs used by GUIs can include but not limited to object-oriented user interfaces (OOUIs) and application oriented interfaces. Smaller computer devices, such as mobile devices for example PDAs, smart phones, touch pads can use the WIMP ("window, icon, menu, pointing device") elements with post-WIMP environments, utilizing space constraints and the availability of input devices. Further examples of suitable user interfaces that can used with the invention include: web user interfaces (WUI) that accept input and provide output by generating webpages, which are transmitted though the Internet and viewed by the user using a web browser program. Example of suitable web browser programs include but are not limited to those that utilize Java, Ajax, Adobe Flex, Microsoft .NET, or similar technologies to provide real-time control in a separate program. Touch screen displays can also be used in some aspects of the invention. Touch screen displays accept input by the touch of fingers or a stylus, including those that are used as a combined input output device. Command line interfaces displays can also be used in some aspects of the invention Command line interfaces, is an interface in which the user provides the input by typing a command string with the computer keyboard and the system provides output by printing text on the computer monitor. Conversational Interface Agents can also be used in some aspects of the invention. Conversational Interface Agents function to personify the computer interface in the form of an animated person, robot, or other character and present interactions in a conversational form. Crossing-based interfaces can also be used in some aspects of the invention. Crossing-based interfaces are computer interface in which the primary input task consists in crossing boundaries. Gesture interfaces are envisioned to be used in some aspects of the invention. Gesture interfaces are computer-user interfaces that accept input in a form of e.g. hand gestures, or mouse gestures sketched with a computer mouse or a stylus; motion tracking interfaces that monitor the user's body motions and translate them into commands. In some aspect of the invention multi-screen interfaces can be used. Multi-screen interfaces employ multiple displays to provide a more flexible interaction; text user interfaces, which output text, but accept other form of input in addition to or in place of typed command strings. The invention can also be used with voice user interfaces. Voice user interfaces function by accepting input and provide output by generating voice prompts and accepting verbal input. Natural-Language interfaces are envisioned to be used in some aspects of the invention. Natural-Language interfaces can be used for search engines and on webpages and wherein a user can type in a question and wait for a response from a qualified technician, scientist or other user. The invention can also be used with zooming user interfaces, in which information objects are represented at different levels of scale and detail, and where the user can change the scale of the viewed area in order to show more detail. All of list interfaces non-limiting examples that can be used with the invention. However, related and/or improved version of such computer interfaces are also envisioned to be used with the invention.

Computer Systems

The systems and methods of the present invention are enacted on and/or by using computer systems. Examples of computer systems of the invention are described below. Variations upon the described computer systems are possible so long as they provide the platform for the systems and methods of the invention.

Figure 13:
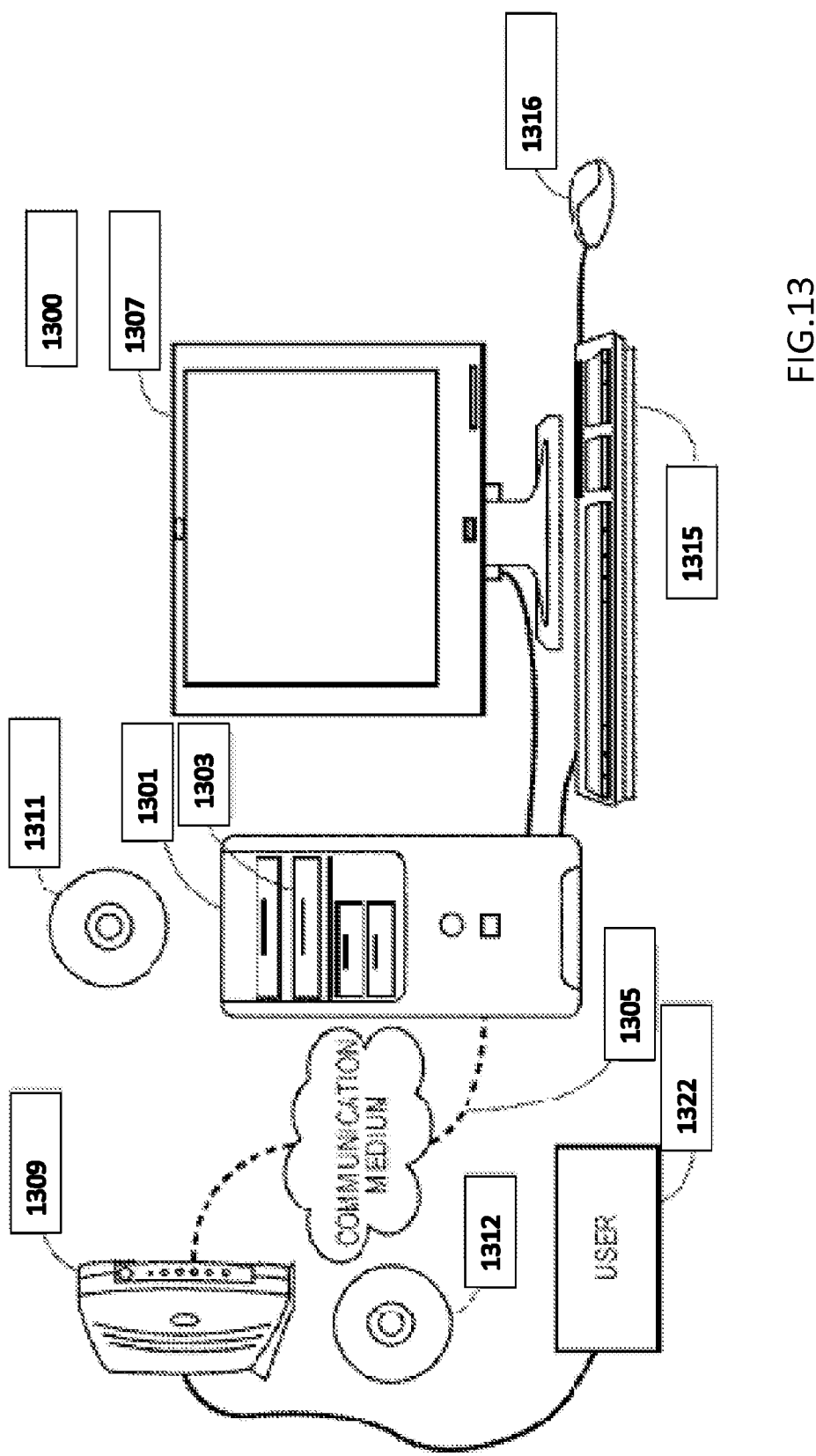
FIG. 13 illustrates an embodiment of various components of a generalized computer system 1300.

An example of computer system of the invention is illustrated in FIG. 13. The computer system 1300 illustrated in FIG. 13 may be understood as a logical apparatus that can read instructions from media 1311 and/or a network port 1305, which can optionally be connected to server 1309 having fixed media 1312. The system, such as shown in FIG. 13 can include a CPU 1301, disk drives 1303, optional input devices such as keyboard 1315 and/or mouse 1316 and optional monitor 1307. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 1322 as illustrated in FIG. 13.

Figure 14:
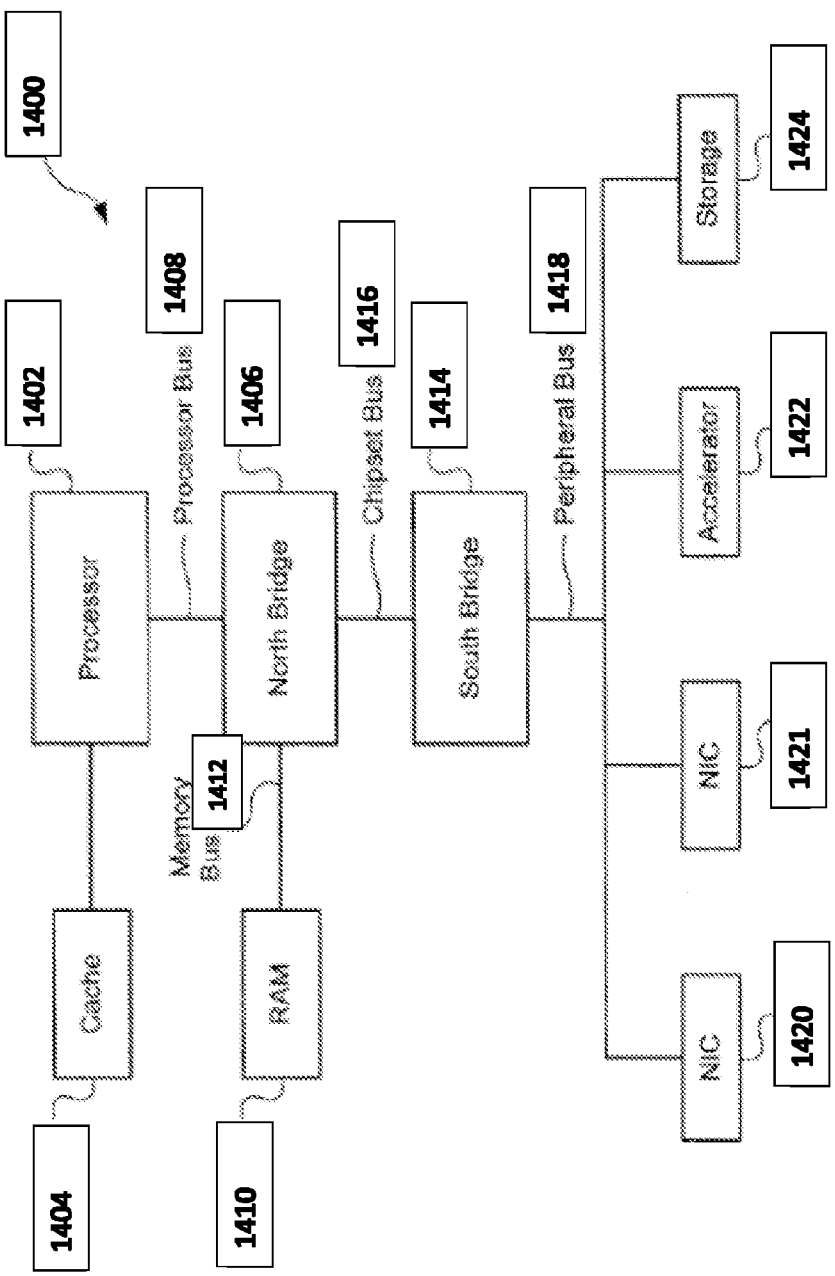
FIG. 14 is a diagram illustrating an embodiment of an architecture of a computer system that can be used in connection with embodiments of the present invention 1400.

FIG. 14 is a block diagram illustrating an example architecture of a computer system 1400 that can be used in connection with example embodiments of the present invention. As depicted in FIG. 14, the example computer system can include a processor 1402 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell MCA 930™ processor, or a functionally-equivalent processor. Multiple threads of execution can be used for parallel processing. In some aspects of the invention, multiple processors or processors with multiple cores can also be used, whether in a single computer system, in a cluster, or distributed across systems over a network comprising a plurality of computers, cell phones, and/or personal data assistant devices.

As illustrated in FIG. 14, a high speed cache 1404 can be connected to, or incorporated in, the processor 1402 to provide a high speed memory for instructions or data that have been recently, or are frequently, used by processor 1402. The processor 1402 is connected to a north bridge 1406 by a processor bus 1408. The north bridge 1406 is connected to random access memory (RAM) 1410 by a memory bus 1412 and manages access to the RAM 1410 by the processor 1402. The north bridge 1406 is also connected to a south bridge 1414 by a chipset bus 1416. The south bridge 1414 is, in turn, connected to a peripheral bus 1418. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 1418. In some alternative architectures, the functionality of the north bridge can be incorporated into the processor instead of using a separate north bridge chip.

In some aspects of the invention, system 100 can include an accelerator card 1422 attached to the peripheral bus 1418. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 1424 and can be loaded into RAM 1410 and/or cache 1404 for use by the processor. The system 1400 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention.

In this example, system 1400 also includes network interface cards (NICs) 1420 and 1421 connected to the peripheral bus for providing network interfaces to external storage, such as Network Attached Storage (NAS) and other computer systems that can be used for distributed parallel processing.

Figure 15:
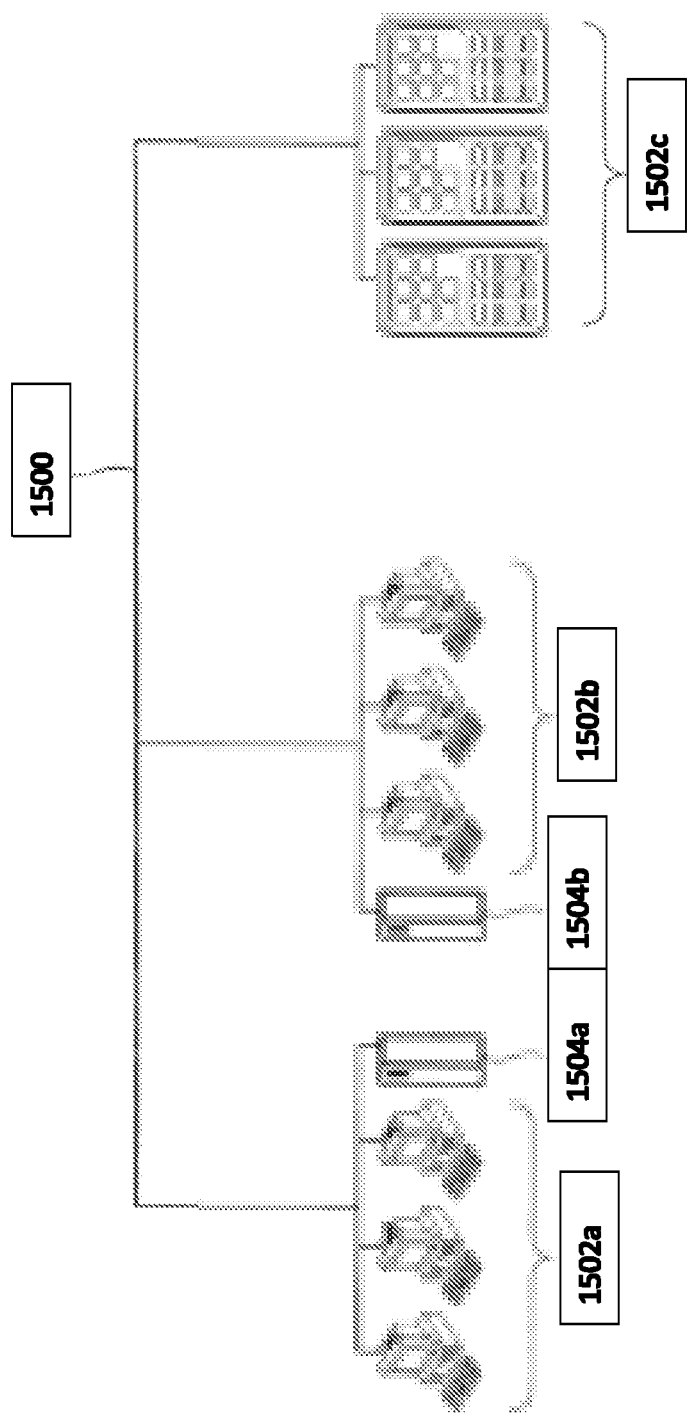
FIG. 15 is a diagram illustrating an embodiment of a computer network that can be used in connection with embodiments of the present invention 1500.

FIG. 15 is a diagram showing a network 1500 with a plurality of computer systems 1502a, and 1502b, a plurality of cell phones and personal data assistants 1502c, and Network Attached Storage (NAS) 1504a, and 1504b. In example embodiments, systems 1502a, 1502b, and 1502c can manage data storage and optimize data access for data stored in Network Attached Storage (NAS) 1504a and 1504b. A mathematical model can be used for the data and be evaluated using distributed parallel processing across computer systems 1502a and 1502b and cell phone and personal data assistant systems 1502c. Computer systems 1502a, and 1502b, and cell phone and personal data assistant systems 1502c can also provide parallel processing for adaptive data restructuring of the data stored in Network Attached Storage (NAS) 1504a and 1504b. A wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

Figure 16:
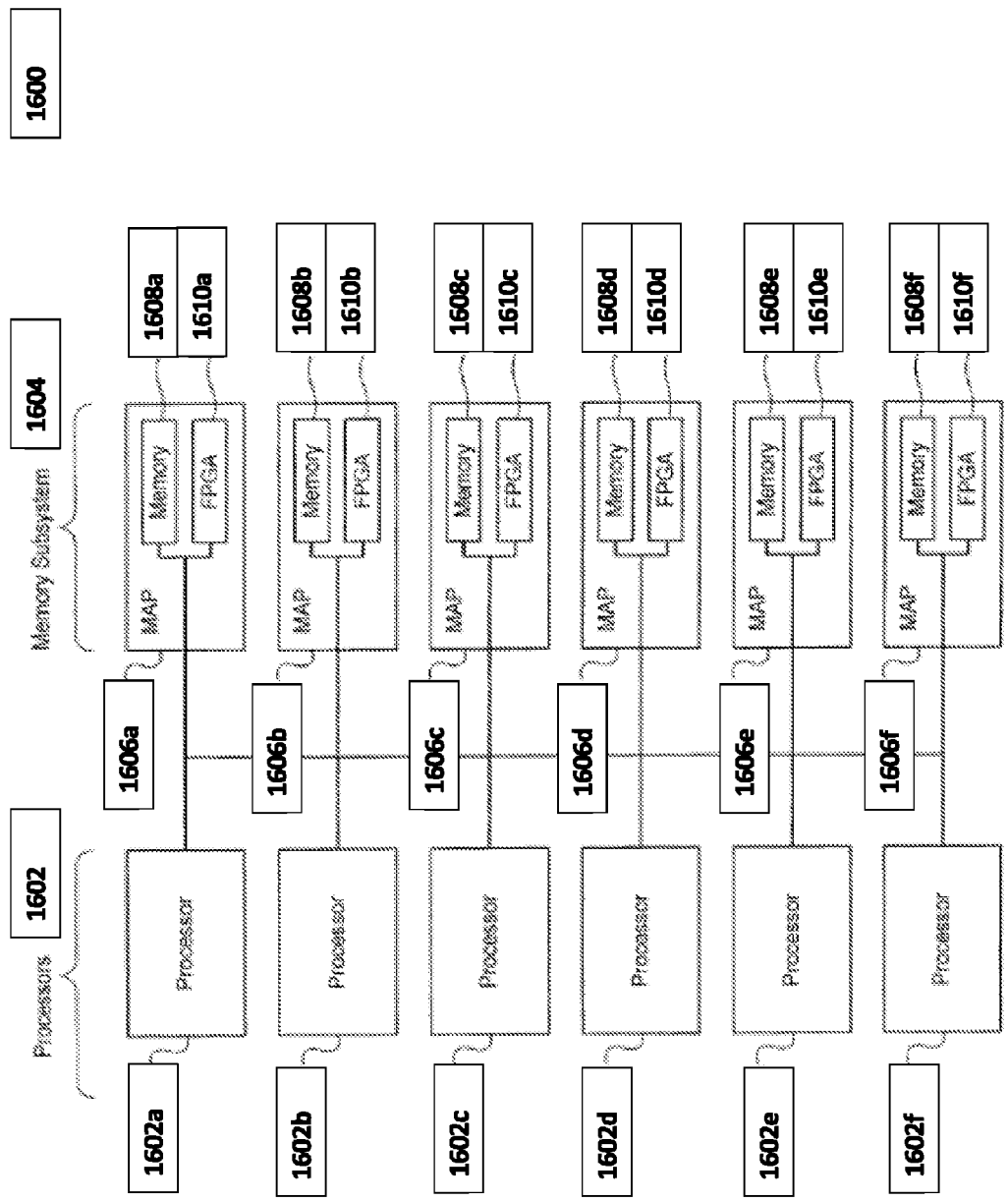
FIG. 16 is a diagram illustrating an embodiment of architecture of a computer system that can be used in connection with embodiments of the present invention 1600.

FIG. 16 is a block diagram of a multiprocessor computer system 1600 using a shared virtual address memory space in accordance with an example embodiment. The system includes a plurality of processors 1602a-f that can access a shared memory subsystem 1604. The system incorporates a plurality of programmable hardware memory algorithm processors (MAPs) 1606a-f in the memory subsystem 1604. Each MAP 1606a-f can comprise a memory 1608a-f and one or more field programmable gate arrays (FPGAs) 1610a-f. The MAP provides a configurable functional unit and particular algorithms or portions of algorithms can be provided to the FPGAs 1610a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 1608a-f, allowing it to execute tasks independently of, and asynchronously from, the respective microprocessor 1602a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some aspects of the invention, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 16, system on chips (SOCs), application specific integrated circuits (ASICs), or other processing and logic elements. For example, the Set Processor and Optimizer can be implemented with hardware acceleration through the use of a hardware accelerator card, such as accelerator card 1422 illustrated in FIG. 14.

Access from Remote Computers/Handheld Devices

In some aspect of the invention, the system and methods of the invention relate to accessing the systems of the invention remotely. Additional or secondary computers, such as desktop or laptop computers, mobile devices, for example handheld devices, mobile phones, or any other suitable computer known in the art may access the computer systems of the invention remotely. Secondary computers may access the systems remotely through a wired or wireless network. In some aspects of the invention, the secondary computers send and/or receive data to or from the systems using an application programming interface (API). In other aspects of the invention, the secondary computers may run the computer systems, for example using a VPN. Data stored on the systems may be replicated and/or mirrored on the secondary computers obtaining remote access as desired or on a regular schedule determined by the user. In some aspect of the invention, a secondary computer connecting to the systems is operably linked to another instrument, for example a laboratory instrument. Examples of laboratory instruments that can operably linked include but are not limited to: a sequencer, a gene chip reader, qPCR machine, cell plate reader, high-content cell reader, mass spectrometry, or a flow cytometry machine. The computer systems and the secondary computer may thus link laboratory instruments to the systems and methods of the invention for direct input into the system. For example, an automated sequencer or microarray reader or any other analyzer known in the art for generating genomics data may interact with the systems of the invention to provide tools for local visualization and manipulation of the data generated by the sequencer without requiring a user to upload the data. A direct link can be used to upload the data on demand of the user or it can be used to upload data after a particular cycle occurs. The visualization and manipulation tools can utilize ontologic databases stored remotely, for example in a network.

Network Systems

Various embodiments of the invention utilize one or more networks, such as a Local Area Network (LAN), Wireless LAN (WLAN), and in some cases a Storage Area Network (SAN), a Campus Area Network (CAN), Metropolitan Area Network (MAN) or Wide Area Network (WAN), to provide communication between one or more computers integrated in the system. Physical computer to computer or computer to device communications can be achieved through any standard commercially available hardware and software. An example of hard-wired networking is the ANSI/IEEE 802.3 (CSMA/CD) standard, utilized as the LAN communication protocol with appropriate networking software and interface cards. In large installations where several individual locations are linked to a central facility, the LANs can subsequently be connected to a user third party WAN. Optical fibers, twisted pair, or coax cable can be used to couple the network computers together. Communication can also be achieved through satellite, telephone lines, TV cable networks, Internet or any other protocols allowing for bi-directional communications. Examples of networked computer/device systems are further described in U.S. Pat. No. 6,055,487, which is herein incorporated by reference in its entirety.

In some aspects of the invention, multiple computers may connect to multiple storage systems through a Storage-Area Network (SAN), a Network-attached storage (NAS), or a hybrid thereof. A storage area network (SAN) is a dedicated, centrally managed, information infrastructure, which enables interconnection of compute nodes and storage nodes. A storage area network facilitates universal access and sharing of storage resources. SANs are often implemented with Fibre Channel technology as known in the art. Typically, a SAN utilizes block-oriented protocols, such as a SCSI-like protocols encapsulated within Fibre Channel frames, for providing storage to compute nodes. However, file systems, known as SAN files systems or shared disk file systems, can be built on top of SANs do provide file-level access. In contrast, general purpose networks (GPNs), including local area networks (LANs), wide area networks (WANs) and the Internet typically implement file-oriented protocols. Some storage area networks may encapsulate block oriented protocols in other protocols, such as an iSCSI protocol.

In some cases, it is possible to find more than one path through a SAN from the computer to one or more of the storage devices. When more than one such path exists, the path over which data is communicated can be controlled and it may become possible or desirable to distribute communications among the multiple paths. Network solutions for integrated controlling/monitoring/device systems are further described in U.S. Pat. No. 6,985,983, which is herein incorporated by reference in its entirety.

In various aspects of the invention, the computer system that is directly connected to a primary piece of laboratory equipment, such as sequencers, microarray readers or other analyzers known in the art for generating genomics data, acts as a hub, for example a WLAN hub, for a network.

Drivers, Applications, and Operating Systems

In various aspects of the invention, the operating system (OS) of the central/controller computer is equipped with application programming interfaces for easy installation of additional drivers and/or applications.

In some aspects of the invention, a separate OS driver may be utilized for each operating system, interface adapter and device protocol combination. Any OS can be used, including LINUX, UNIX, MAC OS X, GOOGLE CHROME OS, MICROSOFT WINDOWS, MINIX, SINGULARITY or any other suitable OS known in the art.

An OS driver may be installable into the operating system it is designed for by a variety of users, for example when a user supplements the integrated system with a new device. The driver can generate control sequences according to the device protocol for each device supported. These control sequences can be passed from the OS driver, typically through an interface adapter, to the device, for example over any relevant cabling or wireless solution. Data and command response information can be returned from the device through the interface adapter to the OS driver.

In some aspects of the invention, fewer but more complex installable OS drivers may be used. With this approach, a single complex OS driver can be used with a desired operating system and can have the ability to interface OS-specific system-call commands to device-specific commands for each of the device types that may connect to each adapter. Such complex OS drivers may typically contain an OS-interface module for communicating with the OS; command interpreting and translation modules, dedicated to different types of devices in communication with the OS-interface module; redundancy control modules operating in tandem with command interpreting and translation modules for controlling redundant features of various types of devices; an adapter-interface module in communication with the adapter and with the command interpreting and translation modules; and/or a redundancy control module operating in conjunction with the adapter-interface module to control any path redundancy that may exist. Features of such complex drivers are further described in U.S. Pat. No. 6,985,983, which is herein incorporated by reference in its entirety.

Integrated Systems

In some aspects of the invention, a network, such as a LAN, WLAN, CAN, MAN, WAN or SAN, provides communication between the devices and the controlling/monitoring stations and data storage stations. A computer interface may provide bi-directional communication between analytical instruments, robots and peripheral devices and a computer. In various aspects of the invention, the system employs a robot which is responsive to computer commands and capable of performing mechanical functions. Systems incorporating multiple controllers and peripheral devices in a network are exemplified in U.S. Pat. No. 5,366,896, which is herein incorporated by reference in its entirety.

Various features of the user interface may allow for quick, efficient, simple control of the laboratory equipment in the system. Accordingly, collaboration between local and networked users may be facilitated.

Interfaces—Application Programming Interfaces

In some aspects of the invention, network software (e.g., Novell, Banyan, Windows NT, UNIX, etc.) executing on a network server is used to insulate clients (end users) at least somewhat from the profusion of interface command sets. Network software may do so by limiting clients to a series of network-supported operations.

In some aspects of the invention, network software controls the entire network. Network software may interact with and issue interface commands to connected devices through APIs designed for that network such as, through software that implements the APIs. In some aspects of the invention, specific APIs for each network software/device combination are utilized. The interface commands may be translated among and through various APIs. In some aspects of the invention, a generalized command set may aid communication among the networked devices.

The systems and methods of the invention integrate one or more pieces of laboratory equipment. In some aspects of the invention, the integration is performed at a Laboratory Information Management System (LIMS) or lower level. A computer system may run multiple pieces of laboratory equipment. Software and hardware for laboratory applications may be integrated using the methods and systems of the invention. In various aspects of the invention, similar components with shared functions are repeated in multiple pieces of laboratory equipment. Flexible linking of individual components, such as a camera with computer systems that drive and/or obtain data from such components are possible using the methods and systems of the invention Uses of LIMS in integrated laboratory systems are further described in U.S. Pat. No. 7,991,560, which is herein incorporated by reference in its entirety.

In some aspects of the invention, a common command interface (CCI) provides an interface abstraction allowing network device applications to maintain one set of code for each command regardless of which command interface (e.g., web, CLI, NMS, etc.) initiates the command.

Network devices including telecommunications and data communications equipment may be administered and/or controlled through a Command Line Interface (CLI) that provides the user (i.e., administrator) with a textual interface through which the administrator could type in commands. CLI connections can be made either directly with the device through a console or through a remote connection. Web interfaces may also allow administrators to remotely control network devices through web pages. In some cases, web interfaces may provide easier access with a more visually rich format through Hypertext Markup Language (HTML). For example, commands may be grouped and displayed according to particular categories and hyperlinks may be used to allow the administrator to jump between different web pages accessing a network comprising one or more laboratory instruments.

In some aspects of the invention, the preferences of a large number of users and advantages of various interfaces are accommodated by utilizing a variety of interfaces, for example, a CLI interface and a web interface provided to one or more network devices.

In some cases, the applications corresponding to the commands must include separate code for each interface. Applications running on a network device may maintain an API for each external interface. In some aspects of the invention, the source of each received command is tracked so that responses can be provided in the appropriate format, for example, HTML for a web interface or ASCII for a CLI.

In some aspects of the invention, a common command interface (CCI) provides an interface abstraction allowing network device applications to maintain one set of code for each command regardless of which command interface (e.g., web, CLI, NMS, etc.) initiates the command. Command codes in each application may be shared across multiple command interfaces. The interface abstraction allows new applications including additional commands to be added to a network device and existing applications to be dynamically upgraded to include new and/or modified commands without having to modify the CCI. Thus, the network device may provide the increased flexibility of having multiple command interfaces, while minimizing the complexity required to maintain commands across those interfaces. In addition, a community command interface may be used to connect the common command interfaces of multiple network devices. U.S. Patent Pub. No. 2003/0126195 describes uses of common command interfaces in further detail and is herein incorporated by reference in its entirety.

Connections within the Network

Various laboratory equipments in the system may be connected to a general purpose computer system via a short-distance connection bus, such as GPIB, SCSI and/or USB. The laboratory equipment may be any set of electronic devices with displays and/or control keys. Each item of hardware may be connected to the controlling computer. One or more standard personal computers may further be connected to the controlling computer. For example, the computer system may be equipped with a GPIB connector, for example, via a PCI expansion card.

The connection, such as a short-distance connection, between the laboratory equipment and the controlling computer and any networked computers to it may allow for the sending of control signals to the laboratory equipment and allow for the receiving of output from the laboratory equipment.

One or more computers in the system, such as the controller computer or any networked computers to it, may be connected to a computer network, for example an intranet or the Internet.

Use of Software, Network Stacks, and Layers

The computer system may be in communication with a remote computer system over a network. The connection may be a direct connection, for example, packets may be routed directly between the computer system and the remote computer system over the network or both the computer system and the remote computer system may execute a client application for contacting a server application that is also connected to the network. In this case, the server application may manage the communication between the two computer systems, for example, using a web service or a virtualized environment. In some aspects of the invention, the computer system is a general purpose computer system. In some aspects of the invention, the computer system may be a special-purpose digital device designed to manage the direct control of the laboratory equipment by the remote computer over the computer network. A special-purpose digital device may include a network adapter port such as an Ethernet port or wireless network adapter, a port for connecting to the laboratory equipment, for example, a GPIB port, and a microprocessor for executing various software layers. Various software layers may be executed by a special-purpose digital device for connecting laboratory equipment to a computer network. For example, a TCP/IP layer may be used to manage communication over the computer network by the sending and receiving of packets of data. The TCP/IP layer may be able to interpret the packets of data and pass along the interpreted information to a driver layer. The driver layer may then translate the data interpreted by the TCP/IP layer into equipment control and output signals. The driver layer may then send the equipment control and output signals to and from a GPIB layer which manages communication with the laboratory equipment.

In some aspects of the invention, the remote computer system is a general purpose computer system. A remote user may use a remote computer system to interface with the computer system across a network. The remote computer system may execute software for transferring data across the network. The software may include software for connecting to a virtual private network (VPN) or may include a client application for communicating with a remote server application over a virtualized environment.

In some aspects of the invention, the remote computer system is equipped to execute user interface software for presenting a virtual control laboratory equipment control panel to a remote user. In some aspects of the invention, for example where the computer system and the remote computer system communicate via a server over the virtual environment, the user interface software may be executed on the server, rather than, for example on the remote computer system.

A panel display for remote computer systems may be generated by a virtual panel application that may be executed either on the remote computer or on a server accessed by the remote computer. The virtual panel application may generate the panel display and ensure proper panel display function.

One or more computer systems or servers connected to the laboratory equipment of the invention may determine whether a remote command, for example a command delivered from a remote server or a virtual panel application, is being executed for the first time. Commands sent from remote locations may be sent multiple times. The execution of a particular command may be checked to avoid duplicate executions. In some aspects of the invention, a duplicate command is only executed, when it has not been previously executed. In this fashion, failures in prompt execution of remote commands, due to, for example, connectivity problems, can be smoothed within the network.

Operating systems and software applications used by general purpose computers may be subject to occasional software crashes and other unexpected terminations. Moreover, the network connection between the computer system and the remote computer system may occasionally fail. Accordingly, the possibility exists that the present state of one or more pieces of laboratory equipment may be lost upon a software crash. Each time a piece of laboratory equipment is turned on, or another critical setting is changed, the status of the laboratory equipment may be recorded to a configuration file. Then, as a remote command, for example, one from a virtual panel application, is executed, it may be determined whether the software has experienced a crash or whether the command has previously been executed. In some aspects of the invention, remote software may have access to a log of experienced crashes. Upon a re-execution attempt, the software access information related to shut down status, for example proper or crash shut-down during a previous execution attempt. Crash recovery protocols may be performed in cases where a crash has occurred. Crash recovery protocols may include reading a log/configuration file to determine status of one or more pieces units of laboratory equipment, for example whether they have been left powered on, left in the middle of an execution step or a longer protocol, for example an event loop, for that piece of laboratory equipment. In some aspects of the invention, a user may be prompted to shut down laboratory equipment left on or to take any other desired remedial steps.

In some aspects of the invention, the program may enter an event loop. The event loop entry may be contingent on information obtained from a log/configuration file, for example reporting the presence or absence of a recent crash or crash recovery has been performed. In some aspects of the invention, an event comprises a user making a change to one or more of the displayed settings related to a piece of laboratory equipment, for example as displayed on a panel display. The user may use a panel display to turn on a power supply, to start a cleaning cycle, to calibrate a pH meter or send any other suitable commands for operating the piece of laboratory equipment. In some aspects of the invention, an event comprises the occurrence of a read update. In an event loop, a determination may be made whether an event has occurred. When an event has occurred, the event may be parsed. Parsing of an event may include executing the instructions offered by the user. For example, where the event includes the user activating a power toggle for a unit of test equipment, commands for activating the unit of test equipment may be generated and transmitted to the test equipment via the network and the computer system.

In some aspects of the invention, an event is a read request. A read request may comprise a command sent to a piece of laboratory equipment requesting that one or more parameters be measured and sent back, such as for display on a panel display. For example, where the piece of laboratory equipment comprises a power supply, the read request may be to read a present voltage, current and power being drawn from the power supply. In another example, where the piece of laboratory equipment comprises a turbidity sensor, the read request may be to read a present turbidity level. Such an operation may be triggered either manually, for example, with a user selecting a read command, such as by using a read button on a panel display, it may be triggered at preset intervals, or it may be triggered upon execution of a predetermined list of commands. Thus, in various aspects of the invention, the event associated with a read request may be triggered by user input, the completion of certain events or the passage of a predetermined length of time.

In some aspects of the invention, a command may be interpreted as belonging to a category "not permitted". Commands of various categories, such as a "not permitted" category, may be automatically aborted. Users may be given different levels of permission. Permission levels may be determined by an administrator and may be stored in the system. In some aspects of the invention, a user may be presented with a dialog box regarding the user's permissions. In some aspects of the invention, a particular command or set of commands may be not permitted if execution of the commands, given the present state of the laboratory equipment, is likely to damage the equipment or cause other problems. Further examples for remote controls of laboratory equipment are discussed in U.S. Pat. No. 8,041,437, which is herein incorporated by reference in its entirety.

Device Interface Standards

Well established, commonly accepted device interface standards may be used to ease automation and integration of systems. In some aspects of the invention, the SiLA device interface standard may be used. Standards may focus on defining interfaces and protocols to interconnect any lab equipment to any control application, for example a SiLA enabled control application. In some aspects of the invention, devices can be controlled through a common command set, such as the SiLA common command set. Standards may be applied to custom systems. In some cases, standards may be incorporated to commercially available components of a system that can be obtained modularly from one or more suppliers.

In some aspects of the invention, a software wrapper may translate native device drivers into a standard command structure, such as a SiLA compatible command structure. Software wrappers may be implemented without changing the hardware.

In some aspects of the invention, interface converter hardware with specific protocol converter software is be connected to the native hardware interface, to encapsulate the device, providing high compatibility with standards, such as SiLA.

Data

The system allows for the analysis of biological data. To use the system a user will obtain a biological data set or multiple data sets. The data could be purchased or given to the user, but typically the user will be a scientist who performs a biological experiment which results in a data set. The data can be data which is extracted or outputted from software. For example the data can be a data file that is generated from a microarray experiment. For example the data can be a data file that is generated from a RNA sequence experiment (RNA-seq). For example the data can be a data file that is generated from a whole genome experiment or exome. For example the data can be a data file that is generated from quantitative real time polymerase chain reaction (qPCR) experiment, and/or in situ hybridization, cytogenetics or karyotyping, For example the data can be a data file that is generated from a whole proteomic genome experiment. For example the data can be a data file that is generated from mass spectrometry experiment. For example the data can be a data file that is generated from antibody-based experiment such a protein array, tissue microarray, 2D gel analysis, flow cytometry and/or ELISA.

The system can in some embodiments accept data from multiple sources, for example from multiple users or across multiple experiments. In various aspects of the invention, the content of the data set comprises data related to gene expression, genotyping, sequencing, single nucleotide polymorphism, copy number variation, gene or proteins isoforms, haplotyping, genomic structure, protein expression, protein modification, protein-protein interaction, protein localization or drug response. The data sets can be related to diagnostics or clinical data or the data sets can be generated for basic scientific research.

The system can use data entirely supplied by the user, but in preferred embodiments the system additionally includes data from sources other than the user. The system can then allow the user to determine how the user provided data is related to the data from other sources, and/or how the user supplied data is related to itself in light of the data from other sources. In various aspects of the invention, the content of the data supplied by someone other than the user comprises data related to gene expression, genotyping, sequencing, single nucleotide polymorphism status, methylation status, copy number variation, haplotyping, genomic structure, protein expression, protein modification, protein-protein interaction, protein localization or drug response. The data sets can be related to diagnostics or clinical data or the data sets can be generated from basic scientific research. In some embodiments the data supplied by someone other than the user comprises information extracted either manually or automatically from scientific articles, books, literature, websites, webcasts, blogs, podcasts, or other similarly published sources.

The system can use a structured database to organize the data. In some embodiments the system comprises an ontological database. In some aspects of the invention, an ontological database in the data analysis package comprises organized information related to the biological content of the data set. Methods and systems related to ontological databases are described in PCT/US07/74663, 60/820,773, 60/725,949, 60/725,948, 60/725,936, 60/725,931, 60/725,898, 60/725,895, 60/725,890, 60/725,889, 60/725,888, 60/725,887, 60/725,766, 60/725,737, 60/725,734, 60/725,732, 60/725,676, 60/647,301, 60/618,082, 60/617,990, 60/617,987, 60/617,980, 60/617,967, 60/617,966, 60/617,932, 60/617,913, 60/617,908, 60/617,850, 60/617,828, 60/617,811, 60/617,799, 60/617,788, 60/617,730, Ser. Nos. 13/029,089, 11/829,784, 10/864,163, 10/802,615, 10/770,864, 10/632,099, 10/502,420 which are herein incorporated by reference.

Providing the Data to the System/Accessing the System

The user will provide data to the system in order to analyze or otherwise interpret the data. The data can be uploaded to a local computer running software or the uploading can occur over a network. There can be a combination of both local software and a network or "cloud" based aspect of the system which allows the user to provide the data. In some instances the providing of the data is merely the user allowing the system access to the biological data wherever it is already located, for example the user may allow the system to access a hard drive already containing the data.

The user may repeatedly provide data to the system. In some aspects of the invention, the data is on a computer readable medium, which is provided to the system. For instance the user might buy software which would allow the user to analyze a new dataset at the user's convenience with or without access to a network. Alternatively, the user may be accesses the analysis tools via a network. For instance the user may obtain a password which allows access to the analysis tools over a network. In another embodiment, the user stores data on computer readable media that is operatively linked to the system. The linking can be permitting access to the system.

In one embodiment, the user's ability to provide data to the system is enabled when the user purchases a component necessary for generating the data. For example, the user may be given a code for accessing the system over a network when the user purchases a microarray. In some aspects of the invention, such a transaction comprises the purchase of one or more product(s) or service(s) for the generation of one or more data set(s). Permission to access the data analysis package is optionally provided in a manner that is linked to the transaction. In some aspects of the invention, the access to the data analysis package comprises an access code or partial code. In some aspects of the invention, access is given to the entirety of the data analysis package. In some aspects of the invention, partial access is provided to specific portions of the analysis package. The data set is generated using the product or service purchased at the first transaction. In some aspects of the invention, the data collection is at least partially performed by the user. In some aspects of the invention, the data set is shared with the core lab. In some aspects of the invention, the data collection is performed at least partially by a core lab. In some aspects of the invention, the data set is shared with the user. In some aspects of the invention, the first transaction is between the user and the core lab. In some aspects of the invention, the data set is entered into the data analysis package after the data collection. In some aspects of the invention, the data set is entered into the data analysis package during the data collection. In some aspects of the invention, the data is entered to the system by the core lab. In some aspects of the invention, the system provides an output to the core lab. In some aspects of the invention, the system provides and output to the user. In some embodiments an option to purchase an access to the analysis package is communicated to the user after the first transaction. In some aspects of the invention, a second transaction comprises purchasing permission to gain access or partial access to the analysis package. In some aspects of the invention, the first and the second transactions are independent events.

In some embodiments of the invention, the data analysis package accepts one or more user provided data sets in various formats as an input. In some aspects of the invention, the data set comprises unprocessed/raw data from an experiment. In various aspects of the invention, the user provided data set is a biological data set.

In FIG. 1 a flow diagram of one embodiment of a system constructed in accordance with the present invention is illustrated. The system is designated generally by the reference numeral 100. The system 100 provides a method for bundling the transaction for gaining access to a data analysis package with a transaction for a product or service that is used to generate a data set to be entered into the data analysis package for analysis. The flow diagram illustrating system 100 shows a product or service transaction or discounted transaction 102 and an access or partial access transaction or discounted transaction 103 for the use of the data analysis package. The transaction 102 and 103 are either offered as a selection or a single transaction option including both 102 and 103 is offered. In some aspects of the invention, a price or value is associated with the combined transaction is lower than the sum of two prices or values associated with the individual transactions 102 and 103. In some aspects of the invention, the price value associated with transaction 102 is zero. In some aspects of the invention, the price value associated with transaction 103 is zero. The system 100 includes a product or service 110, which is purchased during the transaction 102. One or more data sets 111 are generated using the product or service 110. An access or partial access to the data analysis package 120 is purchased during the transaction 103. The access or partial access 120 grants permission to use the data analysis package under specified terms. In some aspects of the invention, the transaction 102 grants the purchase of a plurality of products or services 110. In some aspects of the invention, the transaction 103 grants the purchase of a repeated access or partial access to the data analysis package. In some aspects of the invention, the number of products or services 110 and the number of accesses or partial accesses 120 are linked. In some aspects of the invention, the access or partial access 120 is granted for a specific time period or a specific amount of time.

The system 100 facilitates the generation of data 111 using the product or service 110. The access or partial access 120 permits the entry of the data 111 into the data analysis package. A first analysis 130 is performed using the data analysis package. The system 100 offers one or more supplementary transactions 140. An enhanced access or partial access to the data analysis package 150 is purchased during the supplementary transaction 140. In some aspects of the invention, the supplementary transaction 140 is adjusted for an enhanced partial access 150 to specific parts or functionalities of the data analysis package. An enhanced analysis 160 is performed using the parts and functionalities of the data analysis package purchased during the transaction 150.

In some embodiments an enhanced access or partial access transaction 140 is bundled in an initial transaction 101.

In some aspects of the invention, an access or partial access to the data analysis package is given through a user registration for the product or service 101. In some embodiments an access or partial access to the data analysis package is given to a core lab. In some aspects of the invention, the core lab performs all or part of the experiments associated with the product or service 110. In some aspects of the invention, the core lab performs the data analysis.

In some aspects of the invention, a user registration for the product or service 101 comprises an e-mail address and a password. In some aspects of the invention, the password comprises alphanumeric characters. In some aspects of the invention, the password comprises all printable characters. In various aspects of the invention, the password is 1, 2, 3, 4, 5, 6, 7, 8, 9, 10, 11, 12, 13, 14, 15, 16, 17, 18, 19, 20 characters long or longer.

In some aspects of the invention, a right to access parts or all of the data analysis package is provided on a one-time or multiple-time basis. In some aspects of the invention, the right to access is limited within a time period. In some aspects of the invention, the right to access parts the entire data analysis package is provided with the product or service 110. In some embodiments a code or serial number accompanies the product or service 110, which can be used to gain partial or full access to the data analysis package. In some aspects of the invention, the code or serial number accompanying the product or service 101 codifies the type of product or service 101 to the data analysis package.

In some aspects of the invention, a computer readable access recognition software recognizes a user. Accordingly, the system grants access to users who have a right to access. In some aspects of the invention, the access recognition software is installed in the user's computer. In some aspects of the invention, the access recognition software is installed remotely. In some aspects of the invention, the access recognition is informed by the user's purchase of a service or product. In various aspects of the invention, the service or product is used to generate a data set that the user analyzes using the data analysis package. In some aspects of the invention, the recognition is based on recognizing a user's computer. In some aspects of the invention, the recognition is based on recognizing a registered e-mail address, IP address, or software (e.g. cookie) stored on the user's computer.

In various aspects of the invention, the product or service 110 is equipped to generate biological data and the generated data 111 comprises a biological data set.

Typed of Databases

The process to populate a frame-based knowledge representation system (herein "KRS") with information, leading to the creation of what is called a "knowledge base," ("KB") is known as knowledge acquisition (KA).

A first embodiment comprises a method for deconstructing experimental findings originally occurring in narrative text or symbolic (e.g., graphical or tabular) documents, structuring and codifying these findings by means of templates and then storing the information contained in the completed templates in a KRS to create a KB.

The data architecture used in this embodiment is herein referred to as an ontology. An ontology is a hierarchical representation of the taxonomy and formal concepts and relationships relevant to the domain of interest stored in a knowledge representation system ("KRS"). In short, ontology is a specific form of a KRS. The KRS may be a frame-based, rule-based or other type of database architecture, the choice of which may depend on a variety of factors, such as storage needs. In one embodiment, a frame-based KRS is used. Therefore, for purposes of describing the KRS of one embodiment, reference will be made to a frame-based KRS. However, it should be understood that other known types of data architecture may alternatively be used in connection with some embodiments, as will become apparent. In a first embodiment, the domain of interest is genomic information, which comprises at a minimum information relating to genes, their DNA sequences, the proteins which result when the genes are expressed, the biological effects of the expressed proteins and other, related information. Using an ontology allows searching to find relationships between and inferences about the items stored in the KB.

In order to accomplish these goals, the ontology must be formally defined and organized. The primary organizational component of the ontology in a frame-based KRS is the class. Classes are descriptions of particular categories of objects. Properties are attributes that describe the class itself or relate one class to another. An instance is an actual example of a class, and the relationship between two different instances in the ontology is defined by slots. Slots can be thought of as the verbs that relate and link two classes. Once information is represented in this manner, frame-based KRSs support basic inference capabilities such as classification and declarations of axioms. Axioms impose semantic constraints on the ontology that help to maintain the consistency and integrity of the data. Frame-based KRSs also provide basic query capabilities for retrieving stored data. Populating the frame-based KRS with real world examples of experimental information transforms the system into a KB.

Data Analysis

Once the user provides a data set, a graphical user interface is provided for a user to interact with the system. In some aspects of the invention, the graphical interface is equipped for entering one or more data sets. In some aspects of the invention, a data set is entered using the graphical user interface. Generally the user provides data to the system which can analyze the data. The system can comprise information in addition to the data set, which allow for the analysis and interpretation of the user provided data. One skilled in the art will recognize that the system may, in some aspects of the invention, not contain all of the additional information, but may have access to the information stored elsewhere. In some embodiments the system will search for related information de novo each time a data set is provided by a user.

Relating the user data to additional information is facilitated by a structured database, for example an ontological database, knowledge representation system or knowledge base. The databases can be contained in the system or may be accessed by the system. The database can comprise information obtained from public or private sources. The information can be added to the database by human reviewers or by automated mechanisms.

In some aspects of the invention, the graphical interface is equipped generating a report of the user supplied data with information contained in the data base using various colored shapes to visually indicate to the user specific biological attributes or features related to the data. The graphical user interface can use various aspects of color appearance for example, color hue, color saturation or color brightness.

Color hue is one of the main properties of a color. A hue is an element of the color wheel. In painting color theory, a hue refers to a "pure color" that is one that contains no tint or shade such as added white or black pigment, respectively.

Color hue is generally defined as the "the degree to which a stimulus can be described as similar to or different from stimuli that are described as red, green, blue, and yellow". For example, colors with the same hue are distinguished with adjectives referring to their lightness and/or chroma, such as with "light blue", "pastel blue", or "vivid blue". Color hue can also be defined is technical terms as provide by the CIECAM02 model.

Color saturation is the colorfulness of a color relative to its own brightness. The saturation of a color is determined by a combination of light intensity and how much it is distributed across the spectrum of different wavelengths. The most saturated color is achieved by using just one wavelength at a high intensity, such as in laser light. To desaturate a color of given intensity one can add white, black, gray, or the hue's complement. Saturation is one of three coordinates in the HSL and HSV color spaces. Note that virtually all computer software implementing these spaces use a very rough approximation to calculate the value they call "saturation", such as the formula described for HSV.

Color lightness is a property of a color that is defined in a way to reflect the subjective brightness perception of a color for humans. Perceived color brightness changes along a lightness-darkness axis.

Figure 2:
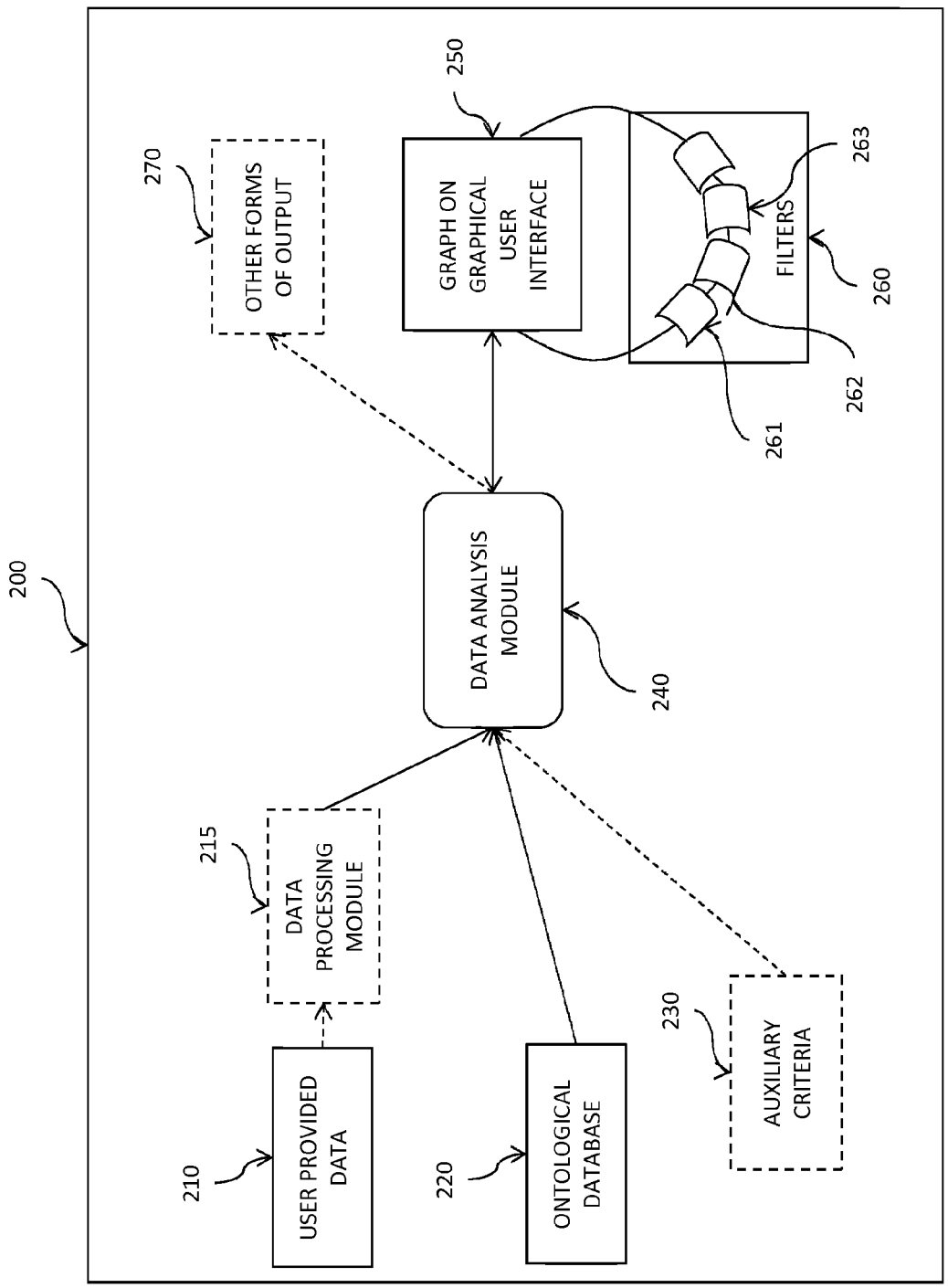
FIG. 2 depicts an embodiment of the system to illustrate the relationship between the user provided data, the data analysis module, and the interactive filters and graphs of the graphical user interface.

Referring now to FIG. 2, a flow diagram of another embodiment of a system constructed in accordance with the present invention is illustrated. The system is designated generally by the reference numeral 200. The system 200 provides a method for the analysis of a user provided data set 210 on a data analysis package relating the data set to information obtained from a database 220. For example data obtained from a gene expression study can be the provided to the data analysis module to analyze relationships between these data with respect to a database comprising facts and relationships between those facts obtained independently of the data. The data analysis package comprises a data analysis module 240 that takes as input the user provided data set 210, accesses a database 220 for additional input and uses an algorithm to generate an output in the form of a graph 250 on a graphical user interface. The system 200 further comprises methods to interact with the graphical output. A plurality of filters 260, individually outlined in blocks 261, 262 and 263 are available facilitating the analysis and preferred visualization of the data. In some aspects of the invention, the filters 260 are accessed through the graphical user interface. In some aspects of the invention, a script provides instructions on the usage of the filters 260.

In various embodiments of the invention, the data analysis package accepts as input, user provided data sets 210 of varying content. In some aspects of the invention, the user provided data set 210 comprises data with biological content. In some aspects of the invention, the database 220 in the data analysis package comprises organized information related to the biological content of the data set. In various aspects of the invention, the content of the data set comprises gene expression, genotyping, sequencing, RNA sequencing, single nucleotide polymorphism, copy number variation, isoforms, haplotyping, genomic structure, protein expression, protein modification, protein-protein interaction, protein localization or drug response.

The database 220 facilitates the relation of features and one or more data contents comprised in a data set. In some aspects of the invention, the user provided data set 210 comprises one or more biological contents. In some aspects of the invention, the features comprise biological properties. In various embodiments the biological properties comprise biological pathways, biological processes, biological or chemical functions, cellular locations, phenotypes, associations with diseases or disease states, locations within a genome, co-expression profiles, co-localization profiles, associations with tissues, associations with developmental stages and networks. In some embodiments the database can be comprised of information extracted from multiple published sources.

In various aspects of the invention, the data set is represented on a graph on the user interface comprising icons linked to members/data points of the data set. In some aspects of the invention, the graph further comprises icons that are linked to additional features. In some aspects of the invention, the features are filtered down to a subset of features, which are related to the data set. In some aspects of the invention, the features are biological properties. In some aspects of the invention, the features related to the data set will be obtained from the ontological database. In some aspects of the invention, the data set is biological and the database relates members/data points of the biological data set to the biological properties.

The plurality of filters 260 provide methods to filter features obtained from the database 220 down to a subset. In some aspects of the invention, the software analysis package applies a filter on the features based on the content of the data set. In some aspects of the invention, the software analysis package applies a filter on the features based on the particular constitution of the data set. Individual data points/members of the data set are analyzed by the software analysis package to determine the particular constitution of the data set. Accordingly, a filter may be applied on the set of features, the data set or both, based on the constitution of the data set. In some aspects of the invention, a filter is applied based on instructions from a script. In some aspects of the invention, the features comprise biological properties and the data set comprises one or more types of biological content.

In some aspects of the invention, the plurality of filters 260 provide methods to filter the members/data points of the user provided data set 210 down to a subset. In some aspects of the invention, the software analysis package applies a filter on the members/data points of the user provided data set 210 based on a selected set of features. In some aspects of the invention, a filter is applied based on instructions from a script. In some aspects of the invention, the features comprise biological properties and the data set comprises one or more types of biological content.

In various aspects of the invention, a plurality of different types of filters are applied in combination and the graph reflects the results of the filter combinations. In some aspects of the invention, the set of selectable icons are updated based on the set of active filters.

In some embodiments of the invention, the data analysis package accepts one or more user provided data sets 210 in various formats as an input. In some aspects of the invention, the user provided data set 210 comprises unprocessed/raw data from an experiment.

In some aspects of the invention, the system 200 comprises a set of data processing module(s) 215. One or more data processing modules, individually illustrated in blocks 216, 217 and 217 facilitate the entry of the user provided data set 210 into the data analysis package. In some aspects of the invention, the set of data processing modules 215 performs a statistical analysis of the user provided data 210. The statistical analysis comprises, by way of example, analyses calculating statistical parameters comprising a mean, standard deviation, skewness or any mathematical moment for the user provided data set 210 or a portion thereof. The statistical analyses may relate to comparative analysis between a plurality of user provided data sets 210 or between portions of the user provided data set 210. In some aspects of the invention, new values are assigned to members/data points in the user provided data set 210 as a function of the calculated statistical parameters. In some embodiments the data set is normalized 210. In some aspects of the invention, a first processing module 216 provides an output in a different format than the input. In some aspects of the invention, a processing module 217 or another module in the data analysis package is equipped to accept the output from the first processing module 216.

In some aspects of the invention, the system 200 further accepts as input one or more auxiliary user criteria 230 as auxiliary input. In some aspects of the invention, the system comprises an algorithm to interpret the contents of the auxiliary input. In some aspects of the invention, the auxiliary input is entered in plain text. In some aspects of the invention, the auxiliary input is processed by natural language processing. In some aspects of the invention, the content of the auxiliary input is considered by a scoring algorithm in association with the user provided data set and the features associated with the data set to bias the display of the most relevant pieces of information. In some aspects of the invention, one or more features are preferentially displayed. In some aspects of the invention, a filter is applied to the data set or the features associated with the data set based on the auxiliary information. In some aspects of the invention, the data set is a biological data set and the auxiliary input comprises user criteria including the specific design of the experiment that was performed to generate the data set or the purpose or focus of the study.

In some aspects of the invention, the system generates other formats of output 270. The additional formats of output 270 facilitates the use of the data analysis results in other modules or systems. In some aspects of the invention, the user exports the output in a computer readable format from the system.

Figure 3:
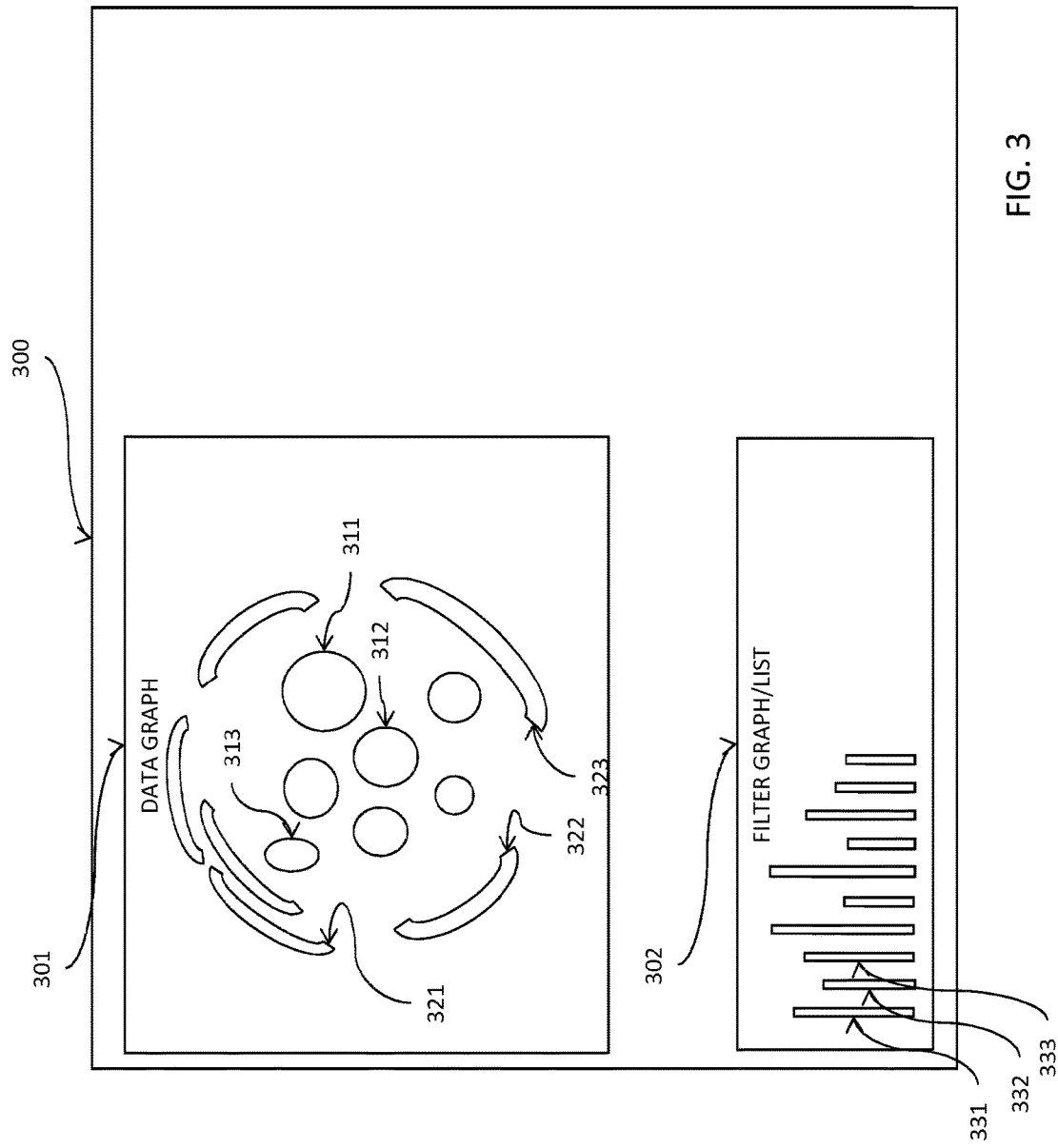
FIG. 3 depicts an embodiment of the system illustrating the use of a data analysis package for visualizing user provided data set refined by information from an ontological database on a graphical user interface.

Referring now to FIG. 3, a diagram of another embodiment of a system constructed in accordance with the present invention is illustrated. The system is designated generally by the reference numeral 300. The system 300 provides a graphical user interface. The graphical user interface can be on a screen, can be projected, and can be displayed in one, two or three dimensions. The graphical user interface comprises one or more data graphs 301 for the display of a user provided data set. The data graph 301 comprises one or more data icons, individually illustrated in blocks 311, 312, and 313. The data icons 311, 312, and 313 are linked to and represent members/data points of the user provided data set. The data graph 301 further comprises one or more feature icons, individually illustrated in blocks 321, 322, and 323. The feature icons 321, 322, and 323 are linked to features that are obtained from an ontological database. In some aspects of the invention, the features are filtered down to a subset of features, which are related to the data set. In some aspects of the invention, the features are biological properties. In some aspects of the invention, the user provided data set is biological and the database relates members/data points of the biological data set to the biological properties. In some aspects of the invention, the database relates features and one or more data contents comprised in a data set. In various embodiments the biological properties comprise biological pathways, biological processes, biological or chemical functions, cellular locations, phenotypes, associations with diseases or disease states, locations within a genome, co-expression profiles, co-localization profiles, associations with tissues, associations with developmental stages and networks.

In various embodiments of the invention, the data analysis package accepts as input, user provided data sets of varying content. In some aspects of the invention, the database in the data analysis package comprises organized information related to the biological content of the data set. In various aspects of the invention, the content of the data set comprises gene expression, genotyping, sequencing, single nucleotide polymorphism, copy number variation, haplotyping, genomic structure, protein expression, protein modification, protein-protein interaction, protein localization or drug response.

The data graph 301 comprises the data icons 311, 312, and 313, the feature icons 321, 322, and 323 and at least one visual metric associated with the data icons 311, 312, and 313 to visualize a data set on a graphical user interface. In some aspects of the invention, the data graph further comprises at least one visual metric associated with the feature icons 321, 322, and 323. The icons on the interface are displayed in a fashion to convey information about one or more attributes related to the data set. A preferred attribute to be represented visually on an icon is a value associated with the measurements in the user provided data set. Other attributes comprise the degree of association with one or more features. In some aspects of the invention, the feature icons 321, 322, and 323 are filtered down to a subset of features based on the content of the data set. In some aspects of the invention, the features are biological properties.

One or more visual metrics associated with the icons facilitate the visualization of the user provided data set on the data graph 301. The icons on the interface are displayed in a fashion to convey information about one or more attributes related to the data set and the attributes obtained from an ontological database. A visual metric marks an icon to designate a distinguishable identity to the icon. Various embodiments of the invention use one or more visual metrics to mark an icon or a portion of an icon. By way of example, the portion of an icon comprises one or more edges, corners, areas and lines within. In some embodiments one or more shapes, colors, color hues or shadowing applications are used as visual metrics. Various embodiments use one or more dimensions associated with an icon or a portion of an icon as a visual metric. Other uses of visual metrics marking an icon include, by way of example, the location of the icon in the data graph 301. In various aspects of the invention, particular locations on the data graph 301 are designated to icons with particular attribute values. In some aspects of the invention, the designated locations associated with particular attribute values are recognized, but change their absolute positions on the graph. In various aspects of the invention, further visual metrics are used to recognize the identity of the attribute associated with designated locations. In some embodiments a distance from one or more designated locations on the data graph 301 is used as a visual metric. In some embodiments icon to icon distance is used as a visual metric. Various embodiments group/cluster icons. Icons within a group are optionally individually linked to other icons. Methods of linking icons include, by way of example, drawing a line, an arrow or another connecting object between or passing through the icons. In some aspects of the invention, the connecting objects are marked with one or more visual metrics identifying a value for the linking attribute. Linking attributes include, by way of example, participation in a biological pathway or cellular process, biological location, association with a disease, possession of a specific function or structure or the quantity or quantities thereof. In some aspects of the invention, the connecting objects have directionality. In some aspects of the invention, one or more pieces of text are used as a visual metric/identifier. In some aspects of the invention, a specific motion of an icon or part of an icon is used to construct a visual metric. For example, an icon can vibrate at a certain frequency and the amplitude. The frequency and the amplitude of the movement can be used as visual metrics.

The data graph 301 allows users to interact with the data analysis package to analyze the data set. In various embodiments one or more icons can be selected by a computer mediated interaction with the graph. Computer mediated interactions, by way of example, comprise inputs through a computer mouse, a computer keyboard, various peripheral computer devices, a script, a camera, for example receiving eye movements or gestures or an input device, for example receiving voice commands. In some embodiments an icon is selected by hovering a cursor on the display over or in the vicinity of the icon. In some aspects of the invention, one or more visual metrics associated with the icon display a change when the icon is selected. In some aspects of the invention, a piece of information related to the icon is displayed upon the selection of the icon. In various aspects of the invention, the selection comprises clicking/activating a computer mouse while the cursor controlled by the computer mouse is on or in the vicinity of the icon. In most embodiments, the cursor is considered to be in the vicinity of an object, when the object is close enough to be at least the closest selectable object to the cursor. In some aspects of the invention, a plurality of icons is selected based on combined input from peripheral computer input devices or a script.

The data graph 301 facilitates enhanced visualization of the user provided data set by allowing only a filtered subset of features to be represented by feature icons 321, 322, and 323 on the data graph. In some aspects of the invention, the software analysis package applies a filter on the features based on the content of the data set. In some aspects of the invention, the software analysis package applies a filter on the features based on the particular constitution of the data set. Individual data points/members of the data set are analyzed by the software analysis package to determine the particular constitution of the data set. In some aspects of the invention, a filter is applied upon one of the various methods of icon selection. In some aspects of the invention, a filter is applied based on instructions from a script. In some aspects of the invention, the features comprise biological properties and the data set comprises one or more types of biological content.

The data graph 301 facilitates enhanced visualization of the user provided data set by allowing a filtered subset of members/data points to be represented by data icons 311, 312, and 313 on the data graph. In some aspects of the invention, a filter is applied upon one of the various methods of icon selection. In some aspects of the invention, a filter is applied based on instructions from a script. In some aspects of the invention, a filter on the members/data points is applied based on the selection of icons representing the members/data points. In various aspects of the invention, a filter on the members/data points is applied based on the selection of icons representing the features obtained from the ontological database. In some aspects of the invention, the features comprise biological properties and the data set comprises one or more types of biological content.

In various aspects of the invention, a plurality of different types of filters are applied in combination and the graph reflects the results of the filter combinations. In some aspects of the invention, the set of selectable icons are updated based on the set of active filters.

The system 300 can further provide a filter history panel FIG. 3, 302. The filter history panel 302 comprises a graph or list of the filters applied during the analysis. The filters are optionally represented by filter icons, individually illustrated by blocks 331, 332, and 333. The application of various filters during the analysis is recorded by the software analysis package. In some aspects of the invention, the recording is a chronological recording. In some aspects of the invention, the list or the graph of filters is chronological. The history panel 302 allows for the selection of one or more filter icons 331, 332, and 333 by any means of computer mediated user interaction. Various methods of icon selection are discussed supra.

Chronological display of filter applications allow for a historical representation of user interactions with the data analysis package. In some aspects of the invention, one or more filter icons 331, 332, and 333 are marked by a visual metric. Various types of visual metrics and methods of marking an icon with a visual metric are discussed supra. In some aspects of the invention, a visual metric associated with an icon identifies an attributed related to the filter represented by the icon. In some aspects of the invention, the filter attribute relates to the number of the data icons 311, 312, and 313 or feature icons 321, 322, and 323 eliminated by the filter. In various aspects of the invention, a filter icon 331, 332, and 333 in a chronological filter application list or graph is selected to remove one or more filters. In some aspects of the invention, a plurality of filter icons is selected 331, 332, and 333. In some aspects of the invention, the filter associated with the selected icon is removed. In some aspects of the invention, the filter or filters following the selected icon are removed. Other rules for managing the filters represented by the icons based on the one or more selected icons are possible and will be obvious to the person having ordinary skill in the art.

The system is a graphical user interface facilitating the analysis and visualization of a biological data set. The system is designated generally by modules. Modules comprising the system can include but are not limited to 501, 601, 701, 801, 901, 1001, 1101, 1201, 1300, 1400, 1500 and 1600. Referring to FIG. 4(B), several optional modules of system are illustrated. The graphical user interface is illustrated with a user provided biological data set already entered into the system.

The system can be accessed through a login process using an access code provided to a user, e.g., "Daryl Michalik", which is displayed in the username field. The user can leave the system by selecting the logout icon. A training feature for system use can be accessed by selecting an icon. A text entry field is provided to do searches in the system. The search query can be activated by several computer mediated user interaction methods, such as hitting an "enter" or "return" key on a computer keyboard linked to the system. Alternatively, a dedicated query icon is also provided for a user to initiate a text based search query.

Figure 4A:
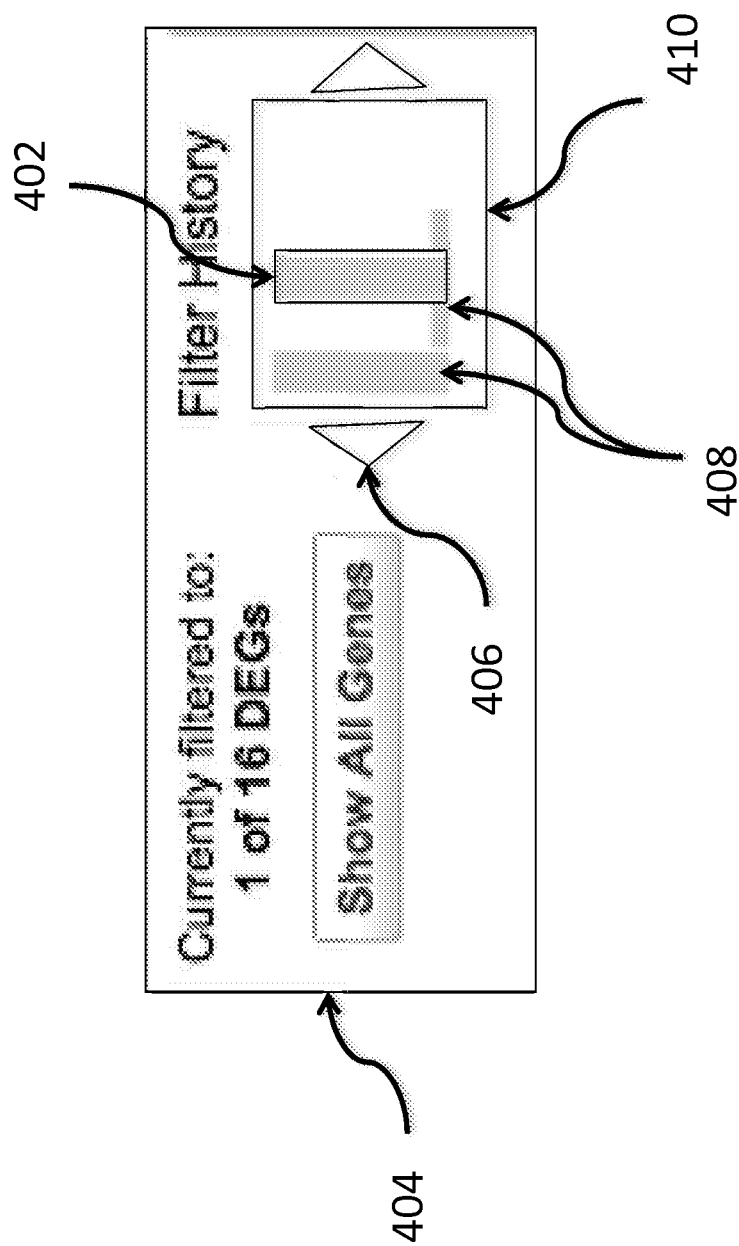
FIG. 4(A) depicts an embodiment of "Filter History" module illustrating the graphical user interface 404.
Figure 4B:
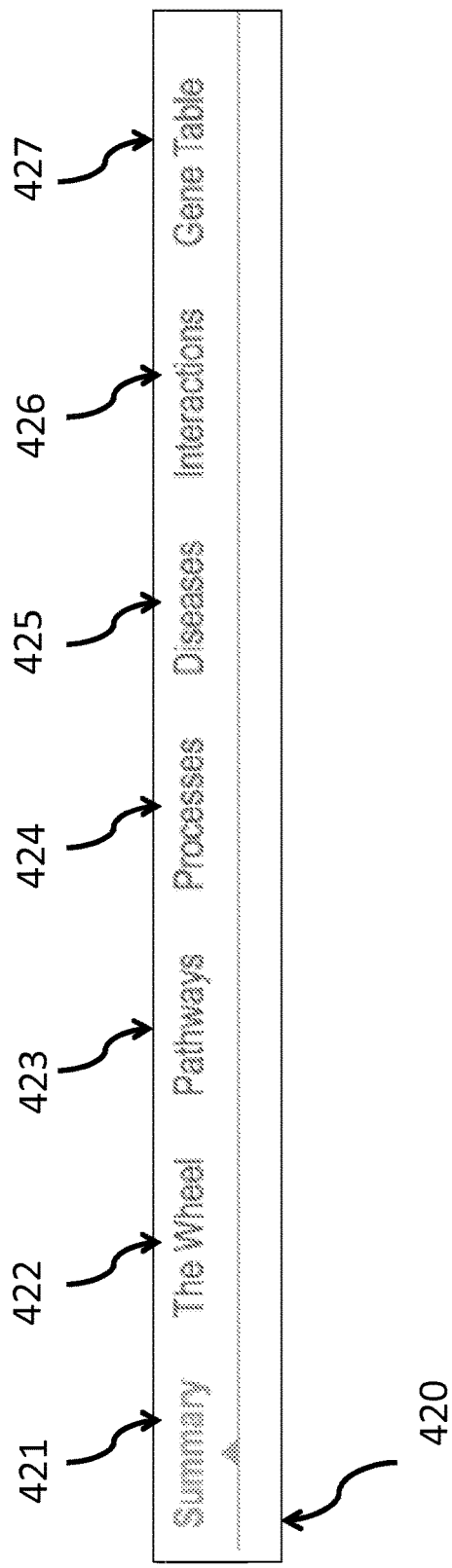
FIG. 4(B) depicts an embodiment of the system illustrating the graphical user interface to navigate to each module "Summary", "The Wheel", "Pathways", "Processes", "Diseases", "Interactions" and "Gene Table"
Figure 5A:
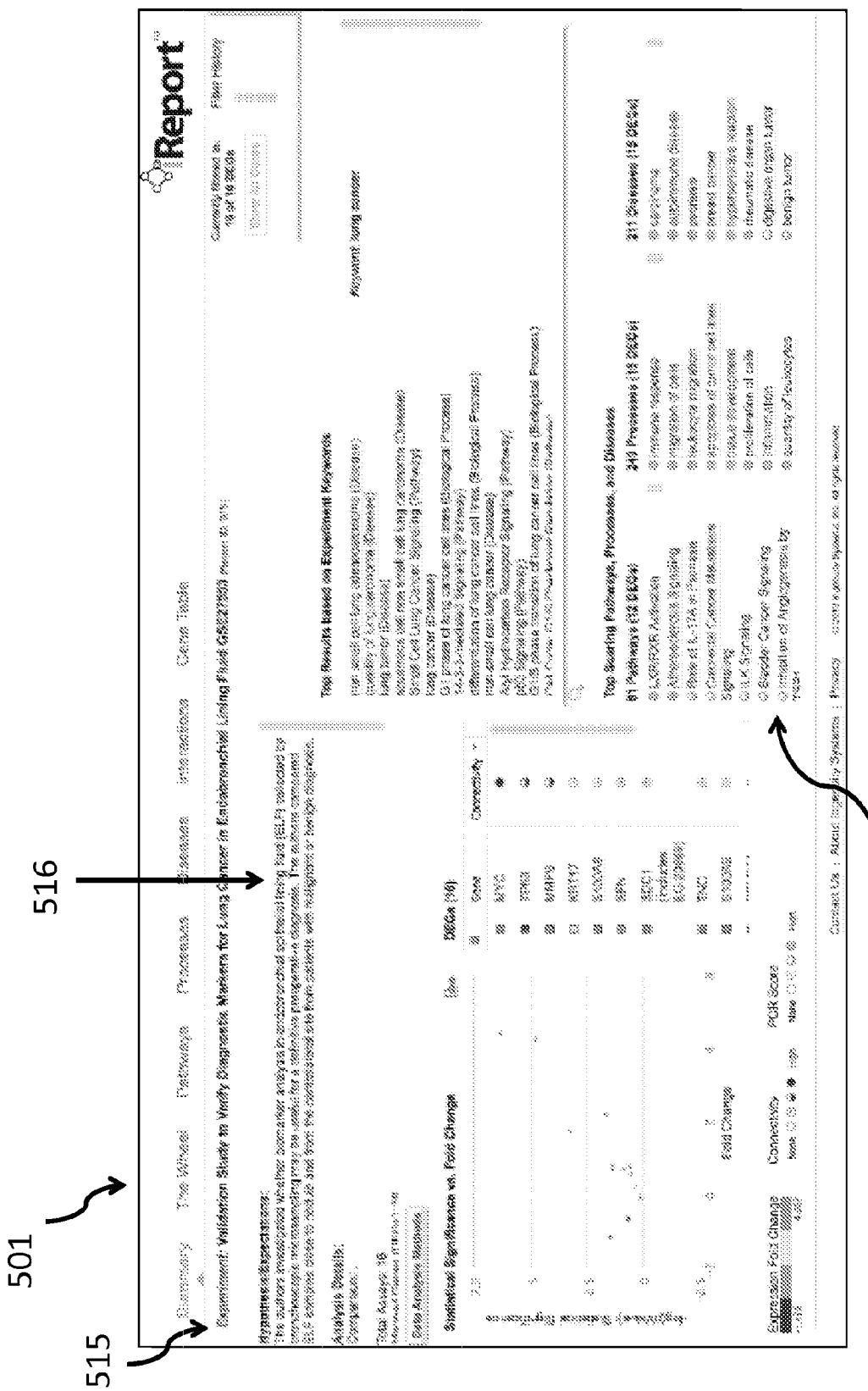
FIG. 5(A) depicts an embodiment of the system illustrating the graphical user interface being accessed by a user in a "Summary" view 501.

The system provides a user access to several optional modules for data visualization and analysis FIG. 4(B), 420. The different modules can be accessed under different views in the graphical user interface. The view selection icons 421, 422, 423, 424, 425, 426 and 427 are arranged in a view selection icon area 420 on the user interface. FIG. 5(A) displays a "Summary" view 501, which can be accessed by selecting the view selection icon 421. By way of example, a "Gene Wheel" view 601, illustrated in can be accessed by selecting the view selection icon 422, a "Pathways" view 701, can be accessed by selecting the view selection icon 423 and so on. In various aspects of the invention, the view selection icons are provided in multiple and optionally all views. Therefore, a plurality of links connect various views to each other through the selection of the appropriate view selection icons 420.

The "Summary" view 501 comprises several optional fields for the visualization and analysis of user provided data. The graphical display summarizes the data that was previously provided by the user. The input area encompasses several optional fields displaying user provided information. A user provided experiment title is displayed in an experiment title field 515, and a user provided experiment summary is displayed in an experimental summary field 516. A study design field is also optionally provided, where additional user provided auxiliary information can be displayed. The auxiliary information may comprise information about the data set, the experimental design, and the study focus.

The graphical display may include a summary graph 530. In a particular example, the user provided data set comprises gene expression levels of various genes and individual data points include the identity of a particular gene and a quantity associated with the expression level of the gene. The data is processed and converted from acquired numbers to a fold change format as displayed in a summary graph. Combined experimental observations accumulate information about distributions governing observables in an experiment. A database linked to system can be quarried to compare values for an observable with a distribution that is modeled after previous observations of the value of an observable. The value of an observable in a system may have larger or smaller fluctuations as determined by previous observations, which are compiled in the ontological database. Thus, a certain amount of change may be more significant for the values of some observables compared to others. The summary graph 530 is equipped to display this information for the user to have an informed understanding of the provided data set. A statistical analysis allows users to be informed about the significance of the values in a particular data set in view of such a distribution. Statistical methods to infer such significance values are known to ones skilled in the art. In this particular example, the individual data points are plotted in the summary graph 530, comprising a fold change value on a horizontal axis and a statistical significance associated with observing the fold change value for that particular gene on a vertical axis. The data points can be displayed as individual data icons. Color can be used as a visual metric displaying the expression fold change level for each gene. Optionally, a legend box 518, summarizes the use of visual metrics in icons. The legend box 518 includes a legend, that uses colors used as visual metrics associated with various types of icons to values they represent 519. In various aspects of the invention, the range of the represented values is a property of the user provided data set. In particular embodiments, the legend 519 maps corresponding colors for different expression fold change levels. The mapping of the colors to values within that range is optionally adjusted dynamically to display the various values with higher sensitivity. In some aspects of the invention, other visual metrics (e.g. data icon size) are also dynamically adjusted to map the range of values associated with the user provided data set. A second legend 520 maps a second visual metric to a second set of values. In this particular example, the icon fill-in style is representative of a value displayed on various icons on the "Summary" view 520. The mapping of visual metrics to value ranges can be linear, exponential, logarithmic or follow any function that is suitable for the visualization of a value. The layout and content of the summary graph 530 may have variations, which will be obvious to ones skilled in the art. The isoform icons, for example 544, can be presented as a visual icon and can include a visual metric showing the number of specific isoform annotations.

A table 540 lists information related to individual data points/members of the user provided data set. In this particular example, the user provided data set displays statically significant genes by, expression fold change 542, isoforms specific annotations 544, and connectivity rank 543. The table lists gene names 541 and a second set of data icons indicating level of differential gene expression by color 542. The color of the data icons 542 is informed by processed gene expression data following the mapping of the legend 519. Connectivity icons 543 follow the mapping of the legend 520 using fill in representation as a visual metric to the degree of connectivity a gene has. Connectivity icons 543 can be accessed and activating it opens the "Gene Table" module to the respective gene it is linked to. Methods to sort the table 540 are by level of differential gene expression (DEG), gene name and degree of connectivity are provide by clicking on the icons 542, 541, and 543, 544 respectively. Optionally, the table is sorted according to the information contained in a column, by selecting the title of the column for example the title of 542, 541 and 543.

In various aspects of the invention, the data analysis package processes the input from the user to generate keywords. In some aspects of the invention, the user input comprises information from the experiment title field 515, the experiment summary field 516, and study design field. Optionally, the generated keywords are displayed in a keyword list 575. In some aspects of the invention, the data analysis package quarries a database with the generated keywords to obtain relevant information to the user provided input. In various aspects of the invention, the relevant information comprises biological processes, pathways, disease, and molecular interactions. A list of the relevant information 580 is also optionally displayed. In some aspects of the invention, the relevant information is grouped according to the keyword phrases used to quarry the ontological database 575. In some aspects of the invention, the relevant information is ranked either individually or in groups 585. The text list in the "Top Results Based on Experimental Keywords" 582 can be activated by clicking on the text it open up the view panel for the particular text selected and shows data relevant to the data selected (e.g. disease, process, etc.). System can be quarried by the user entering in a search term in the search field 583.

The data analysis system provides ranking icons throughout the displayed view to aid the research in prioritization of large data sets. Various ranking criteria and/or statistical test can be employed depending on the user preferences and the type of data supplied. By way of example ranking icon can be numerical, visual or both. For example, optionally provided to visualize the respective rankings can use both numerical and visual 1119. In another embodiment, the ranking icons also follow a visual metric mapped by the legends 1122, 1120 and 1121. Thus, multiple icon types can use the same or similar visual metrics.

In various aspects of the invention, a BioRank icon 1120 is used to identify pathways that may be particularly relevant to a set of differentially expressed genes. BioRank score icon represents statically identified overlaps and between the identified gene and the significant role they play in the pathway they work in. By way of example only, if a gene is a rate-limiting enzyme in a metabolic pathway, that pathway will be rewarded with BioRank points, indicating that the gene is a critical component of the pathway by having larger number of BioRank points. For example, if a gene is part of a ligand or receptor pair that is known to function in a signaling pathway, that signal initiating event is considered a high-impact event in the pathway and BioRank points will be awarded to that pathway. Other measures to be used to compile a Biorank Score can include but are not limited to: (a) rate limiting enzyme (b) pathway title gene (c) gene "hub" that is connected to many other genes (d) signal initiating gene (e) or (d) gene involved in controlling a signaling module.

In one embodiment, a series of icons to are used in various embodiments to represent high to low BioRank scores for each gene of interest. In one embodiment, numerical values are used to high to low BioRank scores. In another embodiment, different colors are used to represent high to low BioRank scores. In another embodiment, different shapes are used to represent high to low BioRank scores. For example, circle, square, triangle, half-circle, half-square, or half triangle could be used to indicate scores. For example, fully filled-in green circle indicated that this gene hit >75% of all possible key components that could be scored for this pathway. A filled-in half-circle indicates a hit to 50-75% of all possible points. A single green dot within a circle indicates 1-50% of all possible points. An open circle that is empty with no color filled-in indicates that the gene did not hit any of the key components of the pathway.

Figure 11B:
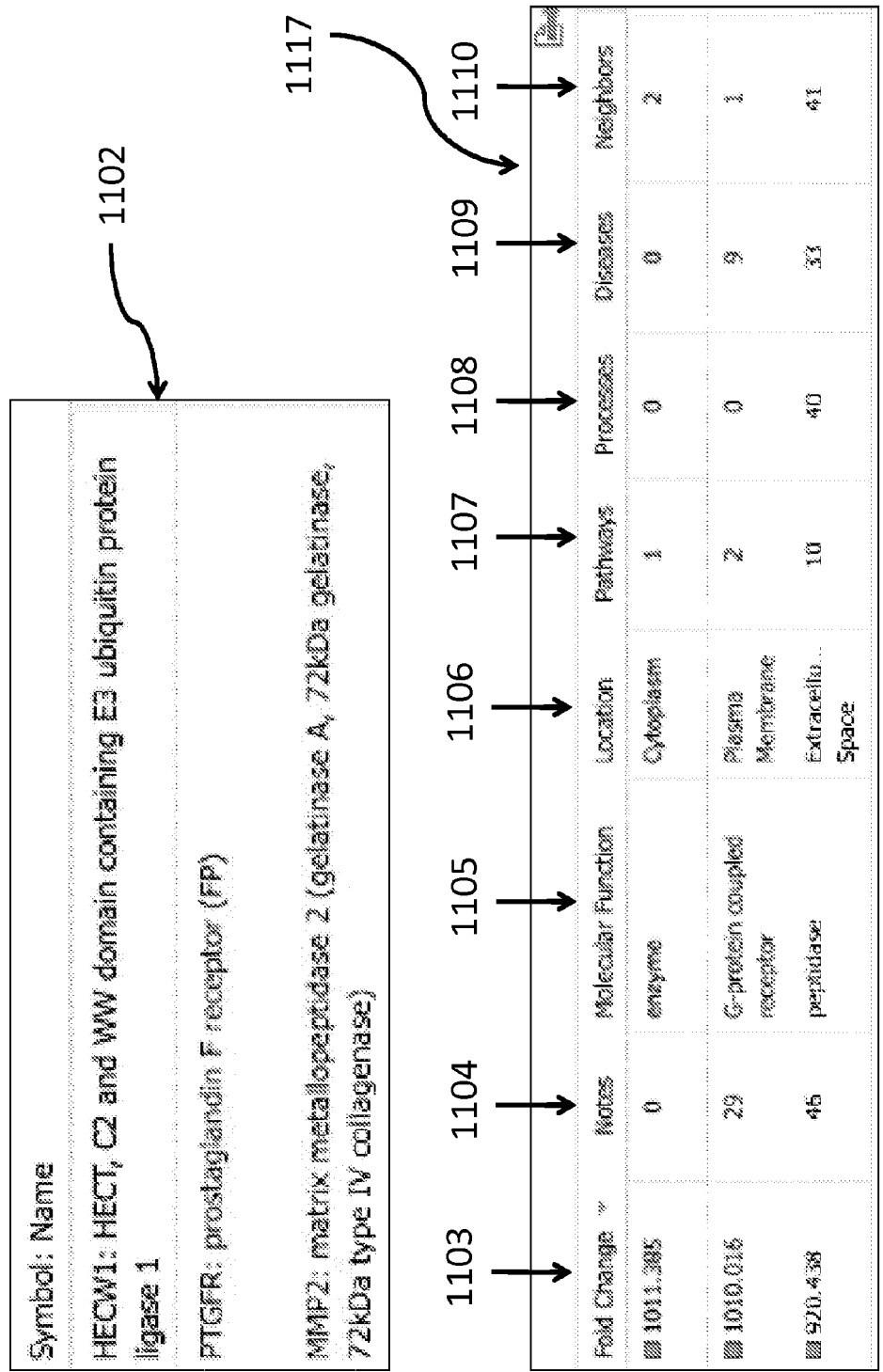
FIG. 11(B) depicts an embodiment of the "Gene Table" module graphical user interface where the user can select which properties to sort or rank data points 1117.
Figure 11C:
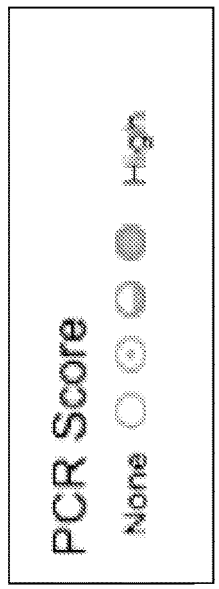
FIG. 11(C) depicts several embodiments of ranking icons.
Figure 11C:
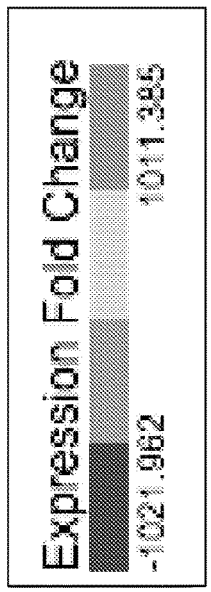
Figure 11C:
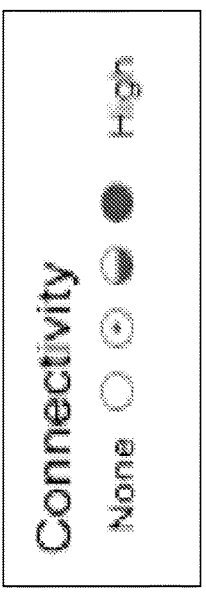

FIG. 11(C), 1122 depicts a connectivity ranking legend. Connectivity Rank to identify genes in your dataset that have a lot of molecular interactions with other genes in your dataset. A full red circle means that a gene is in the top 25% of connected genes in your dataset. The number of connections (and details about all of those connections) this rank is based on are available in the molecular interactions in the database. Genes that are highly connected to other genes in your dataset are worth highlighting as often those genes may be known to affect the activity or expression of other genes that are differentially regulated in your samples. Understanding how highly connected genes or "hubs" regulate other genes in your dataset can lead to mechanistic understanding of the transcriptional changes occurring in the cells of interest.

FIG. 11(C), 1121 depicts a PCR score legend. The green circles indicate the PCR Score assigned to each pathway, process, or disease. Circles which are more filled indicate a pathway (or process or disease) with a higher score than those associated with circles which are less filled. Specifically, the PCR Score is calculated as the sum of the absolute value of the log-fold-change (base 2) for each interrogated gene in the annotation. Using this measure, annotations with greater fold-changes (up or down) will rank higher than annotations in which smaller changes were detected in expression levels. Thus, the PCR Score provides a measure of the amount of fold-change observed for interrogated genes in that annotation while accounting for the large dynamic range of real-time PCR data.

In various embodiment, the content of the user provided data set alone is used to generate lists of relevant pathways, processes, diseases, interactions and any other kinds of information that is compiled in an ontological database. In some aspects of the invention, the lists are generated from the identity of the tests (e.g. particular genes) in a user provided data set. In some aspects of the invention, the experimental results are used to generate the lists as well (e.g. diseases where the gene is over expressed).

Figure 6A:
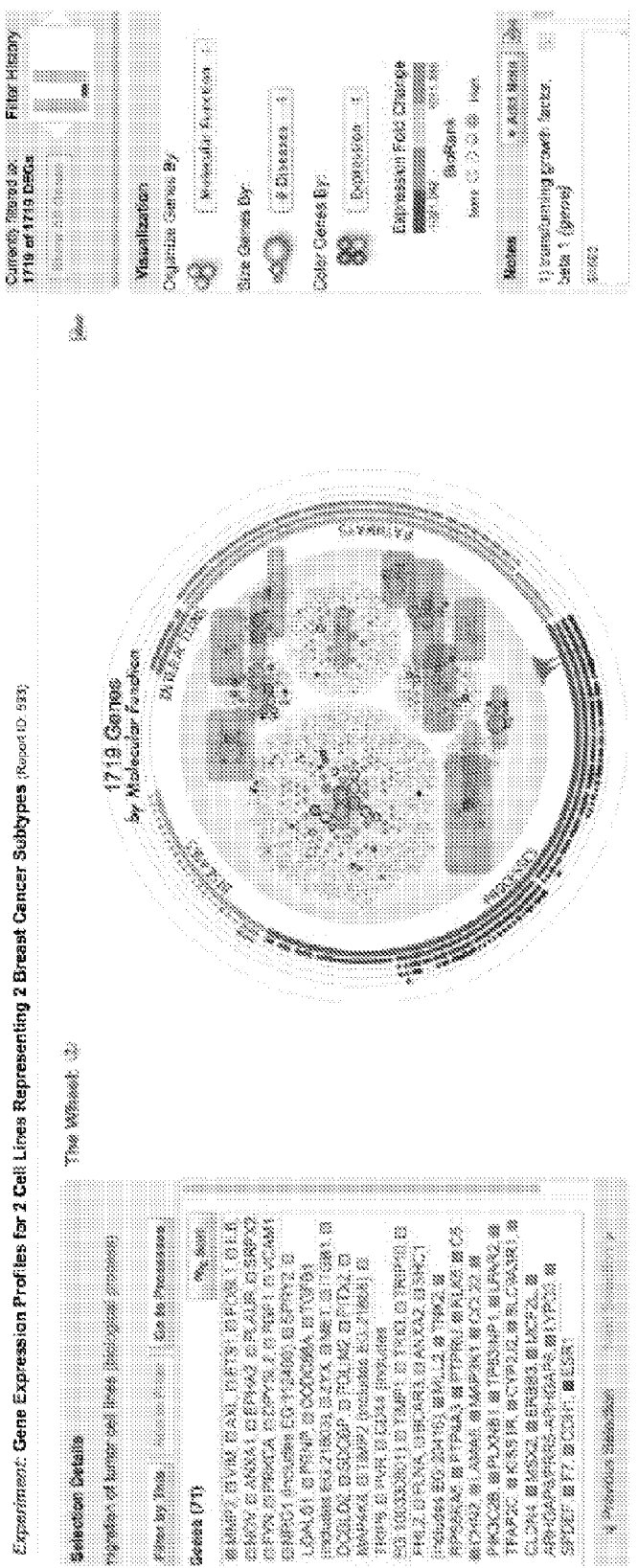
FIG. 6(A) depicts an embodiment of the system illustrating the graphical user interface being accessed by a user in a "Gene Wheel" view 601.

Referring now to FIG. 6(A), a diagram of another aspect of the system in this particular embodiment, constructed in accordance with the present invention is illustrated. FIG. 6(A) displays the "Gene Wheel" view 601. The "Gene Wheel" view can be accessed by selecting the view selection icon 422 "The Wheel". In this particular embodiment, FIG. 6(B) the graph 610 is organized around a wheel shaped structure. In the center of the wheel 610 the members/data points of a user provided data set are individually represented by data icons 611, 612, and 613. The data icons 611, 612, and 613 are displayed as circular areas on the graph 610. The data icons 611, 612, and 613 are further assigned an area, a color and an edge thickness. In one embodiment, the color of a data icon representing a data point is related to a quantitative value obtained from the user provided data set. In this particular embodiment, the user provided data set comprises expression profiles of a set of genes and the color of a data icon relates to the level of differential expression for each gene. In some aspects of the invention, the area of the data icons relate to a level of association with a set of features. Further, the data icons are grouped into areas, which are defined by a light shading and the clustering of the data icons in relative position to each other. A selected data icon 613 is indicated by a black border around it. Additional information about the selected data icon 613 is displayed in a designated area 660, labeled "Selection Details".

Figure 6B:
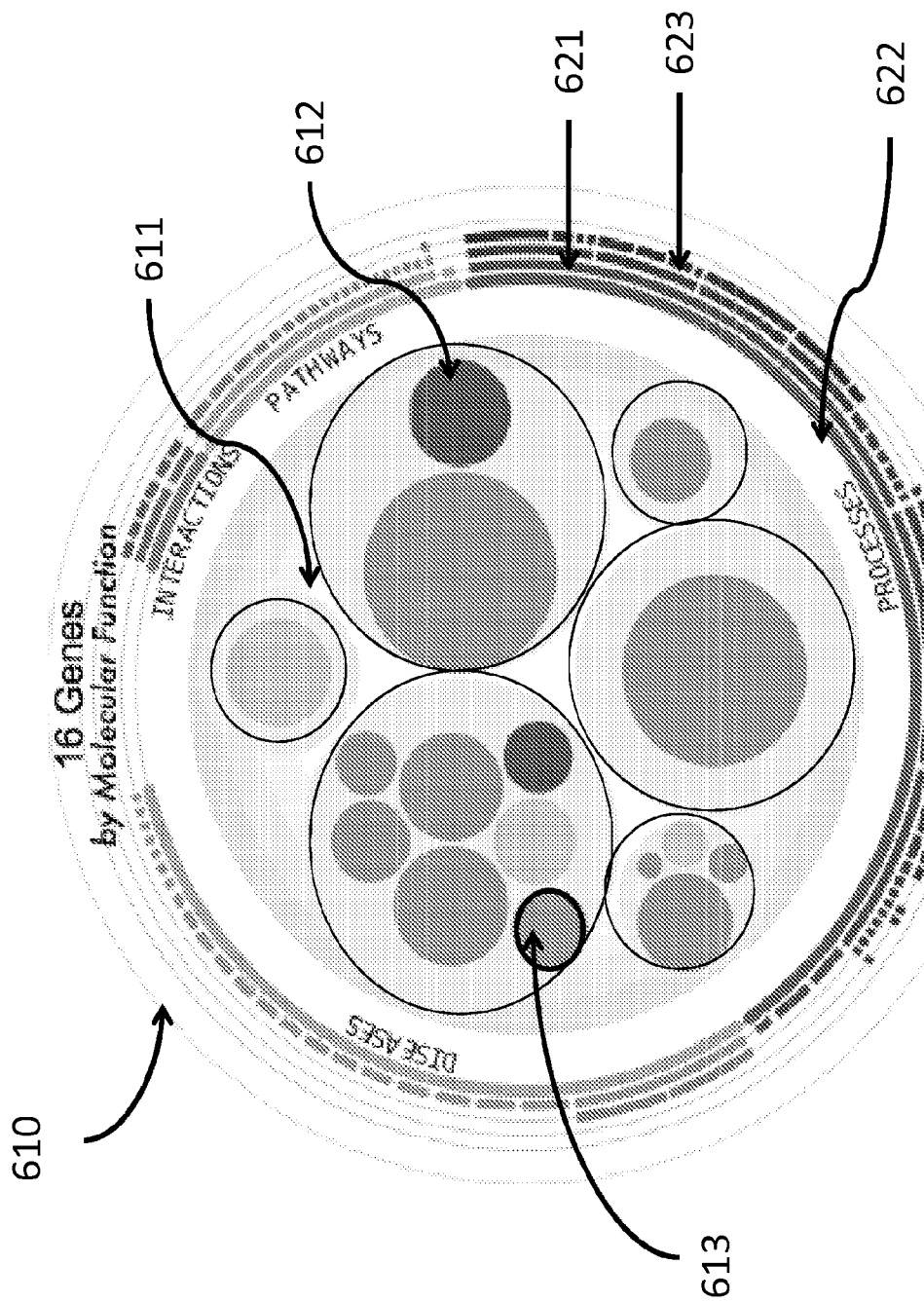
FIG. 6(B) depicts an embodiment of the "The Wheel" module illustrating the graphical user interface representing all the genes identified in the data set supplied by the user 610.

In FIG. 6(B), graph 610, the set of features are represented by feature icons 621, 622, and 623. The feature icons 621, 622, and 623 are displayed as shapes that are a portion of the perimeter of various circles surrounding the data icons 611, 612, and 613. The feature icons 621, 622, and 623 are further assigned an arch length, a color, a placement in one of the concentric circles on the perimeter of the graph 610 and a grouping with other feature icons. The feature icons 621, 622, and 623 represent biological properties related to the data points represented in the center. The biological properties may comprise groups of various pathways, cellular processes, molecular functions, networks, biomarker status, diseases or other biological properties. In graph 610, the feature icons that are associated with each feature icon group are positioned under the arch taken up by the feature icon denoting the group. Further, the biological properties are grouped in subcategories of various focus level. The feature icons in various subcategories are positioned in a concentric circle based on their focus level. The isoform icons, for example 544, can be presented as a visual icon and can include a visual metric showing the number of specific isoform annotations.

A "Filter History" module FIG. 4(A), 404 displays the filter icons that are associated with filters that are applied to the user provided data set. When a user selected a particular data point to filter it removes all other data points from view. This filter allows the user to explore that data point in great detail. Data and feature icons filtered through in this fashion remain displayed on graph 410. In various aspects of the invention, the filtered data set is maintained in the alternative views/modules of the data analysis package (e.g. Pathways, Interactions, and Diseases etc.).

The "Filter History" window FIG. 4(A), 404 displays the filter icons in a graphical fashion 410. Each filter icon is a bar with a certain height, 408. In some aspects of the invention, the bar height 408 is related to the size of the data set eliminated through filtering. In some aspects of the invention, the bar height is related to the size of the data set remaining after filtering. In some aspects of the invention, the filter icons are selectable in a computer mediated fashion. For example, the filter icons can be selected by hovering a cursor controlled by a computer mouse over the icon and optionally clicking a button on the mouse while hovering 402. In some aspects of the invention, selecting a filter icon 402 updates the wheel graph 610 to its appearance at the time the filter associated with the selected filter icon was applied. In some aspects of the invention, selecting a filter icon results in a displayed output on the wheel graph 610 providing further information about the selected filter. In some embodiments the filter history performed by the user can be reviewed for each view of the data analysis package FIG. 4(B) by activating forward and backward buttons on the graph 406.

Figure 6C:
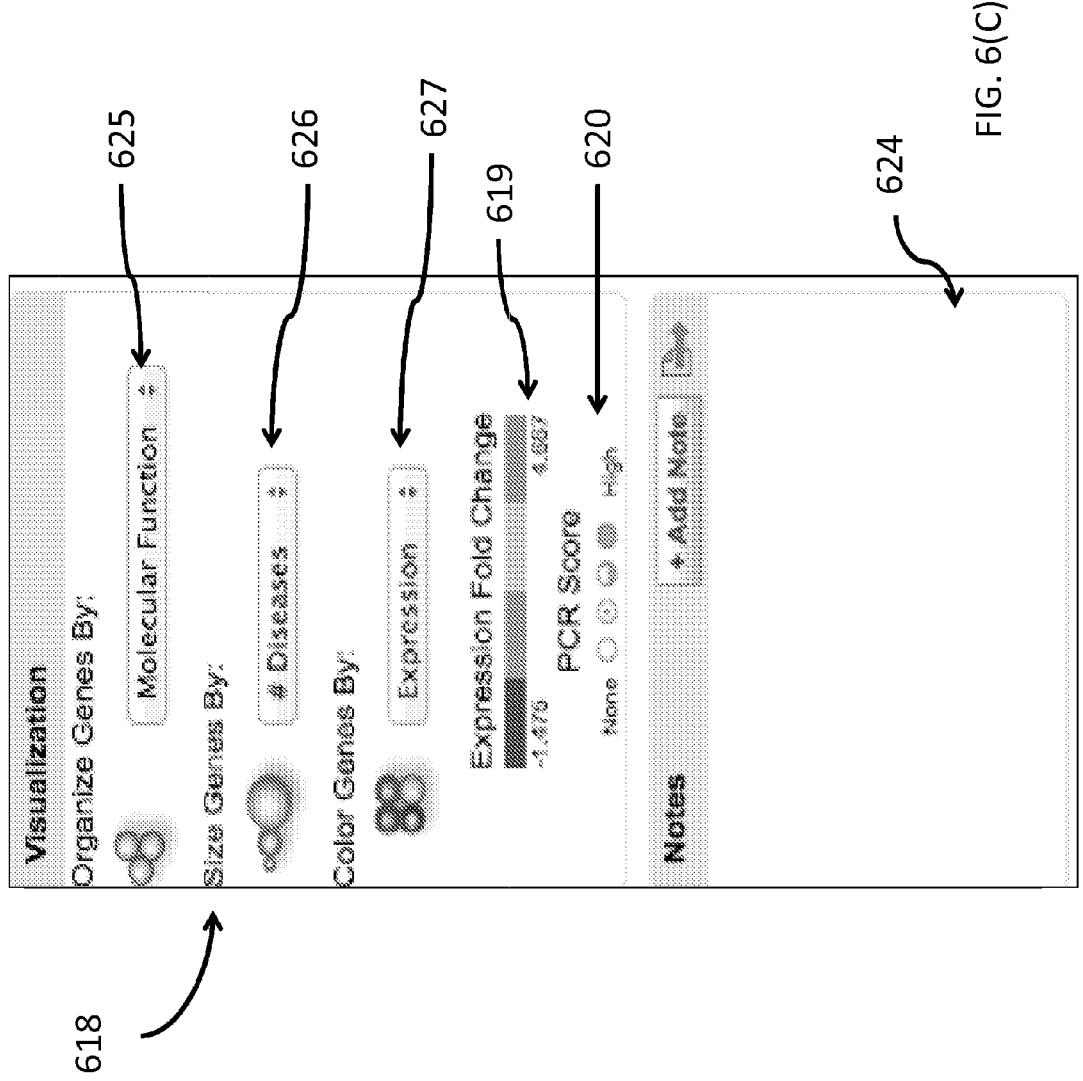
FIG. 6(C) depicts an embodiment of the "The Wheel" module illustrating the graphical user interface to change the visualization of the data on the wheel graph 618 and an embodiment illustrating the Notes field 624.
Figure 6D:
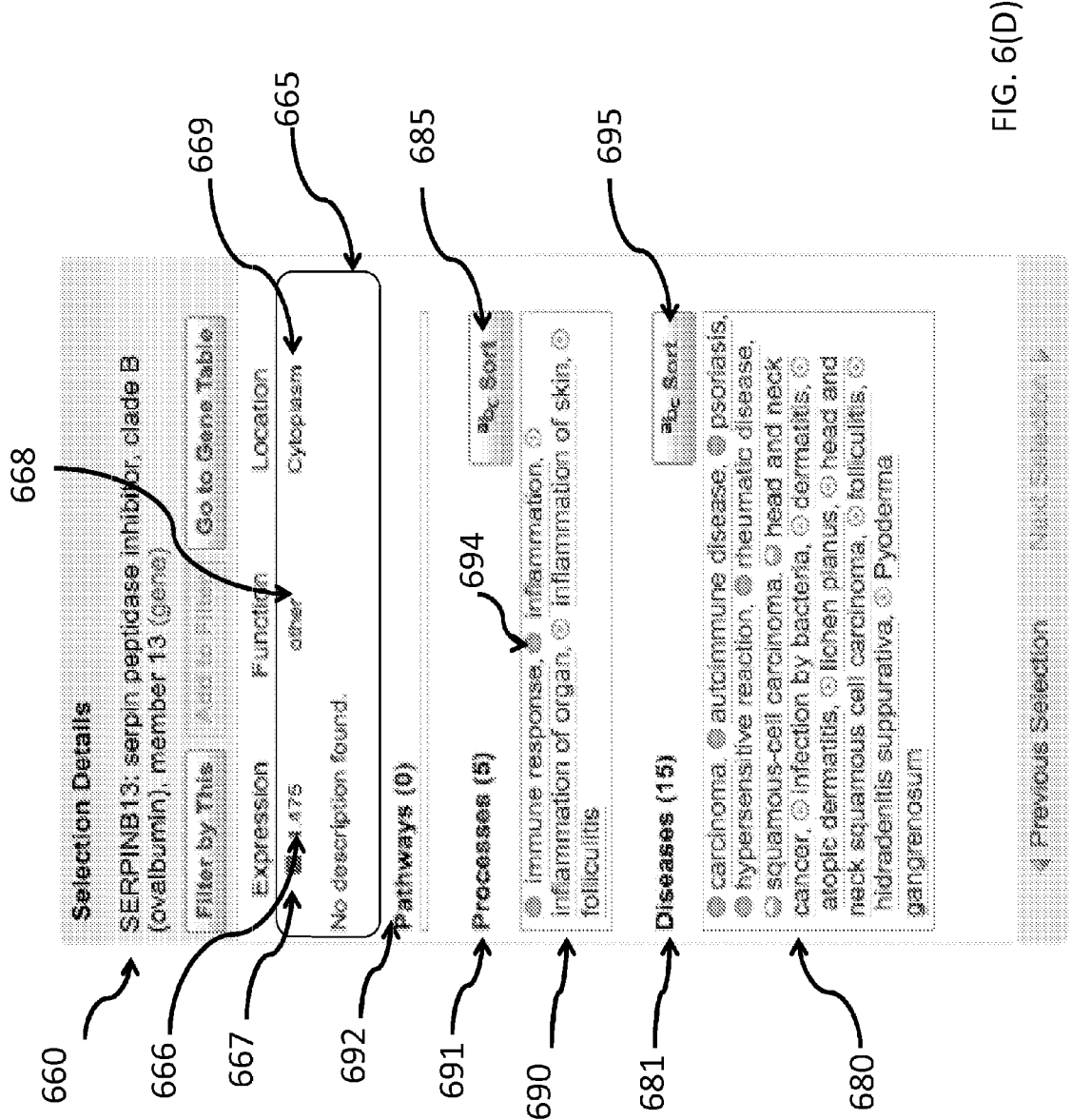
FIG. 6(D) depicts an embodiment of the "The Wheel" module illustrating the graphical user interface that provides details of a selected data point by the user 660.

The selection details area FIG. 6(D), 660 includes further information about the data point/member associated with the selected data icon. A first section 665 in the display area 660 provides basic information about the data point/member. In this particular embodiment, the data point is a measurement of the expression of a particular gene. The expression level is indicated by an icon 667 that is colored in accordance with the experimental data provided by the user. Next to it, a numerical value 666 indicates a value associated with this measurement. A text output 668 indicates the function associated with the gene. Another text output 669 indicates the localization of a protein encoded by the gene.

A second section FIG. 6(D), 680 in the display area 660 provides information about the diseases, that the gene associated with the selected data icon or a product thereof, is known to be involved in. A third section 690 in the display area 660 provides information about the processes, that the gene associated with the selected data icon or a product thereof is known to be involved in. A fourth section in the display area provides information about the pathways 692, that the gene or gene product associated with the selected data icon is known to be involved in. In various aspects of the invention, at least a portion of the information displayed in the display area 660 is obtained from an ontological database. A text output 681 above the second section 680 displays the number of diseases known to be associated with the gene associated with the selected data icon or a product thereof. Disease names and disease icons can be listed individually in the second section 680. The disease icons indicate the level of association between the individual disease and the data point associated with the selected data icon 613 from the wheel graph. A button 695 links to a sorting process for the diseases section 680 upon computer mediated user interaction with the button. A text output 691 above the third section 690 can display the number of diseases known to be associated with the gene associated with the selected data icon or a product thereof. Process names 691 and process icons 694 can be listed individually in the second section 690. The process icons can indicate the level of association between the individual disease and the data point associated with the selected data icon 613 from the wheel graph. A button 685 links to a sorting process for the processes section 690 upon computer mediated user interaction with the button. The data can be optionally sorted by the sorting process by either ranking or alphabetical as chosen by the user.

A visualization window FIG. 6(C), 618 can display selected visualization options. Optionally, the visualization window 618 provides a means to change at least a portion of the visualization options. In this particular embodiment, a pull-down menu 625 allows a user to select a criterion to organize the data icons through a computer mediated interaction. A second pull-down menu 626 can allow a user to select a criterion to size the data icons through a computer mediated interaction. A third pull-down menu 627 can allow a user to select a criterion to color the data icons through a computer mediated interaction. By way of example, the criterion to apply a particular visual metric is selected from gene expression levels or other user provided experimental data input, the number of diseases that are associated with a data point (e.g. gene), the number of processes that are associated with a data point (e.g. gene), the number of pathways that are associated with a data point (e.g. gene), or the number of interactions that are associated with a data point (e.g. gene). Thus, the visual metrics are dynamically assigned to display desired properties customizing the graph 610 for enhanced visualization and analysis of the user provided data set. The visualization window 618 can include a legend 619, mapping the colors used as visual metrics associated with various types of icons to values they represent. In various aspects of the invention, the range of the represented values is a property of the user provided data set. The mapping of the colors to values within that range is optionally adjusted dynamically to display the various values with higher sensitivity. In some aspects of the invention, other visual metrics (e.g. data icon size) are also dynamically adjusted to map the range of values associated with the user provided data set. A second legend 620 can map a second visual metric to a second set of values. In this particular example, the icon fill-in style is representative of a ranking value displayed on the disease and process icons in the disease section 680 and process section 690 and pathway section 692. The mapping of visual metrics to value ranges can be linear, exponential, logarithmic or follow any function that is suitable for the visualization of a value.

In various aspects of the invention, additional windows in the "Gene Wheel" view, as well as in other views, provide further information or enable the entry of further information. For example, the "Notes" window 624 provides a method for a user to enter information and link it to a particular data point/member. In some aspects of the invention, the user entered notes are carried through to other views of the data analysis package. FIG. 6(C), 624 provides an example view of the "Notes" window, after one or more data points/members are selected for related information entry. A list displays the selected data points/members. A box under each selection is designated for user entry of relevant information. Other sections in the "Gene Wheel" view 601 may display additional types of desired output for example by molecular function, disease types, location or other information.

Figure 7A:
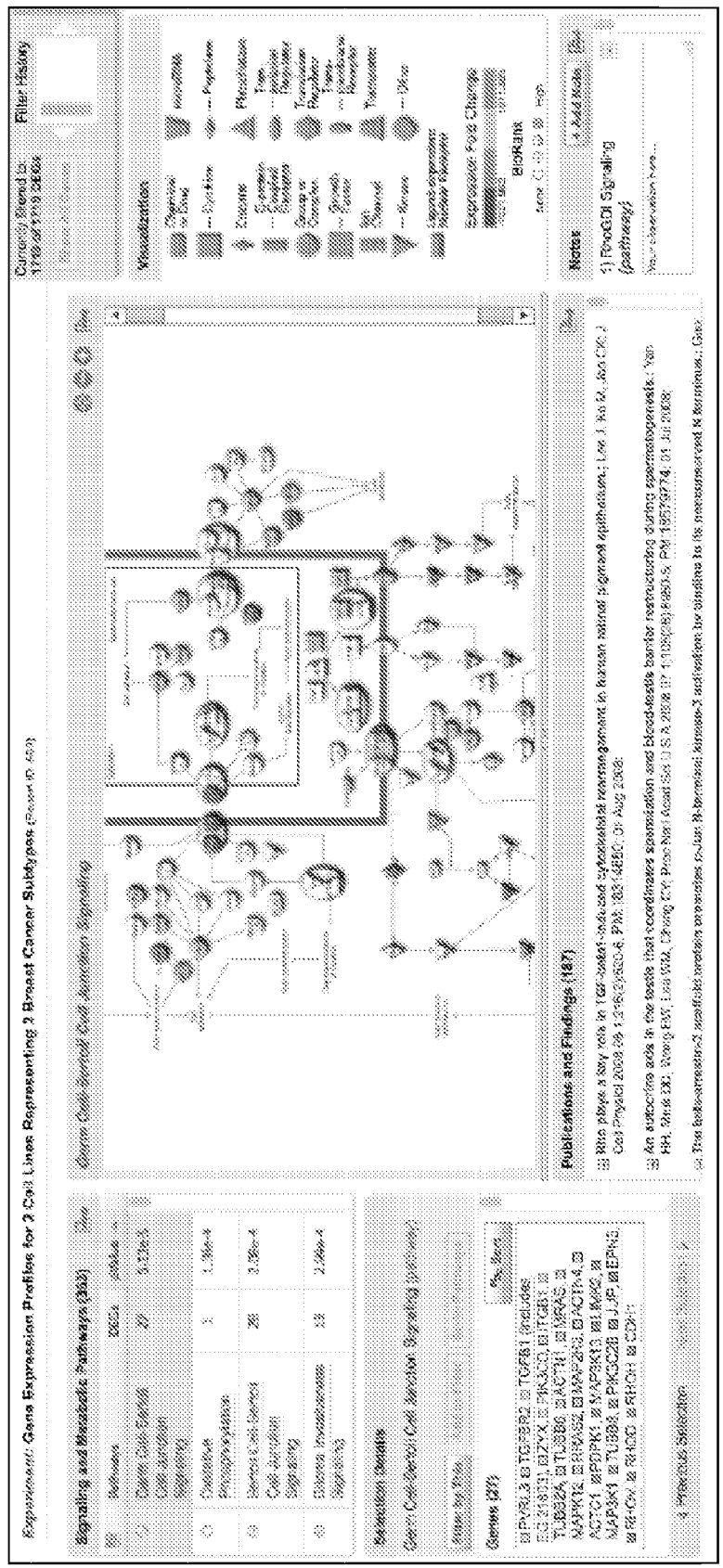
FIG. 7(A) depicts an embodiment of the system illustrating the graphical user interface being accessed by a user in a "Pathways" view 701.

Referring now to FIG. 7(A) a diagram of another aspect of the system in this particular embodiment, constructed in accordance with the present invention is illustrated. FIG. 7(A) displays the "Pathways" view 701. According to embodiments of the invention, the "Pathways" view 701 is accessed by selecting the view selection icon FIG. 4(B), 423 "Pathways". In various embodiments of the invention, the "Pathways" view lists the pathways associated with the data points/members of the user provided data set. In various aspects of the invention, the list is compiled from a database linked to the data analysis package. In various aspects of the invention, the list of pathways 709 comprises pathways that are associated with the remaining data points/members after one or more filter applications. Optionally, the listed pathways are ranked by one or more methods 707 and 714. In some aspects of the invention, the ranking comprises calculating Fisher's exact test probabilities. In some aspects of the invention, the ranking of the pathways is customized with a user bias. For example, a user selection of an associated selection box prioritizes pathways, wherein the data points/members from the user provided data set constitute key genes and interactions. In various aspects of the invention, the key genes and interactions are designated from information stemming from an ontological database. The isoform icons, for example 544, can be presented as a visual icon and can include a visual metric showing the number of specific isoform annotations.

In some aspects of the invention, a pathway icon 702 is displayed associated with each pathway in the pathway list. Optionally, the icon visualizes a particular qualitative 703 or 704 or quantitative attribute 705 or 714 associated with each pathway in the list. The visualized attribute displayed by the pathway icon can for example be the level of ranking of a particular pathway within the list of pathways in a list, the number of nodes (e.g. genes, proteins etc.) within the pathway 714, the number of data points/members from the user provided data set that are in the pathway or other relevant properties. A visual metric associated with the icon enables the display of the attribute 702. In this particular embodiment, the visual metric is a color fill style 708. Optionally, methods to sort the pathways list are provided by selecting the table title area 715 and 716. For example, selecting pathway column title is used to sort the pathways according to their name, while selecting the pathway icon column title is used to sort the pathways according to the level of the attribute that is visualized by the visual metric associated with the pathway icon.

Figure 7B:
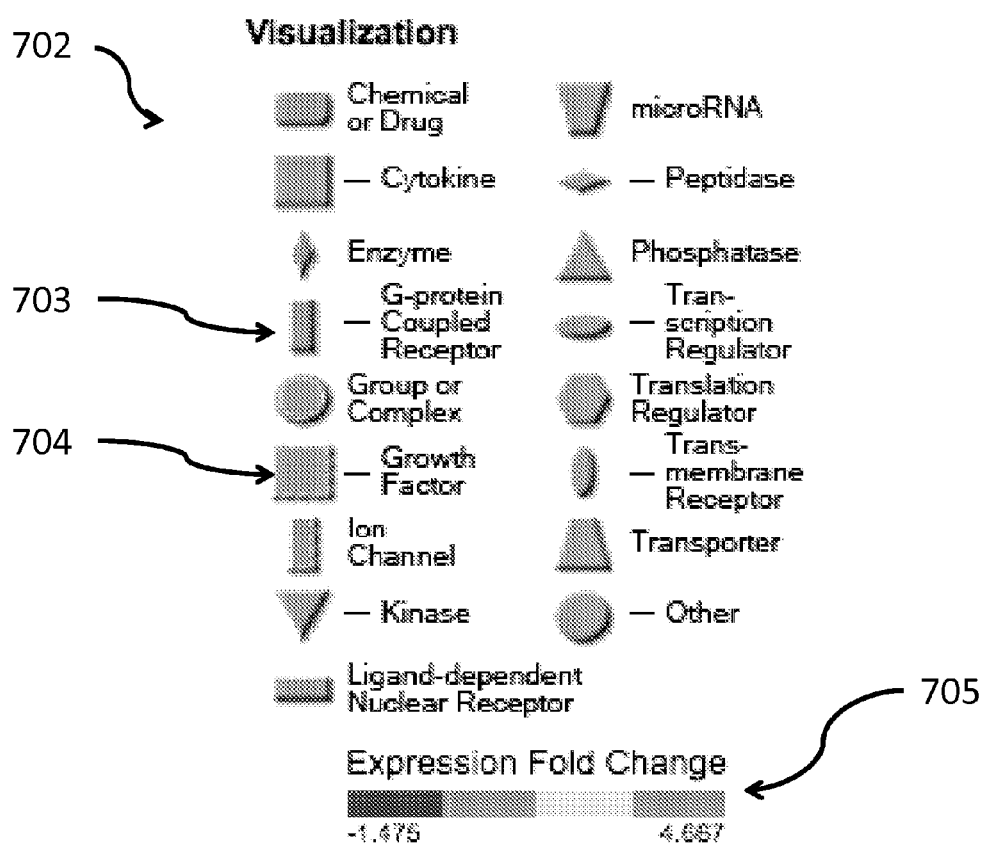
FIG. 7(B) depicts an embodiment of the "Pathways" module illustrating the graphical user interface to visualize what types of molecules are in the pathway by icon type 702 and an embodiment illustrating the Notes field 706.

Various model icons enable the visualization 702 of particular attributes associated with nodes within the displayed pathway. By way of example, the shape of an icon 703 and 704 can link a function (e.g. ion channel), a molecule type (e.g. microRNA or siRNA), or any other desired attribute to nodes of the pathway. Additional visual metrics (e.g. coloring) 707, 708 can be used to display qualitative or quantitative attributes associated with each node (e.g. the expression fold change for the nodes that are in the user provided data set). A "Notes" window 706 provides a method for a user to enter information and link it to a particular data point/member. In some aspects of the invention, the user entered notes are carried through to other views of the data analysis package. FIG. 7(B), 706 provides an example view of the "Notes" window, after one or more data points/members are selected for related information entry. A box under each selection 706 is designated for user entry of relevant information.

Figure 7C:
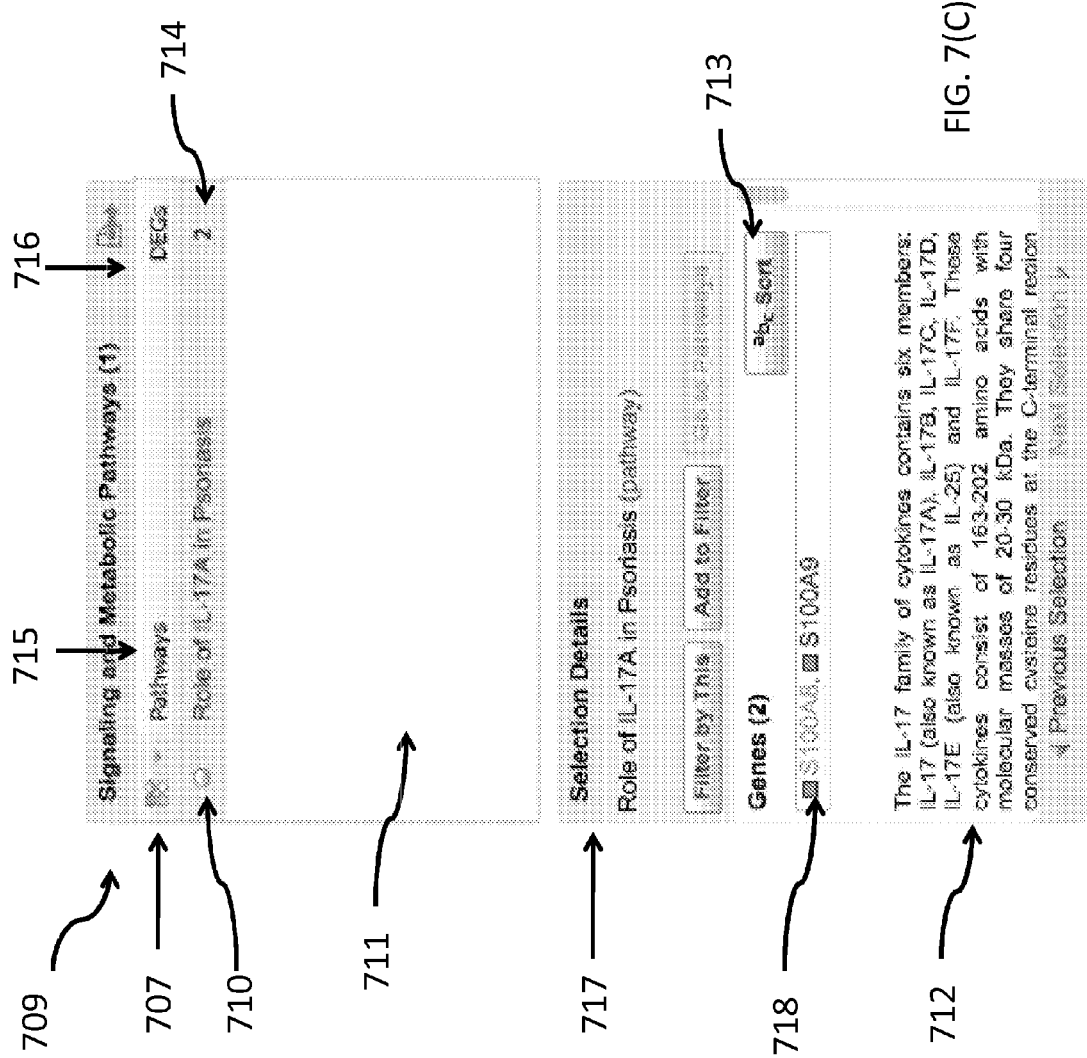
FIG. 7(C) depicts an embodiment of the "Pathways" module illustrating the graphical user interface for showing the user supplied data by signaling and metabolic pathways 709 and details of a selected data point by the user 717.

In various aspects of the invention, additional windows in the "Pathways" view 701 provide further information or enable the entry of further information. For example, a "Signaling and Metabolic Pathways" FIG. 7(C), 709 additional information about a selected pathway or a selected data point/member can also be provide by the report. The window can be selected to display a list of pathways 711, comprising a ranking score 710. The pathway can be further characterized by the number of gene nodes in the data set are associated with that particular pathway 714. The data in the 709 window can be sort by column titles 715 or 716 and by ranking criteria 707 and other relevant information.

In various aspects of the invention, additional windows in the "Pathways" view 701 provide further information or enable the entry of further information. For example, a "Selection Details" FIG. 7(C), 717 window provides additional information about a selected pathway or a selected data point/member can also be provide by the report. The pathway associated additional information displayed in the "Selection Details" 717 window can be selected from a list of pathways comprising a ranking score 718, a pathway-related list of gene nodes 718 stemming from the user provided data set, optionally accompanied with icons visualizing each member of the list, a description of the pathway 712 and other relevant information. In some aspects of the invention, the list of nodes stemming from the user provided data set can be sorted by selecting a sort button 713. The sorting can be performed according to various criteria, including, but not limited to, for example, the expression fold change, alphabetical or another attribute associated with the user provided experiment.

Figure 7D:
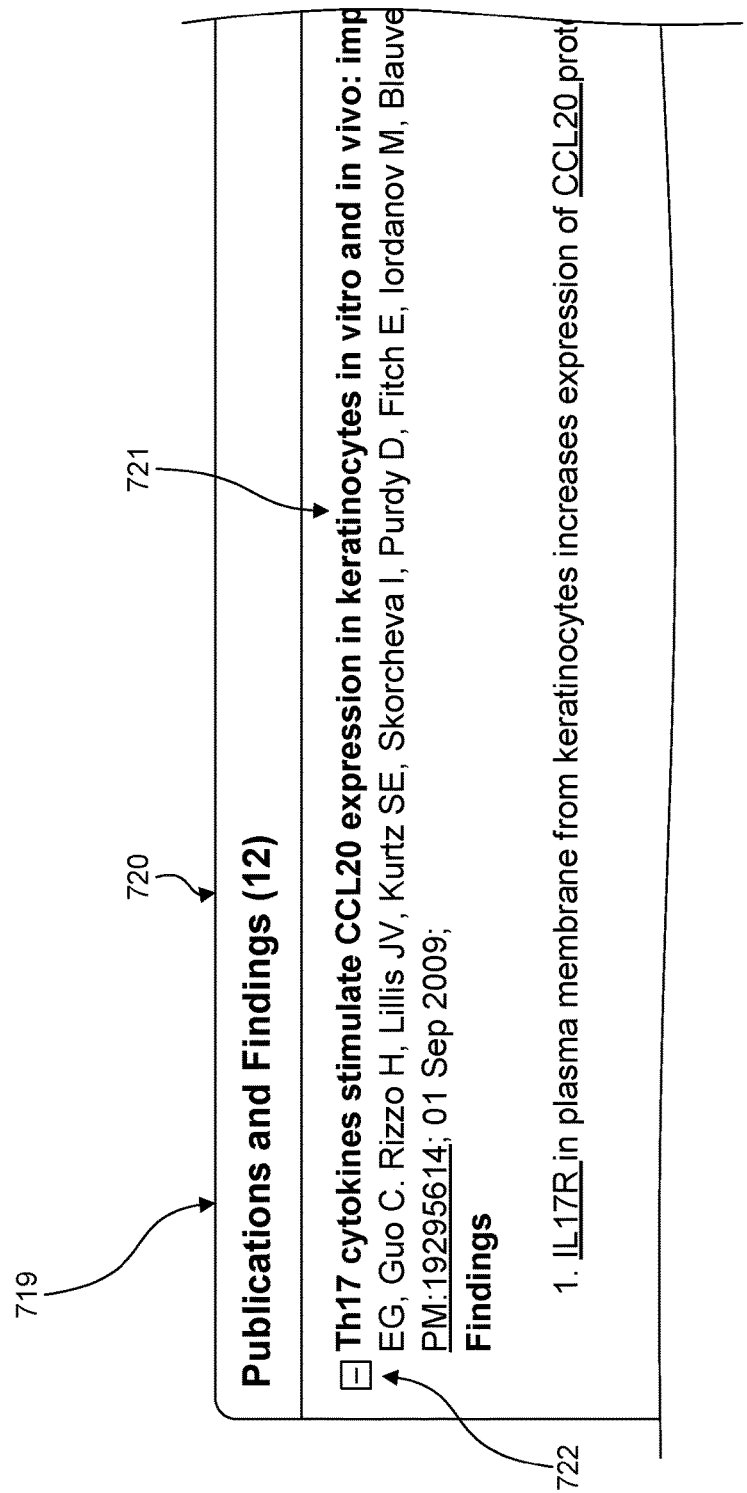
FIG. 7(D) depicts an embodiment of the "Pathways" module illustrating the graphical user interface "Publication and Findings" on the literature that supports the details of a selected data point by the user.

In various aspects of the invention, additional windows in the "Pathways" view 701 provide further information or enable the entry of further information. For example, a "Publication and Findings" FIG. 7(D), 719 provide additional information on the publications related to the pathways in the report. After selecting a particular pathway from the pathways listed in 709 or a particular gene listed in 718 information linked to an database is loaded into 719 window. The data retrieved from the database is further described by the number of publication found 720 and the title 721. The user can activate an icon for example 722 and uncover more publication linked to primary publication 721 titled.

In various aspects of the invention, an additional "Publications" window lists and optionally links to publications related to the pathway. In some aspects of the invention, publications that are specifically related to pathway nodes stemming from the user provided data set will be prioritized.

Figure 8A:
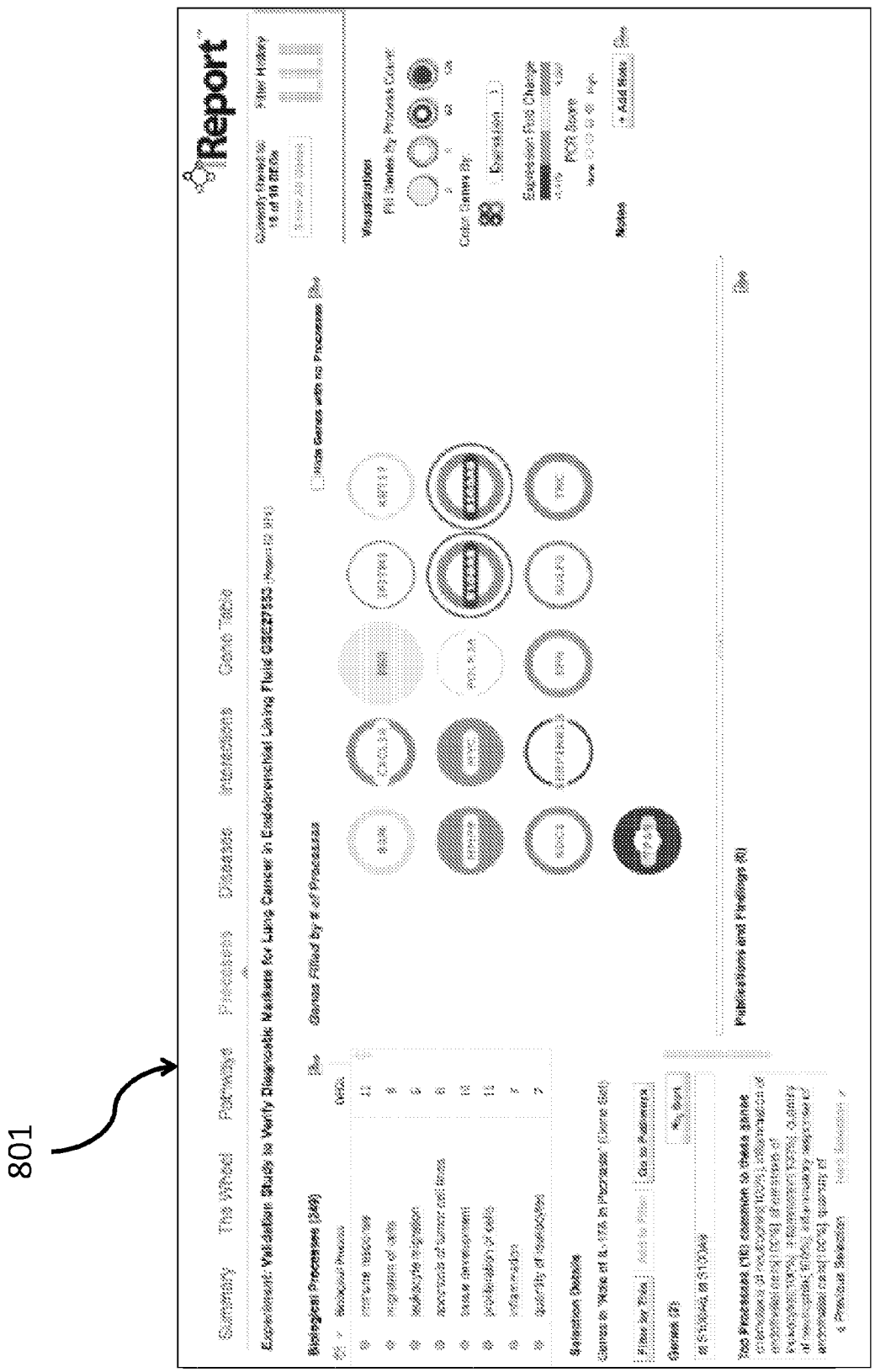
FIG. 8(A) depicts an embodiment of the system illustrating the graphical user interface being accessed by a user in a "Processes" view 801.

Referring now to FIG. 8(A), a diagram of another aspect of the system in this particular embodiment, constructed in accordance with the present invention is illustrated. FIG. 8(A), 801 displays the "Processes" view. According to embodiments of the invention, the "Processes" view 801 is accessed by selecting the view selection icon FIG. 4(B), 424 "Processes".

In various embodiments of the invention, the "Biological Processes" field 810 lists the processes 809 associated with the data points/members of the user provided data set. In various aspects of the invention, the list 810 is compiled from an database linked to the data analysis package. In various aspects of the invention, the list of biological processes comprises processes that are associated with the remaining data points/members after one or more filter applications. Optionally, the listed processes are ranked 814. In some aspects of the invention, the ranking comprises calculating Fisher's exact test probabilities. In some aspects of the invention, the ranking of the processes is customized with a user bias. In some aspects of the invention, a process icon is displayed associated with each process in the processes list 815. Optionally, the icon visualizes a particular qualitative or quantitative attribute associated with each process in the list. The visualized attribute displayed by the process icon can for example be the level of ranking of a particular process within the list of processes in a list, the number of nodes (e.g. genes, proteins etc.) within the process, the number of data points/members from the user provided data set that are involved in the process or other relevant properties for example 816. A visual metric associated with the icon enables the display of the attribute. In a particular embodiment, the visual metric is a color fill style for example, 815. Optionally, methods to sort the processes list are provided, for example, by selecting the table title column areas for example, 817 and 818. For example, selecting process column title "Biological Process" is used to sort the processes according to their name, while selecting the process icon column title is used to sort the processes according to the level of the attribute that is visualized by the visual metric associated with the process icon. The isoform icons, for example 544, can be presented as a visual icon and can include a visual metric showing the number of specific isoform annotations.

For another example, a "Selection Details" window 819 provides additional information about a selected process or a selected data point/member. The process associated additional information when selected by the user for example 809 or 812 is displayed in the "Selection Details" window is selected from a list comprising a ranking score, a process-related list of data points/members from the user provided data set, optionally accompanied with icons visualizing each member of the list 811, a description of the process and other relevant information. In some aspects of the invention, the process-related list of data points/members from the user provided data set can be sorted by selecting a sort button 813. The sorting can be performed according to various criteria, including, but not limited to, for example, the expression fold change, alphabetical or another attribute associated with the user provided experiment.

Figure 8B:
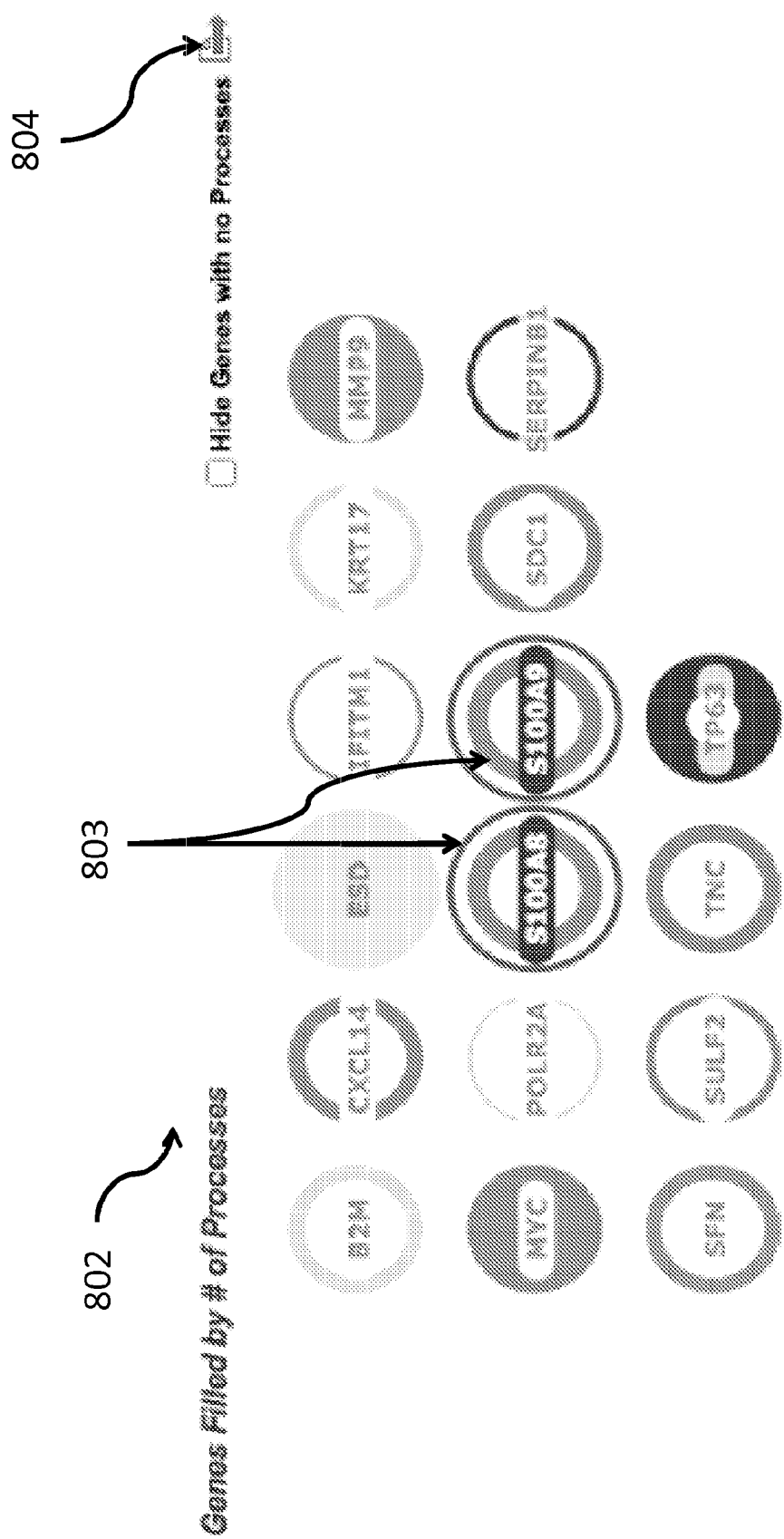
FIG. 8(B) depicts an embodiment of the "Processes" module illustrating a graphical user interface showing the user supplied data by biological process 802.

A process graph FIG. 8(B), 802 can list the data points/members of the user provided data set using data icons 805. In various aspects of the invention, the displayed data points/members are a remaining subset of the user provided data set after the application of one or more filters. Various visual metrics can be used to display relevant attributes on the data icons. A highlighted text style 803 is used as a visual metric to identify the data points/members on process graph 802 associated with a selected process from the 809 field. The selected data icons are optionally display with a border in a different color than the rest of the data icons. In some aspects of the invention, the border color and the text highlighting color are the same.

A visualization window FIG. 8(C) can display selected visualization options. Optionally, the visualization window provides a means to change at least a portion of the visualization options. In one embodiment, a pull-down menu 806 allows a user to select a criterion to accordingly color fill the data icons through a computer mediated interaction. A second pull-down menu 806 allows a user to select a criterion to accordingly color the data icons through a computer mediated interaction. By way of example, the criterion to apply a particular visual metric is selected from gene expression levels or other user provided experimental data input, the number of diseases that are associated with a data point (e.g. gene), the number of processes that are associated with a data point (e.g. gene), the number of pathways that are associated with a data point (e.g. gene), or the number of interactions that are associated with a data point (e.g. gene). Thus, the visual metrics are dynamically assigned to display desired properties customizing the processes graph for enhanced visualization and analysis of the user provided data set. The visualization window includes a legend 807, mapping the colors used as visual metrics associated with various types of icons to values they represent. In various aspects of the invention, the range of the represented values is a property of the user provided data set. The mapping of the colors to values within that range is optionally adjusted dynamically to display the various values with higher sensitivity. In some aspects of the invention, other visual metrics (e.g. data icon size) are also dynamically adjusted to map the range of values associated with the user provided data set. A second legend maps a second visual metric to a second set of values. In this particular example, the icon fill-in style is representative of a ranking value displayed on the process icons 807 and 808. The mapping of visual metrics to value ranges can be linear, exponential, logarithmic or follow any function that is suitable for the visualization of a value.

In various aspects of the invention, additional windows in the "Processes" view, provide further information or enable the entry of further information. For example, the "Notes" window 804 provides a method for a user to enter information and link it to a particular data point/member. In some aspects of the invention, the user entered notes are carried through to other views of the data analysis package.

Figure 8D:
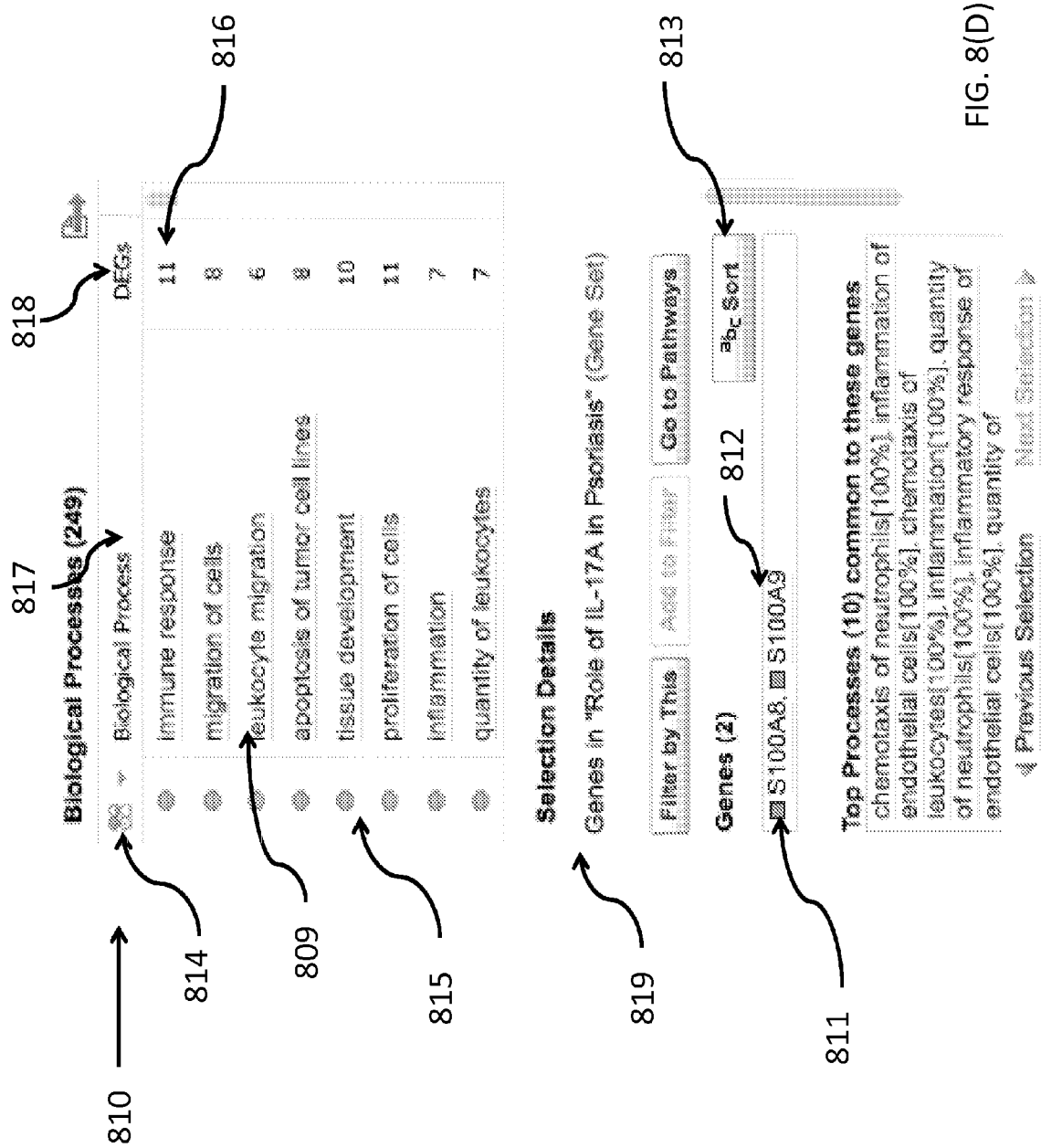
FIG. 8(D) depicts an embodiment of the "Processes" module illustrating the graphical user interface showing the data by the biological processes found for each data point 810 and details of a selected data point by the user 819.
Figure 8E:
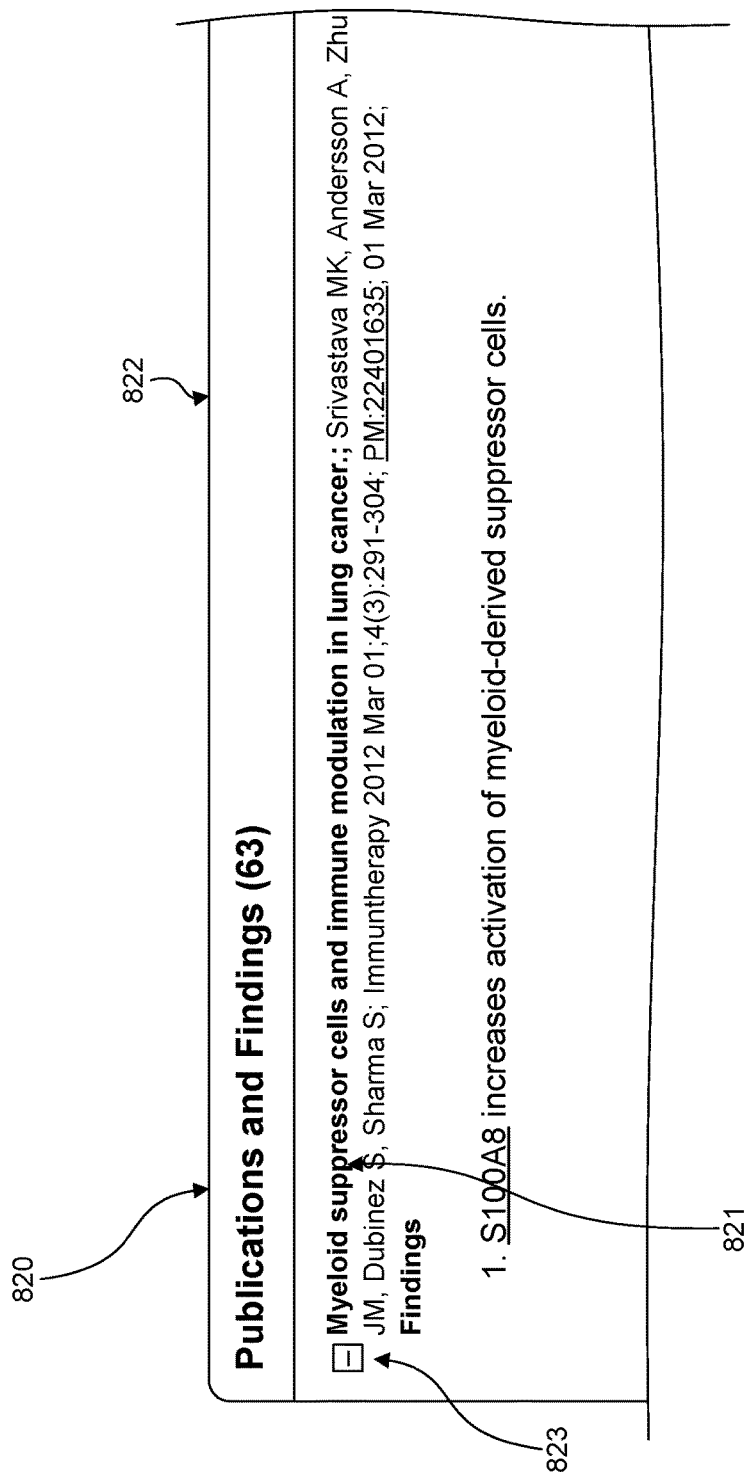
FIG. 8(E) depicts an embodiment of the "Processes" module illustrating the graphical user interface "Publication and Findings" on the literature of a user selected data point 822.

In various aspects of the invention, an additional "Publications and Findings" window FIG. 8(E), 822 lists publication and optionally links to publications related to the pathway. In some aspects of the invention, publications that are specifically related to pathway nodes stemming from the user provided data set will be prioritized. In some aspects of the invention, publications that are specifically related to selected user provided data set will be prioritized. For example, a "Publication and Findings" 822 additional information regarding the biological process if available. By selecting a particular process from the biological processes listed 810 or a particular gene 812 the information linked to an database is loaded into Publications and Findings window 822. The data retrieved from the database is further described by the number of publication 820 found and the titles of the publications for example 821. The user can activate an icon for example 823 and uncover more publication linked to primary publication titled 821.

Figure 9A:
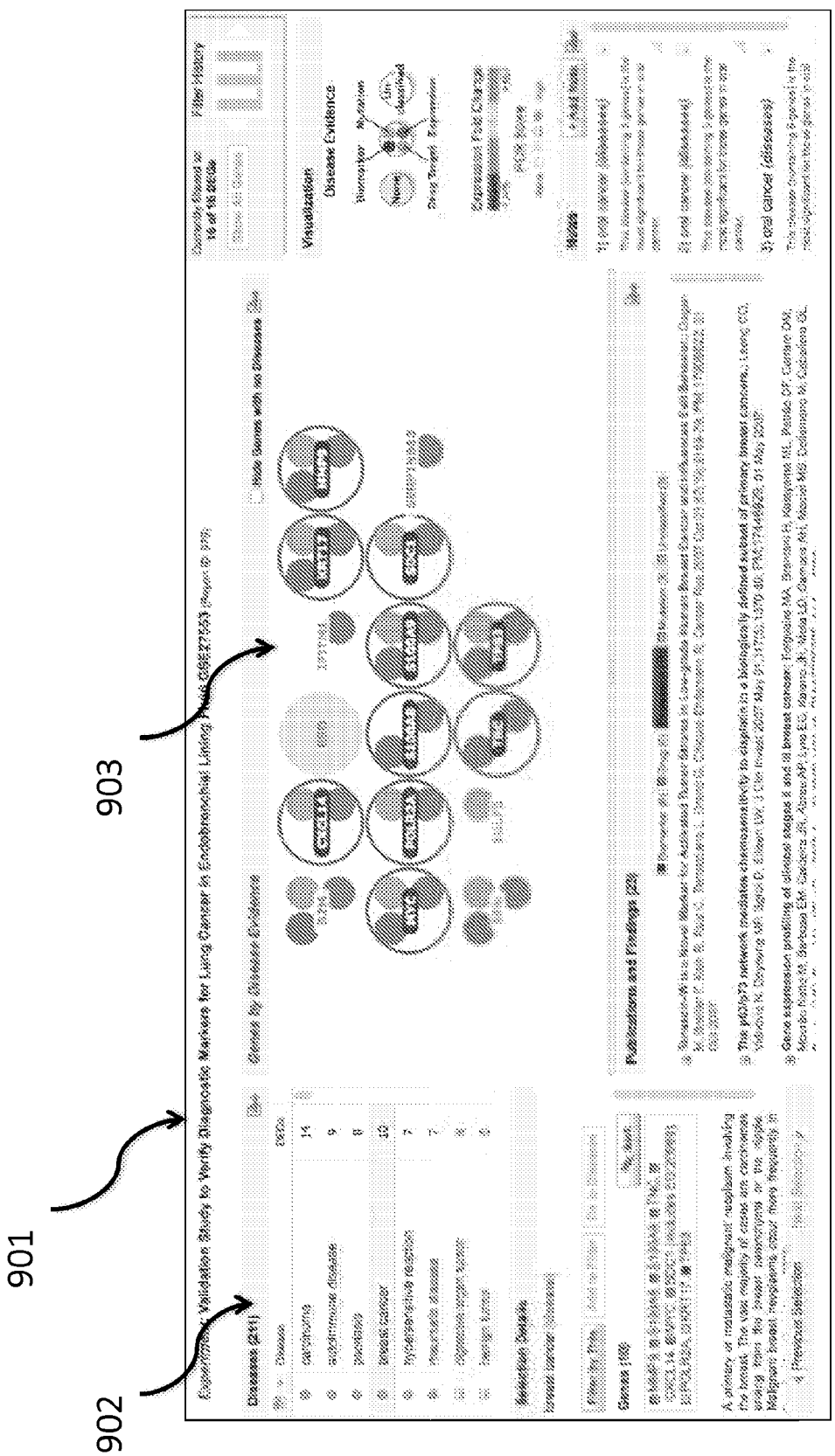
FIG. 9(A) depicts an embodiment of the system illustrating the graphical user interface being accessed by a user in a "Diseases" view 901.

Referring now to FIG. 9(A) a diagram of another aspect of the system in this particular embodiment, constructed in accordance with the present invention is illustrated. FIG. 9(A) displays the "Diseases" view 901. According to embodiments of the invention, the "Diseases" view 901 is accessed by selecting the view selection icon FIG. 4 (B), 425 "Diseases".

In various embodiments of the invention, the "Diseases" view lists the diseases associated with the data points/members of the user provided data set 918. In various aspects of the invention, the list of diseases 918 is compiled from an database linked to the data analysis package. In various aspects of the invention, the list of diseases comprises diseases that are associated with the remaining data points/members after one or more filter applications. The listed diseases may be ranked 919. In some aspects of the invention, the ranking comprises calculating statistical probabilities, for example, Fisher's exact test probabilities. In some aspects of the invention, the ranking of the diseases is customized with a user bias. In some aspects of the invention, a disease icon is displayed associated with each disease in the diseases list 920. Optionally, the icon visualizes a particular qualitative or quantitative attribute associated with each disease in the list. The visualized attribute displayed by the diseases icon can for example be the level of ranking of a particular diseases within the list of diseases in a list, the number of nodes (e.g. genes, proteins etc.) that are associated with the disease, the number of data points/members from the user provided data set that are involved in the diseases 921 or other relevant properties. A visual metric associated with the icon enables the display of the attribute. In a particular embodiment, the visual metric is a color fill style 919. Optionally, methods to sort the diseases list are provided by selecting the table title area. For example, selecting diseases column title "Disease" is used to sort the diseases according to their name, while selecting the disease icon column title is used to sort the diseases according to the level of the attribute that is visualized by the visual metric associated with the diseases icon.

Figure 9B:
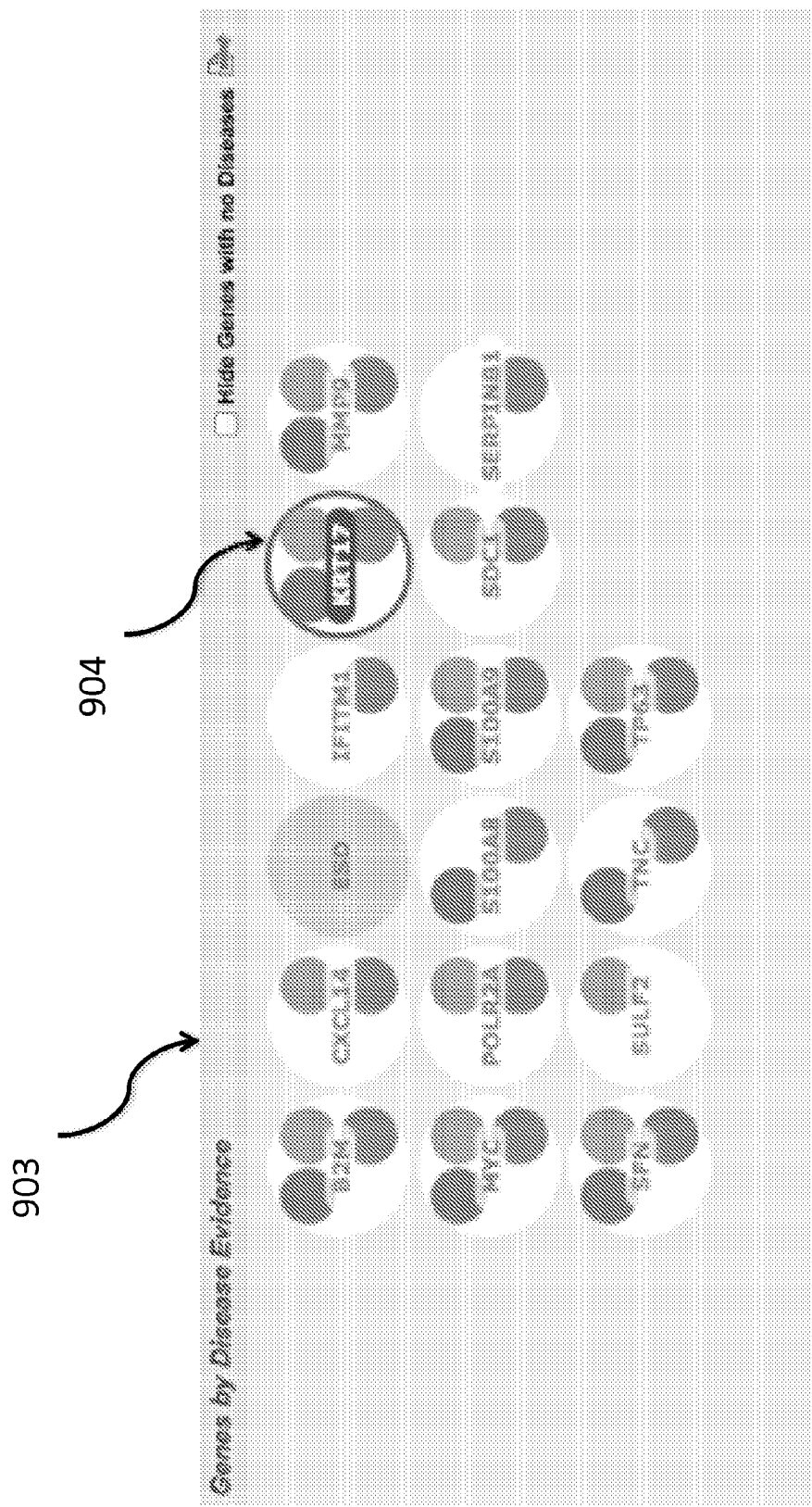
FIG. 9(B) depicts an embodiment of "Diseases" module illustrating the graphical user interface showing the user supplied data by their association with disease 903.
Figure 9C:
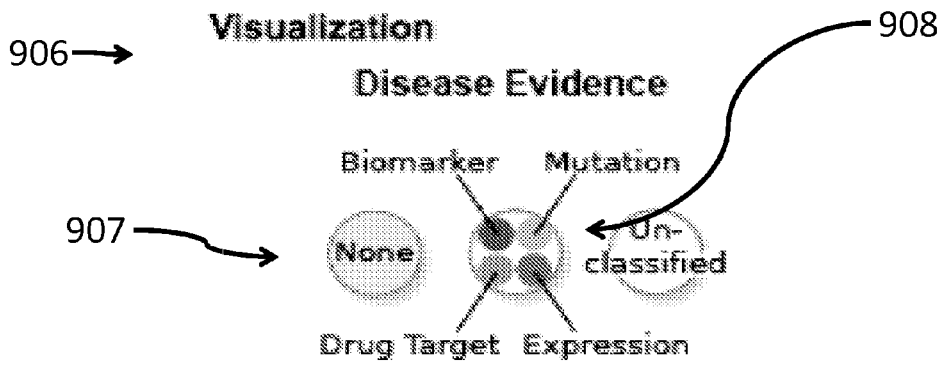
FIG. 9(C) depicts embodiment of the "Diseases" module illustrating the graphical user interface to visualize the user supplied data by disease information such as mutation, biomarkers, mutations, drug target and expression 906 and an embodiment of the Notes field 909.
Figure 9C:
Figure 9D:
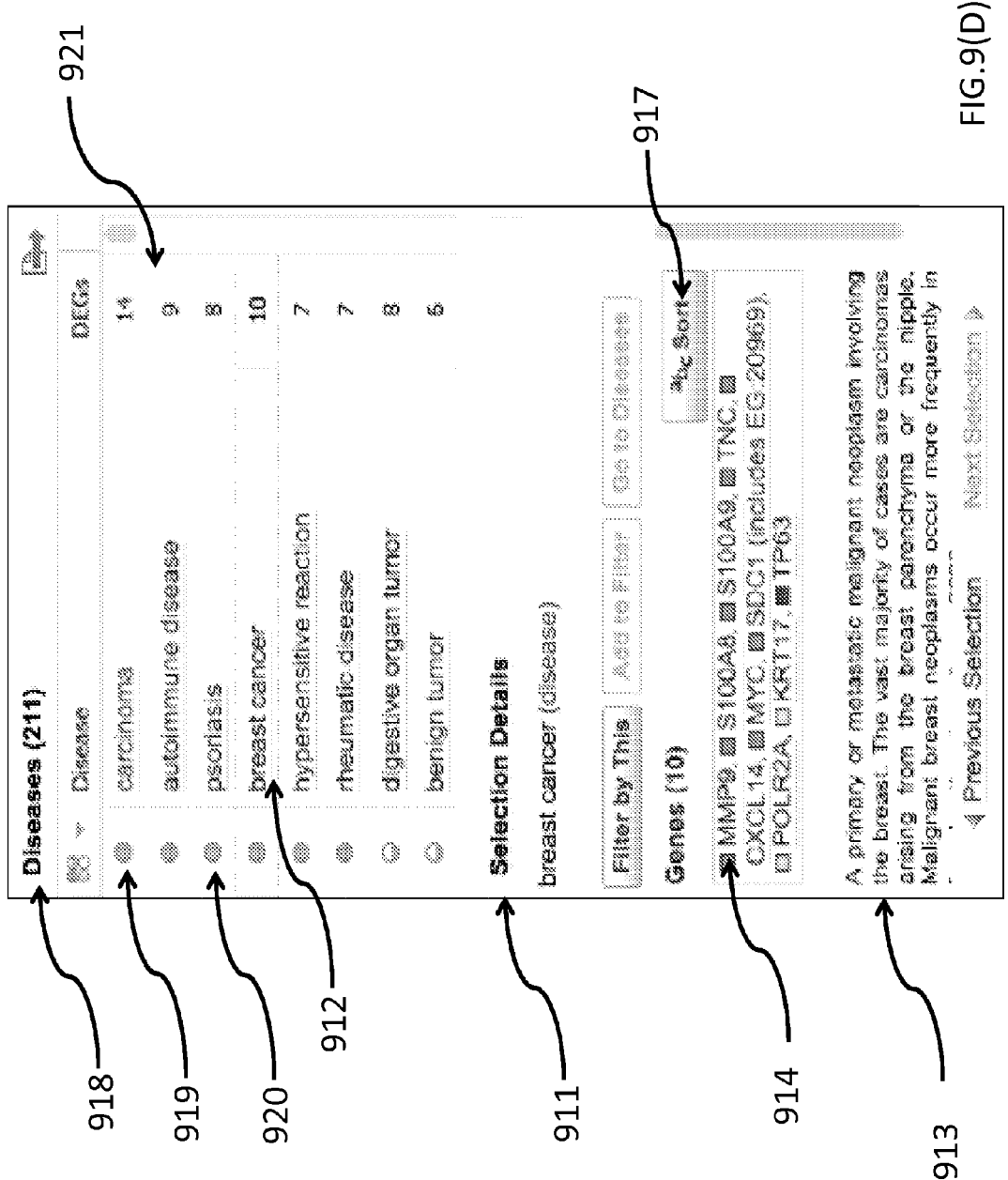
FIG. 9(D) depicts an embodiment of the "Diseases" module illustrating the graphical user interface showing the data by the diseases found to be associated or caused by the data 918 and details about the user selected data point 911.

For another example, a "Selection Details" window FIG. 9(D), 911 provides additional information about a selected disease or a selected data point/member for example 912. The disease associated additional information displayed in the "Selection Details" window is selected from a list comprising a ranking score, a disease-related list of data points/members from the user provided data set, optionally accompanied with an icons visualizing each member of the list 914, a description of the disease and other relevant information 913. In some aspects of the invention, the disease-related list of data points/members from the user provided data set can be sorted by selecting a sort button 917. The sorting can be performed according to various criteria, including, but not limited to, for example, the expression fold change, alphabetical or another attribute associated with the user provided experiment.

A disease graph FIG. 9(B), 903 displays the data points/members of the user provided data set using data icons. In various aspects of the invention, the displayed data points/members are a remaining subset of the user provided data set after the application of one or more filters. Various visual metrics can be used to display relevant attributes on the data icons 907. A highlighted text style can be used as a visual metric to identify the data points/members associated with a selected disease. The selected data icons are optionally displayed with a border in a different color than the rest of the data icons 904. In some aspects of the invention, the border color and the text highlighting color are the same.

A visualization window explains used visual metrics FIG. 9(C), 906. In a particular embodiment, up to four circles within a data icon display up to four attributes related to the associated data point/member 908. In some aspects of the invention, more attributes are displayed in association with the icon. In some aspects of the invention, the circles have different colors from each other 908. In some aspects of the invention, circles displaying a certain attribute have a designated location within the data icon. As an example, a pink "biomarker" circle appears in the upper left corner of a data icon, when the associated data point/member is a biomarker. Other optional attributes include but are not limited to mutation, isoform, SNP (single nucleotide polymorphisms), drug target and gene expression. In other embodiments, optional attributes include but not limited to mutation on a particular strand of DNA, isoform, SNP (single nucleotide polymorphisms), siRNA. miRNA or drug target.

In various aspects of the invention, additional windows in the "Diseases" view, provide further information or enable the entry of further information. For example, the "Notes" window 909, provides a method for a user to enter information and link it to a particular data point/member. In some aspects of the invention, the user entered notes are carried through to other views of the data analysis package. Notes can be activating for user entry by clicking on the "Add Notes" button, 910.

Figure 9E:
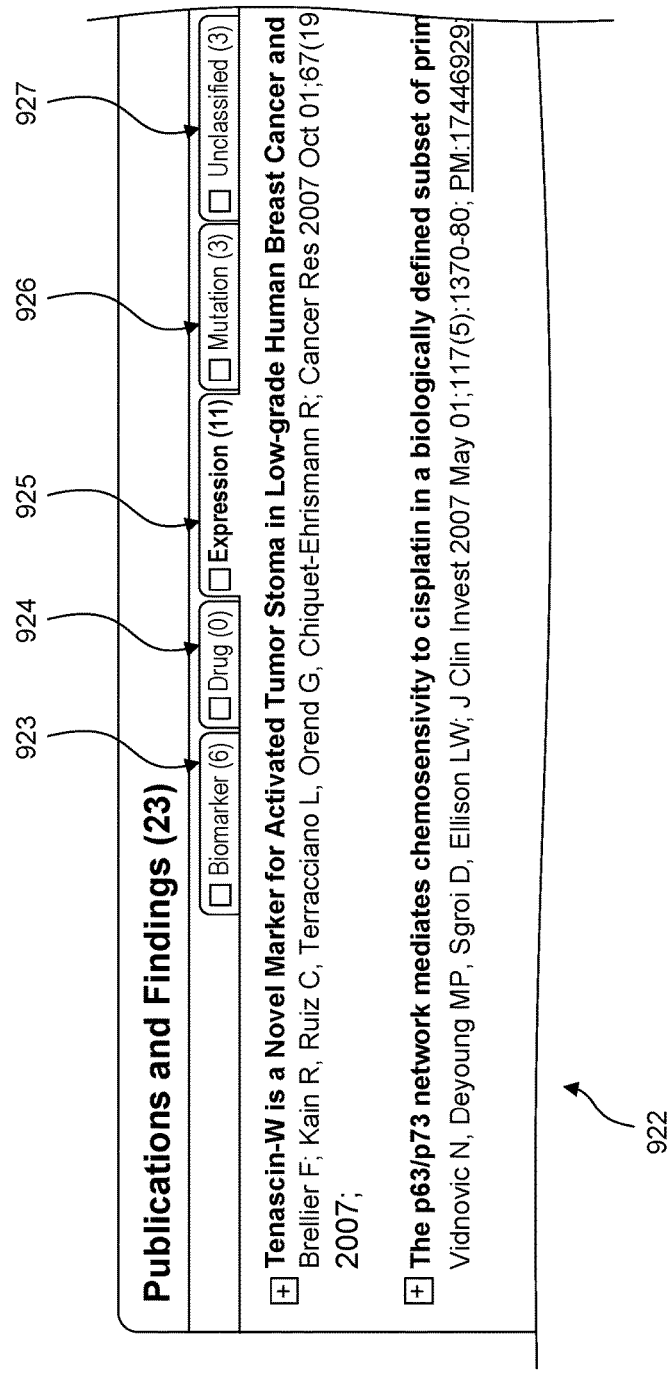
FIG. 9(E) depicts an embodiment of the "Diseases" module illustrating the graphical user interface "Publication and Findings" on the literature that supports the data point selected by the user 922.

In various aspects of the invention, an additional "Publications and Findings" window FIG. 9(E), 922 lists and optionally links to publications related to the disease. In some aspects of the invention, publications that are specifically related to disease-related data points/members from the user provided data set will be prioritized. In some aspects of the invention, the publications are sorted according to the type of information they provide, for example, publications can be grouped under a biomarker 923, a drug 924, an expression 925, a mutation 926, or an unclassified tab 927 for providing the tab-relevant information. In some aspects of the invention, the publications are sorted under additional criteria include but not limited to mutation on a particular strand of DNA, isoform, SNP (single nucleotide polymorphisms), siRNA or drug target.

Figure 10A:
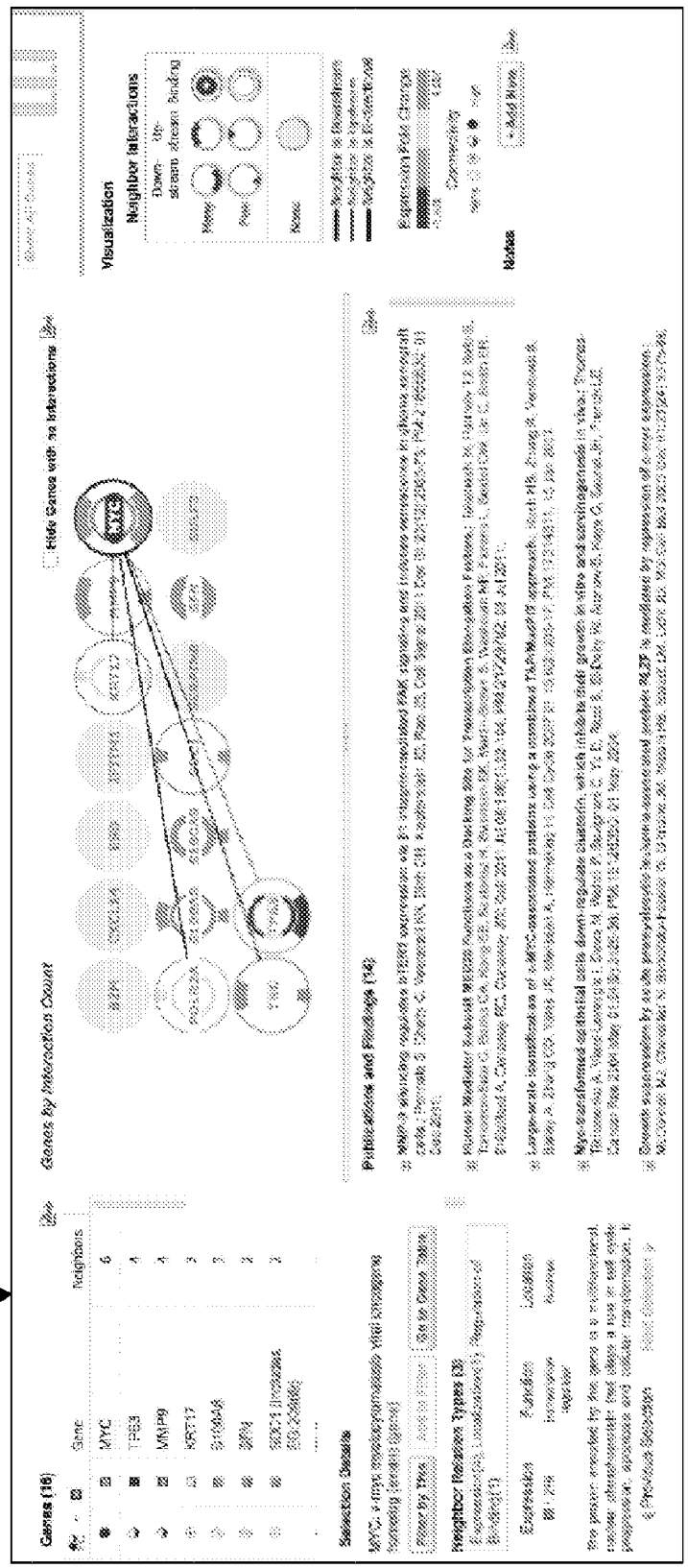
FIG. 10(A) depicts an embodiment of the system illustrating the graphical user interface being accessed by a user in "Interactions" view 1001.

Referring now to FIG. 10(A) a diagram of another aspect of the system in this particular embodiment, constructed in accordance with the present invention is illustrated. FIG. 10(A) displays the "Interactions" view 1001. According to embodiments of the invention, the "Interactions" view 1001 is accessed by selecting the view selection icon FIG. 4(B), 426 "Interactions". In various embodiments of the invention, the "Interactions" view visualizes the molecular or proteins interactions that the data points/members of the user provided data set are involved in. In various aspects of the invention, the interactions are compiled from an database linked to the data analysis package. In various aspects of the invention, the interactions comprise interactions that are associated with the remaining data points/members after one or more filter applications. Filter for a particular gene of interest can be selected by hovering the mouse pointer over a gene icon or clicking on 1003. For example, Interaction associated with the filtered gene are viewed by the use of connecting lines as shown in 1002 or optionally by other visual indicators such as colors and/or various shapes. Up-stream and down-stream interactions can be visualized by the use of various icons. For example, crescent shapes at the top, 1006 or bottom, 1005 of a circle can be used to indicate and up-stream or down-stream interaction with the selected/filtered data point. In another aspect of the invention color lines can indicate neighbor that are down-stream, upstream, bidirectional or neighbor which the data point is directly bound to. The length of the crescent can be used to indicate number of interactions for a particular gene. For example a longer crescent can indicate many interactions are known with that particular gene 1005. While a shorter crescent would indicate that there are few interactions associated with that particular gene, as shown in 1004. Also the color of the crescent can also impart additional information on the gene. For example the color can indicate ranking information or expression fold change for a data point/member. In one embodiment the color of the crescent indicates expression fold change as defined a visual metric associated with the icon 1007. In another example, the color of the crescent indicates the degree of connectivity as defined a visual metric associated with the icon. The isoform icons, for example 544, can be presented as a visual icon and can include a visual metric showing the number of specific isoform annotations.

According to embodiments of the invention, the "Interactions" view visualizes the previously known interactions of the data points/members of the user provided data set from an ontological database. In some aspects of the invention, the interactions comprise upstream or downstream members in a pathway. In some aspects of the invention, the interactions comprise binding partners. Additional information may include, but is not limited to neighbors of a gene.

In various embodiments of the invention, a list provides the names of the data points/members from the user provided data set. In some aspects of the invention, the data points are individual genes. In some aspects of the invention, the data points are designated by a code for the dataset. In some aspects of the invention, the code allows the retrieval of the individual data points from a database. In some aspects of the invention, the list includes a remaining subset of the data points in the user provided data set after the application of one or more filters.

The "Interactions" view, in various aspects of the invention, provides a table with a list of the individual data points in the user provided data set 1023. In some aspects of the invention, the table provides additional information about each data point in the list. In various aspects of the invention, the additional information is related to the interactions of the data point, for example ranking 1012 and the degree of connectivity 1015. In some aspects of the invention, the displayed interactions follow the definitions in an ontological database. In some aspects of the invention, the additional information comprises the number of each type of interaction (e.g. upstream, downstream, binding, neighbor etc.). In some aspects of the invention, the additional information comprises data from the user provided data set. For example, an icon associated with each data point may display information regarding the degree of relative expression in the list 1016, wherein the gene expression is informed from the user provided data set. A visual metric, such as color may be used as exemplified in 1016. Optionally, the visualization window can provides a means to the use to change at least a portion of the visualization options.

Figure 10B:
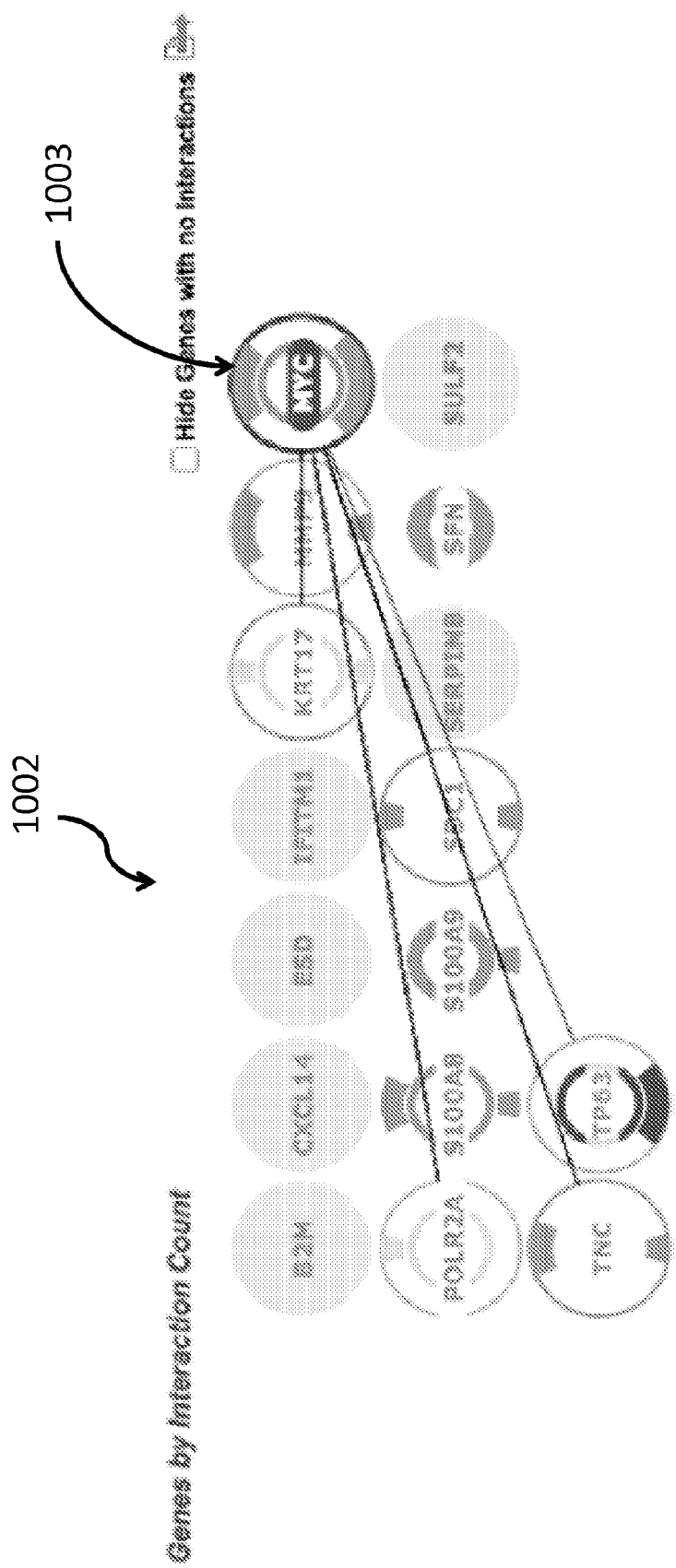
FIG. 10(B) depicts an embodiment of the "Interactions" module illustrating the graphical user interface displaying user supplied data by molecular interactions 1002.
Figure 10C:
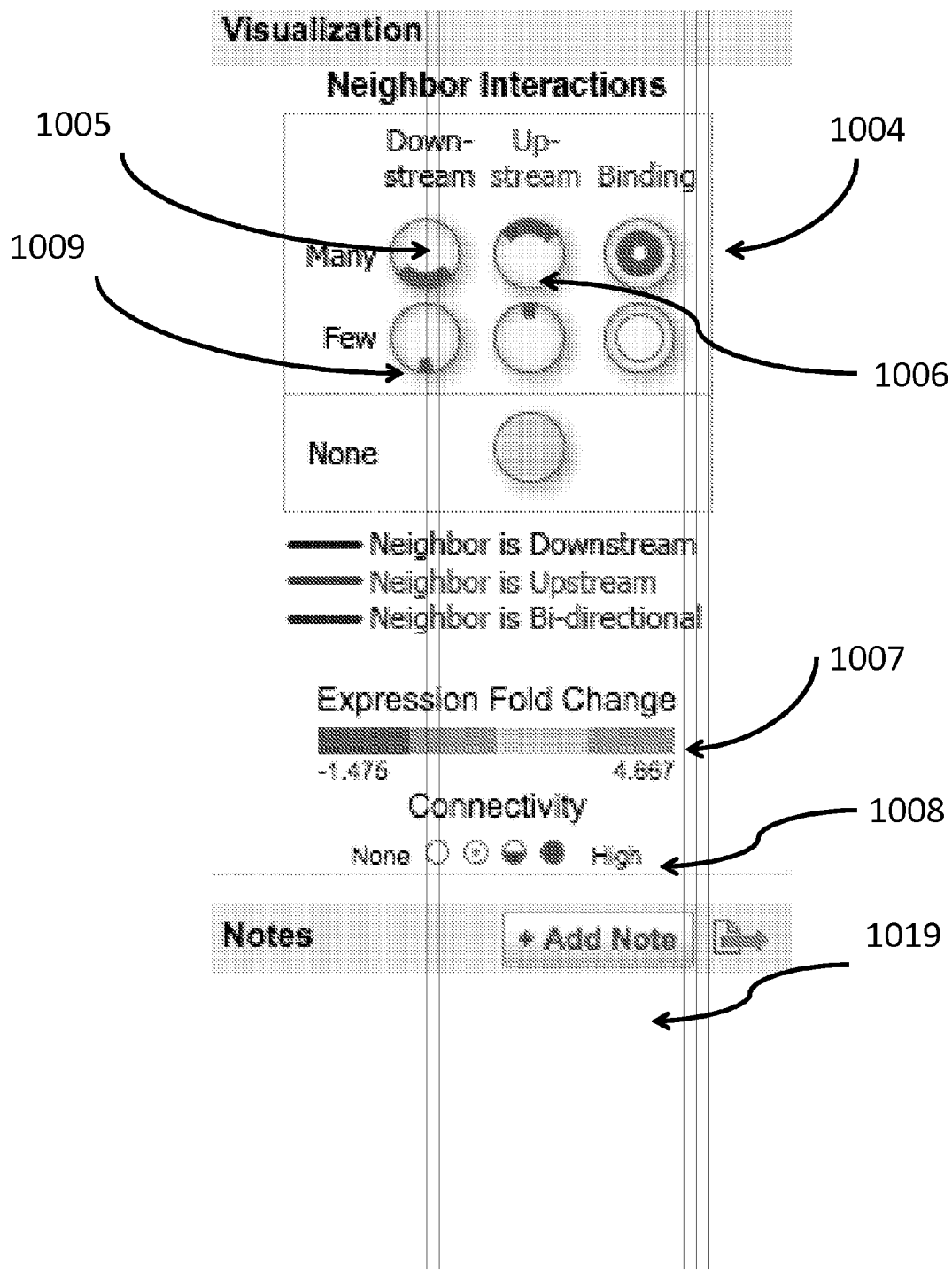
FIG. 10(C) depicts an embodiment of the "Interactions" module illustrating the graphical user interface to visualize molecular interaction and relationship 1004 and an embodiment illustrating the Notes field 1019.
Figure 10D:
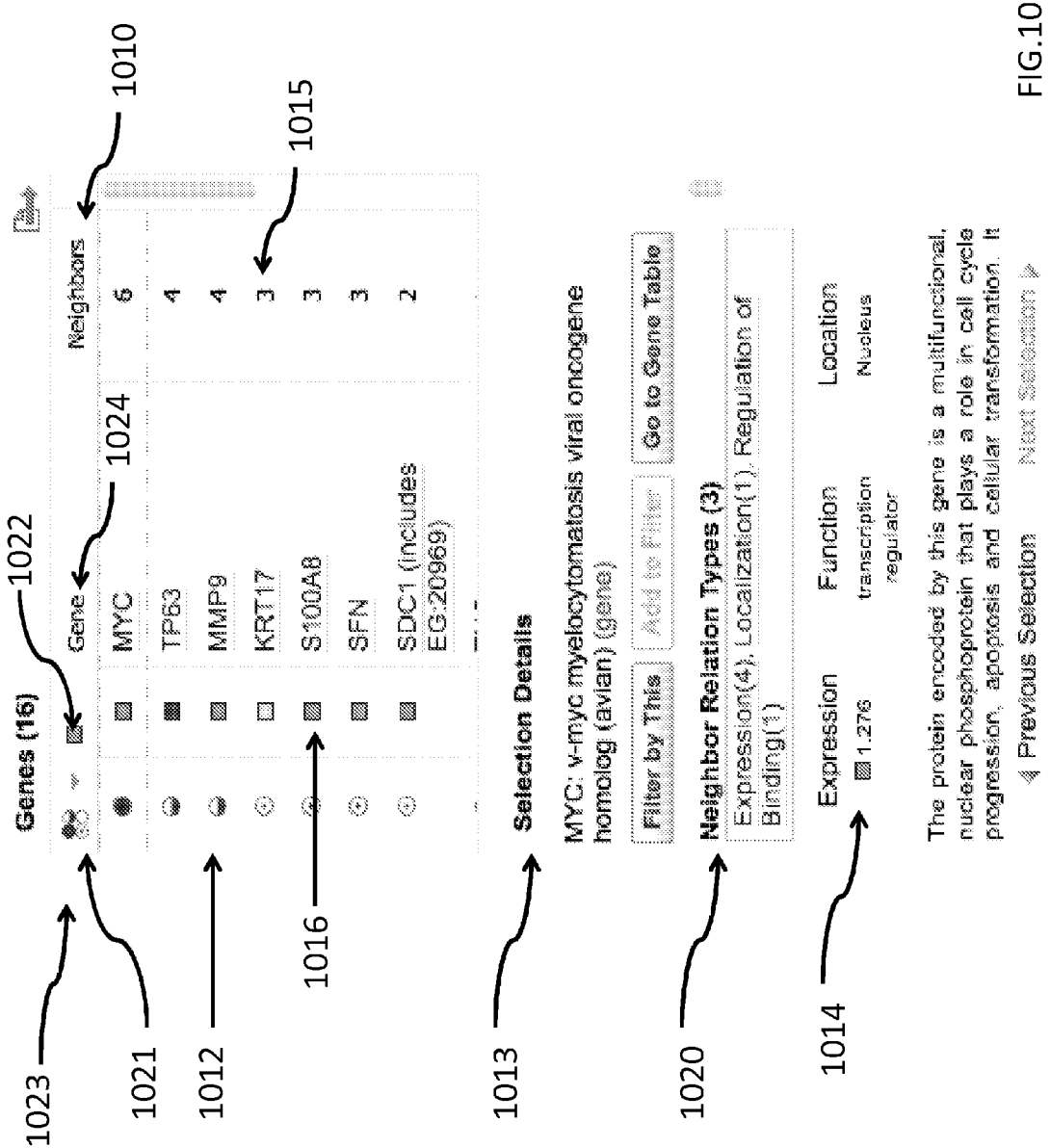
FIG. 10(D) depicts an embodiment of the "Interactions" module illustrating the graphical user interface showing the user supplied data by molecular interactions 1023 and details of a data point selected by the user 1013.

In this particular embodiment FIG. 10(B), an upper arch and a lower arch are used as visual metrics on the data icons to visualize the number of upstream and downstream interaction partners, wherein the arch length is indicative of the respective numbers. A pull-down menu can allow a user to select a criterion to accordingly color fill the data arches through a computer mediated interaction. By way of example, the criterion to apply a particular visual metric is selected from gene expression levels or other user provided experimental data input, the number of diseases that are associated with a data point (e.g. gene), the number of processes that are associated with a data point (e.g. gene), the number of pathways that are associated with a data point (e.g. gene), or the number of interactions that are associated with a data point (e.g. gene). Thus, In some aspects of the invention, the visual metrics are dynamically assigned to display desired properties customizing the interactions graph for enhanced visualization and analysis of the user provided data set. The visualization window can include a legend, mapping the colors used as visual metrics associated with various types of icons to values they represent. In various aspects of the invention, the range of the represented values is a property of the user provided data set. The mapping of the colors to values within that range is optionally adjusted dynamically to display the various values with higher sensitivity. A second legend can map a second visual metric to a second set of values. In this particular example, the icon fill-in style is representative of a ranking value displayed on the process icons. The mapping of visual metrics to value ranges can be linear, exponential, logarithmic or follow any function that is suitable for the visualization of a value In various aspects of the invention, the individual data points may be ranked. By way of example, an interaction ranking may be based on the number of interactions the data point is involved in, the number of interactions its interaction partners are involved in, and the particular connectivity of its interaction network, wherein the interactions are made inside or outside the user provided data set.

In some aspects of the invention, an interaction icon is displayed associated with each data point in an interactions table for example 1012 or 1016. Optionally, the icon can be used to visualize a particular qualitative or quantitative attribute associated with each data point in the list. The visualized attribute displayed by the interaction icon can for example be the level of ranking of a particular data point within the list of data points in a list, the number of interactions the data point is involved in, the number of interactions its interaction partners are involved in, and the particular connectivity of its interaction network, wherein the interactions are made inside or outside the user provided data set.

A visual metric associated with the icon enables the display of the attribute. In this particular embodiment, the visual metric is a color fill style for example, 1008. Optionally, methods to sort the interactions table are provided by selecting the table title area for example 1024 or 1010. By way of example, selecting the upstream interactions column title "Up" is used to sort the data points according to the number of upstream interaction partners, selecting the downstream interactions column title "Down" is used to sort the data points according to the number of downstream interaction partners, selecting the binding interactions column title "Bind" is used to sort the data points according to the number of binding interaction partners, selecting the neighbors column title "Neighbors", 1010 is used to sort the data points according to the number of neighbors interaction partners, selecting the data point column title "Gene", 1024 is used to sort the data points according to the names of the data points, selecting the interaction icon column title is used to sort the data points according to the an attribute, the interaction icon is displaying (e.g. gene expression level) and selecting the ranking icon is used to sort the data points according to their rank within the table 1021 or 1022.

An interactions graph displays the data points/members of the user provided data set using data icons. In various aspects of the invention, the displayed data points/members are a remaining subset of the user provided data set after the application of one or more filters. Various visual metrics can be used to display relevant attributes on the data icons. A highlighted text style can be used as a visual metric to identify a selected data icon. The selected data icons are optionally displayed with a border in a different color than the rest of the data icons. In some aspects of the invention, the border color and the text highlighting color are the same. In some aspects of the invention, the border color is used as a visual metric to display an interaction-related attribute (e.g. an interaction ranking).

In various aspects of the invention, additional windows in the "Interactions" view, provide further information or enable the entry of further information. For example, the "Notes" window, 1019 provides a method for a user to enter information and link it to a particular data point/member. In some aspects of the invention, the user entered notes are carried through to other views of the data analysis package. For another example, a "Selection Details" window 1013 provides additional information about a selected data point/ member or group of data/points/members. In some aspects of the invention, the group is defined by interaction relationships (e.g. a network of interactions), 1020. The data point associated additional information displayed in the "Selection Details" window can be selected from a list comprising a ranking score, for example 1012 or 1014 or both, a interaction-related list of data points/members from the user provided data set, optionally subdivided by the type of interaction, optionally accompanied with an icons visualizing each member of the list, a description of the interaction and other relevant information. In some aspects of the invention, the interaction-related list of data points/members from the user provided data set can be sorted by selecting a sort button. The sorting can be performed according to various criteria, including, but not limited to, for example, the expression fold change 1022, connectivity 1021, gene name 1024, number of neighbors 1010, fold change in expression 1103, or user notes 1104, or another attribute associated with the user provided experiment.

In various aspects of the invention, an additional "Publications and Findings" window lists and optionally links to publications related to the set of data points/members and their interactions. In some aspects of the invention, publications that are specifically related to interactions between data points/members from the user provided data set will be prioritized. In some aspects of the invention, the publications are sorted according to the type of information they provide.

Referring now to FIG. 11(A), a diagram of another aspect of the system in this particular embodiment, constructed in accordance with the present invention is illustrated. FIG. 11(A) displays the "Gene Table" view 1101. According to embodiments of the invention, the "Gene Table" view 1101 is accessed by selecting the view selection icon FIG. 4(B), 427. In various embodiments of the invention, the "Gene Table" view visualizes detailed information about the data points/members of the user provided data set. In various aspects of the invention, the information is compiled from a database linked to the data analysis package. In various aspects of the invention, the information comprises information that are associated with the remaining data points/ members after one or more filter applications.

According to embodiments of the invention, the "Gene Table" view visualizes the previously known interactions of the data points/members of the user provided data set from an ontological database. In various aspects of the invention, the "Gene Table" view comprises a summary table for information visualization FIG. 11(B), 1102 and 1117. In some aspects of the invention, the types of summary information on the summary table include any of the previously discussed types of information. In some aspects of the invention, the information comprises a summary of the information displayed in the other views of the data analysis package. In some aspects of the invention, the information comprises user entered input. In some aspects of the invention, the information comprises user entered "Notes". In some aspects of the invention, a column of the table lists the number of "Notes" for each data point.

In various embodiments of the invention, a summary table on the "Gene Table" view provides the names of the data points/members from the user provided data set. In some aspects of the invention, the data points are individual genes 1102. In some aspects of the invention, the data points are designated by a code for the dataset. In some aspects of the invention, the code allows the retrieval of the individual data points from a database. In some aspects of the invention, the list includes a remaining subset of the data points in the user provided data set after the application of one or more filters.

The "Gene Table" view, in various aspects of the invention, provides a table with a list of the individual data points in the user provided data set. In some aspects of the invention, the table provides summary information about each data point in the list. In various aspects of the invention, the summary information is related to the name 1102, function 1105, localization 1106, molecular pathways 1107, biological processes 1108, diseases 1109, specific isoforms annotations (FIG. 11(E), 1118), and/or the number interactions associated 1110 with the user supplied data. In some aspects of the invention, the summary information is related to user provided information. The user provided information may comprise values/measurements from a user experiment. In some aspects of the invention, the user provided information comprises information that are supplementary in nature to the information contained in a database model of the biological system accessed by the data analysis package. In some embodiments the displayed information is the number of the relevant information (e.g. the number of interactions, pathways, diseases, processes, diseases, "Notes" etc.). In some aspects of the invention, the summary information comprises data from the user provided data set. For example, an icon associated with each data point may display information regarding the expression of a gene in the list 1103, wherein the gene expression is informed from the user provided data set. A visual metric, such as color may be used to indicate the degree of gene expression.

In various aspects of the invention, the individual data points may be ranked for example FIG. 11(C). By way of example, the ranking algorithm can be informed by one or more attributes that are included as summary information.

Optionally, methods to sort the summary table are provided. In some embodiments the summary table is sorted by selecting the table title area of the column that informs the sorting. For example but selecting 1103, 1104, 1105, 1106, 1107, 1108, 1109, and 1110 the summary table is sorted based on that criteria.

Figure 11D:
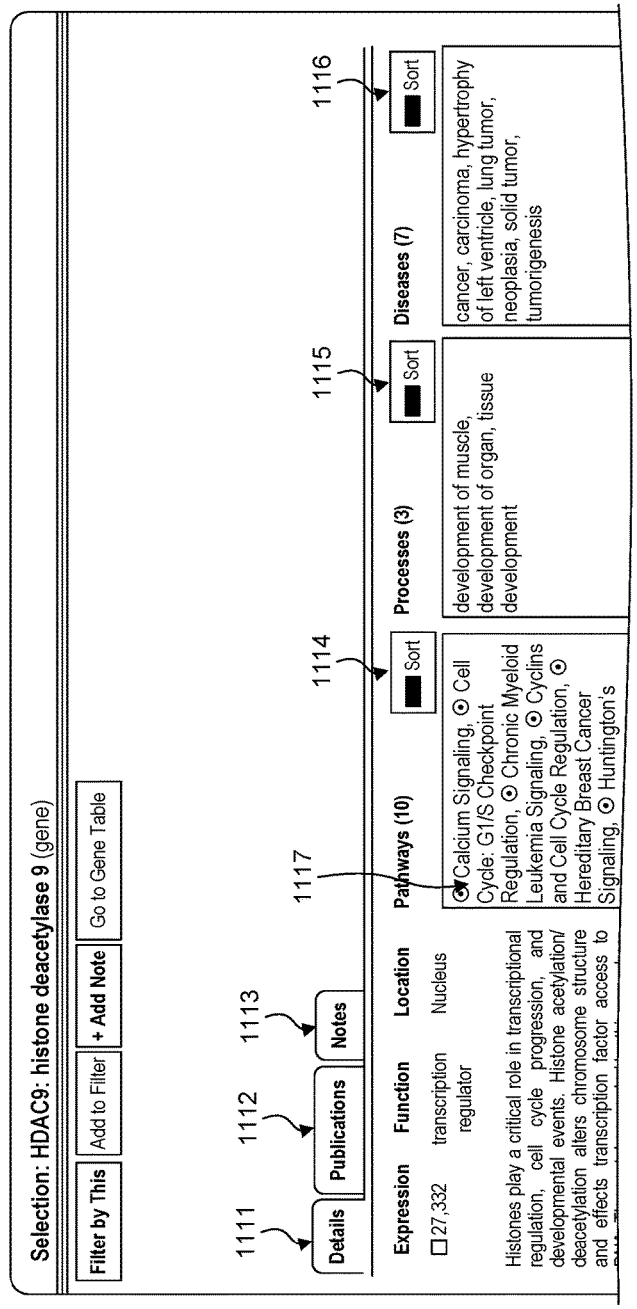
FIG. 11(D) depicts an embodiment of the "Gene Table" module graphical user interface, where the user can view the details of each data point in the report provided by the system 1111.

For another example, a "Selection" window FIG. 11(D) provides additional information about a selected data point/member, group of data/points/members or other entries in the summary table. The "Selection" window may be further divide into user activated tabs such as "Details" 1111, "Publications" 1112 and "Notes" 1113 tabs that provide further detail on the data point selected from the Gene Table module. The "Details" window provides information on pathways, biological processes and diseases on the data point selected. In addition each pathway, process and disease in the "Details" window can be ranked. In the "Details" window there can be sort buttons provide to the user. High and low ranking for each member in a list can be visualized by using a visualization metric for example using various colors, various degrees of fill in, 1117 or numerical values to indicate a high or low ranking.

In various aspects of the invention, an additional "Publications" window FIG. 11(D), 1112 lists and optionally links to publications related to the set of data points/members. In some aspects of the invention, publications/references that are specifically related to remaining subset of the user provided data set, after the application of one or more filters, will be prioritized. In some aspects of the invention, publications/references will be chosen to refer to particular data points/members. In some aspects of the invention, the publications are sorted according to the type of information they provide. Methods to prioritize publications/references are provided including selecting a focus for the publications/references by a computer mediated interaction with the data analysis package. In some aspects of the invention, the computer mediated interaction comprises selecting entries of the summary table.

Figure 11E:
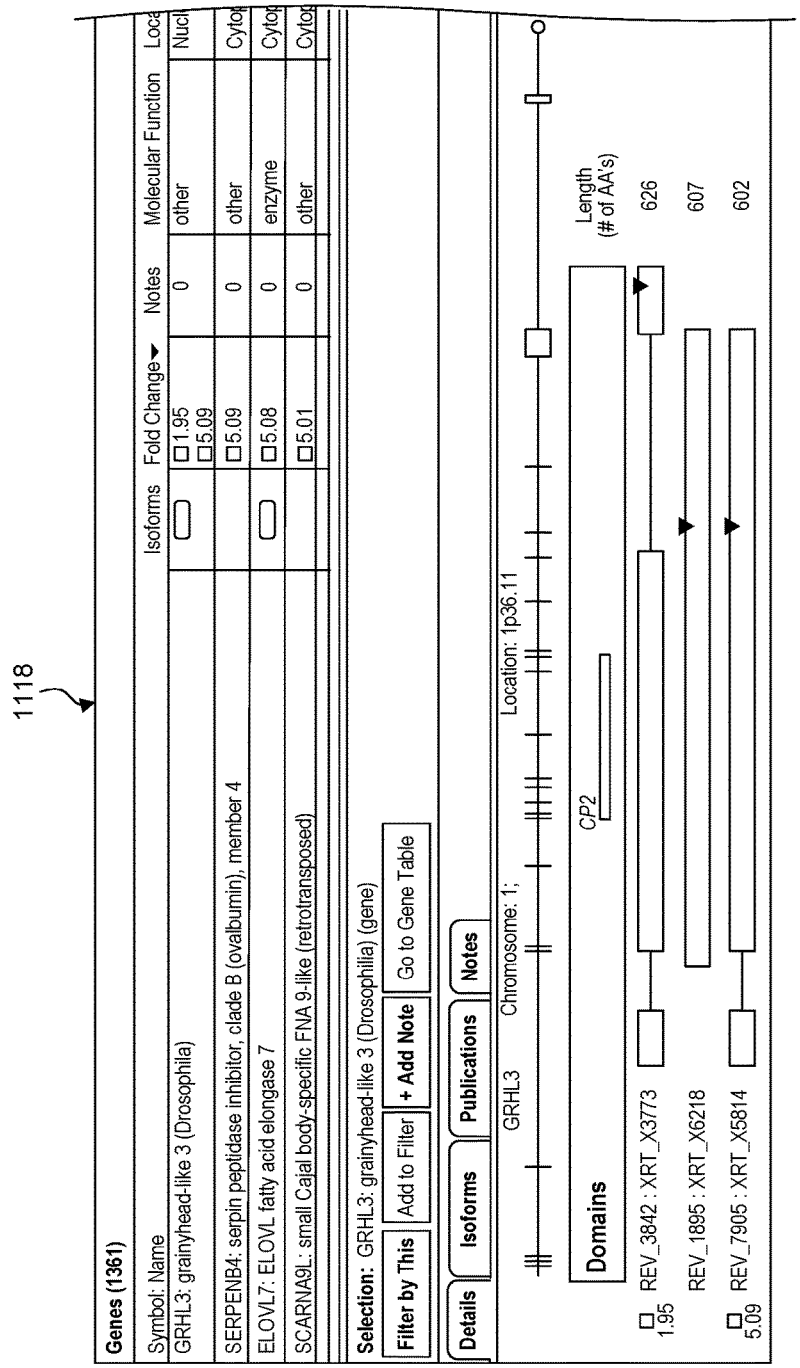
FIG. 11(E) depicts an embodiment of the "Gene Table" module graphical user interface, where the user can view the details of an isoform specific view showing the annotations of the genes from the user supplied data provided by the system 1118.

FIG. 11(E) illustrates an isoform specific view of the data according to some embodiments of the invention. In one aspect of the invention an isoform window contains a table displaying a user graphical interface with isoform specific annotations on genes, where relevant, to the user supplied data. In one aspect of the invention, the "Details" tab displays gene details and isoform specific annotations. A "Publication" tab may list all or a subset of the relevant publications for a selected gene or genes, for example, with a feature that will allow you to sort the isoform specific publications and findings. In one aspect of the invention, the "Notes" tab is provided and may list the number of available notes or insights for a selected data point. The isoform icons, for example 544, and isoform view 1118 may be provided with any module in the system. The isoform view FIG. 11(E) configured for activation in any module (e.g. "Summary" 501, "Gene Wheel" view 601, "Pathway" 701, "Processes" 801, "Diseases" 901, "Interactions" 1001, and "Gene Table" 1101), for example by activating the isoform icon within the view window. For example from the "Summary" view table in FIG. 5(B), activating an isoform icon 544 may open the isoform view, for example FIG. 11(E), 1118, displaying an isoform table.

In various aspects of the invention, additional windows in the "Gene Table" view, provide further information or enable the entry of further information. For example, the "Notes" window 1113 provides a method for a user to enter information and link it to a particular data point/member. In some aspects of the invention, the user entered notes are carried through to other views of the data analysis package. The notes entered by the user in each view FIG. 4(B), can be access in the Gene Table View by clicking on the data point of interest and then selecting the "Notes" tab.

Figure 5B:
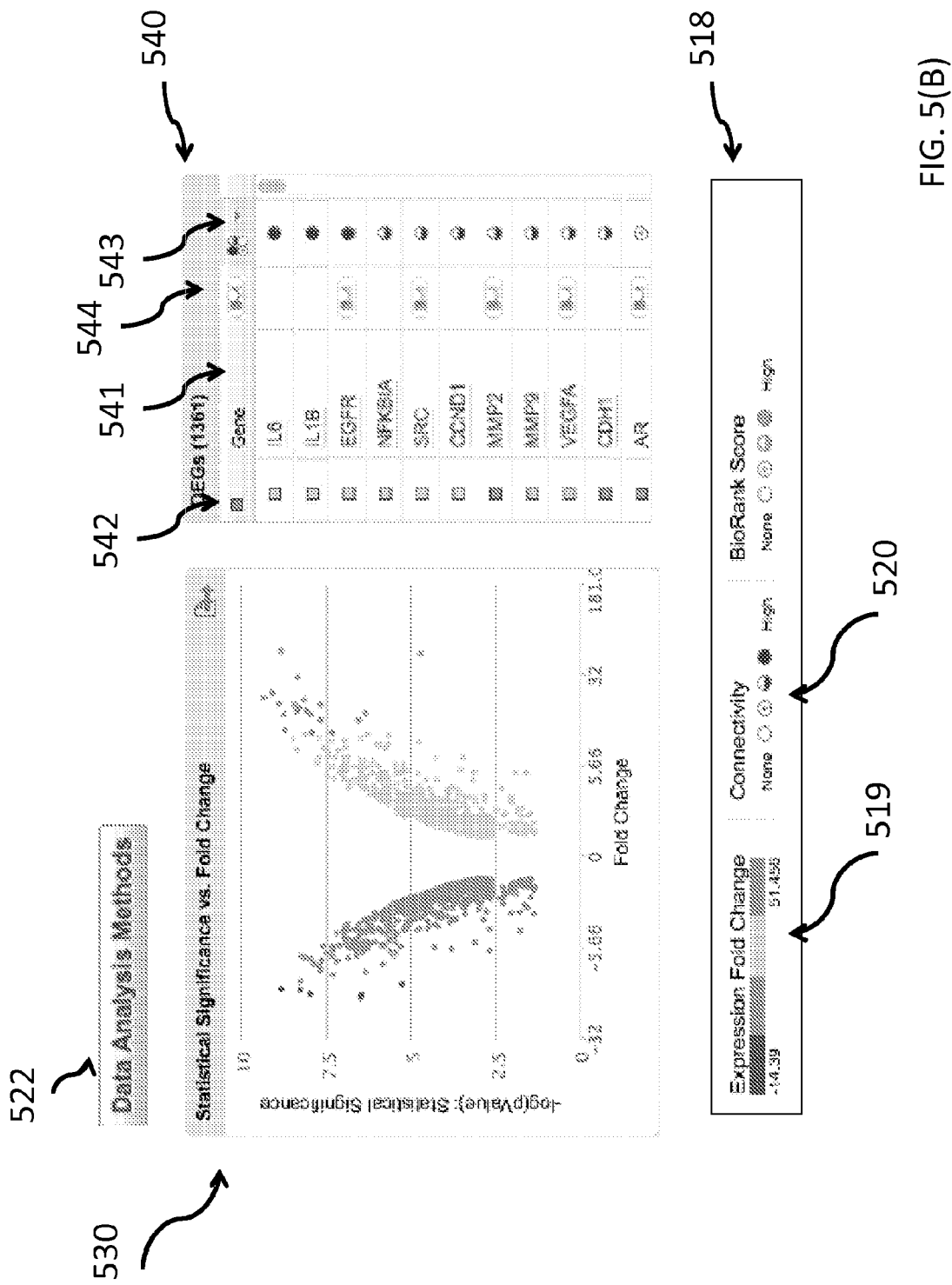
FIG. 5(B) depicts an embodiment of the "Summary" module illustrating the graphical user interface volcano plot 530 and DEG (differential gene expression) gene of the user supplied data 540.
Figure 12:
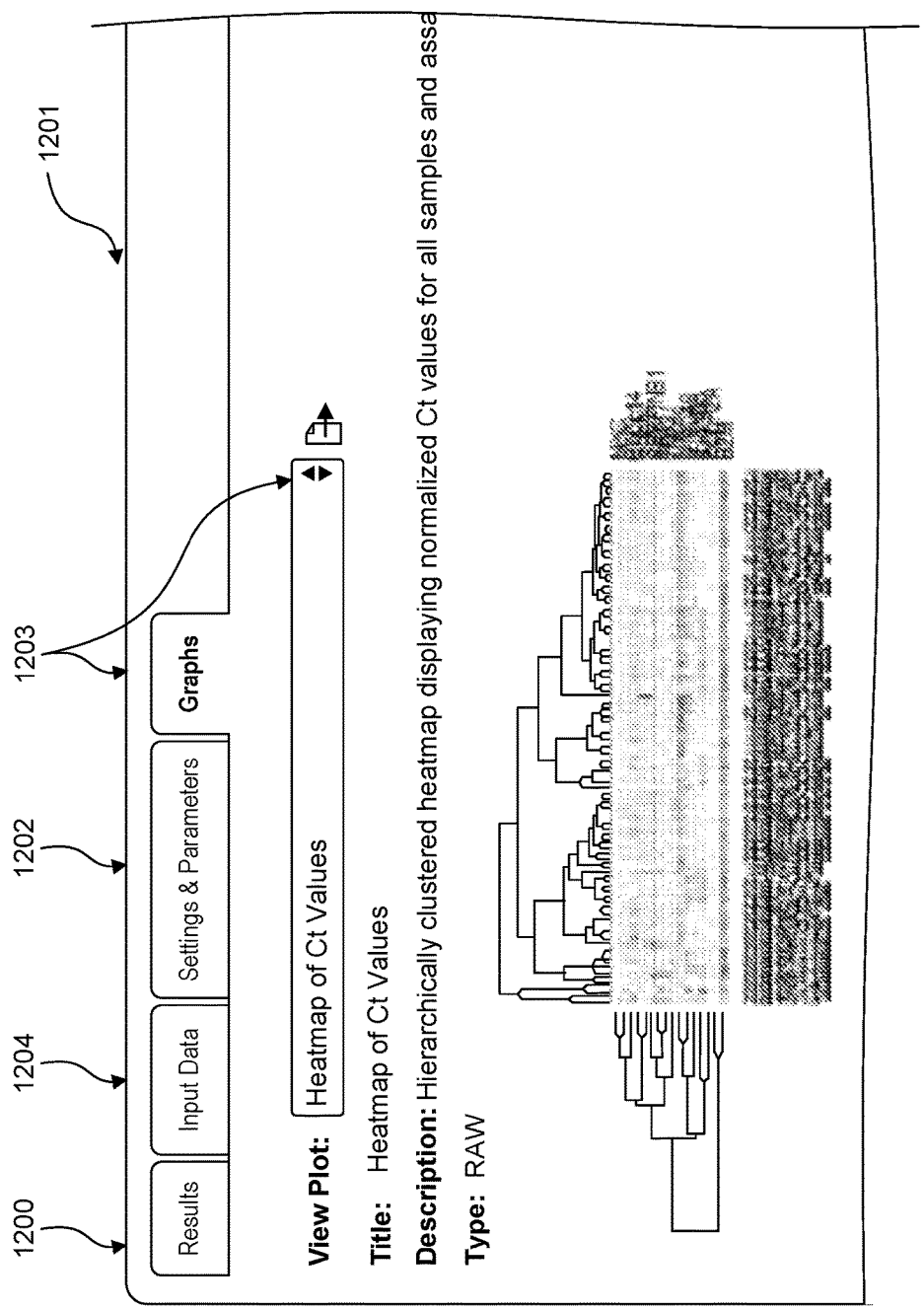
FIG. 12 depicts an embodiment of the "Quality Metrics" module illustrating the graphical user interface being accessed by the user.

A user can click on a "Data Analysis Methods" button, FIG. 5(B), 522 to examine the methods and statistics used to generate the report. FIG. 12 depicts an embodiment of a Quality Metrics module. The methods and tests used by the quality metrics module will vary depending on the type of data used (e.g. whole genome sequencing, whole exome, RNA sequencing, and quantitative RT-PCR or microarray). Various statistical tests can be employed by the quality metrics module to analyze the quality of the data. For example statistical tests used by the quality metrics module can include but are not limited to sample correlation, variation measurements across samples and controls, 2D principle components and 3D principle components. This field can also display but are not limited to such metric as cut-off parameters, normalization methods use, false discovery rate (FDR) statistical method used, and correlation with other experimental data sets. In one aspect of the invention the quality metrics module report can include graphs to help the user determine the quality of their uploaded data.

In one embodiment the quality metrics module can include a gene search function. For example, a user would enter a gene name or symbol such as "MYC" into a search field. All the data including the myc gene would be retrieved from the system and displayed in a gene summary table. Optionally, the quality metrics module can include a results field. The results field displays a table containing various parameters from the analysis including but not limited to gene name, p-values, fold change, isoforms, and/or universal gene ID number.

In some aspects of the invention, the data analysis package comprises one or more data processing modules. In some aspects of the invention, the data processing module processes the user provided data set and outputs a processed data set. In some aspects of the invention, the data processing comprises a statistical analysis. The statistical analysis comprises, by way of example, analyses calculating statistical parameters comprising a mean, standard deviation, skewness or any mathematical moment for the data set or a portion thereof. The statistical analyses may relate to comparative analysis between data sets or between portions of a data set. In some aspects of the invention, new values are assigned to members/data points in a data set as a function of the calculated statistical parameters. In some embodiments the data set is normalized. In some aspects of the invention, a first processing module provides an output in a different format than the input. In some aspects of the invention, a processing module or another module in the data analysis package is equipped to accept the output from the first processing module.

Output in some aspects, the invention relates to visualizing a data set and a plurality of features related to the data set. In some aspects of the invention, the invention relates to a graph comprising icons and at least one visual metric associated with the icons to visualize a data set on a graphical user interface. The icons on the interface are displayed in a fashion to convey information about one or more attributes related to the data set. A preferred attribute to be represented visually on an icon is a value associated with the measurements in the data set. Other attributes comprise the degree of association with one or more features. In some aspects of the invention, the features are represented by a second set of icons on the graph. In some aspects of the invention, the features are obtained from the ontological database. In some aspects of the invention, the features are filtered to a subset of features based on the content of the data set. In some aspects of the invention, the features are biological properties. In some aspects of the invention the data set is a biological data set and the database comprises relationships between the biological data set and biological properties related to the biological data set.

Biological properties in some aspects of the invention, the database relates features and one or more data contents comprised in a data set. In some aspects of the invention, the data sets comprise one or more biological contents. In some aspects of the invention, the features comprise biological properties. In various aspects of the invention, the biological properties comprise biological pathways, biological processes, biological or chemical functions, cellular locations, phenotypes, associations with diseases or disease states, locations within a genome, co-expression profiles, co-localization profiles, associations with tissues, associations with developmental stages and networks.

In various embodiments the database provides a model of a biological system from a molecular perspective. In some aspects of the invention, the database is a relational database. In various aspects of the invention, the database provides linkages from the user provided data set to biological properties, and optionally between biological properties within the biological system. In some aspects of the invention, the database is hosted on a remote server. In some aspects of the invention, the database is installed on site or optionally on a computer that is directly accessed by a user of the data analysis package. Optionally, the database provides methods to search for aspects of one or more models of one or more biological systems. In some aspects of the invention, the database is amended by a user. Methods and systems related to ontological databases are described in PCT/US07/74663, 60/820,773, 60/725,949, 60/725,948, 60/725,936, 60/725,931, 60/725,898, 60/725,895, 60/725,890, 60/725,889, 60/725,888, 60/725,887, 60/725,766, 60/725,737, 60/725,734, 60/725,732, 60/725,676, 60/647,301, 60/618,082, 60/617,990, 60/617,987, 60/617,980, 60/617,967, 60/617,966, 60/617,932, 60/617,913, 60/617,908, 60/617,850, 60/617,828, 60/617,811, 60/617,799, 60/617,788, 60/617,730, Ser. Nos. 13/029,089, 11/829,784, 10/864,163, 10/802,615, 10/770,864, 10/632,099, 10/502,420 which are herein incorporated by reference.

Visual metric in some aspects, the invention relates to icons and at least one visual metric associated with the icons to visualize a data set on a graphical user interface. The icons on the interface are displayed in a fashion to convey information about one or more attributes related to the data set and the attributes obtained from an ontological database. A visual metric marks an icon to designate a distinguishable identity to the icon. In some aspects of the invention, the visual metric is representative of a qualitative attribute. In other embodiments, the visual metric is representative of a quantitative attribute. In various aspects of the invention, the quantitative attribute assumes continuously changing values. A preferred visual metric representing such an attribute is also able to assume continuously changing values. In a computerized digital environment, a continuously changing value is converted to a close digitized value.

Various embodiments of the invention use one or more visual metrics to mark an icon or a portion of an icon. By way of example, the portion of an icon comprises one or more edges, corners, areas and lines within. In some embodiments one or more shapes, colors, color hues or shadowing applications are used as visual metrics. Various embodiments use one or more dimensions associated with an icon or a portion of an icon as a visual metric. Other uses of visual metrics marking an icon include, by way of example, the location of the icon in the graph. In various aspects of the invention, particular locations on a graph are designated to icons with particular attribute values. In some aspects of the invention, the designated locations associated with particular attribute values are recognized, but change their absolute positions on the graph. In various aspects of the invention, further visual metrics are used to recognize the identity of the attribute associated with designated locations. In some embodiments a distance from one or more designated locations on the graph is used as a visual metric. In some embodiments icon to icon distance is used as a visual metric. Various embodiments group/cluster icons. Icons within a group are optionally individually linked to other icons. Methods of linking icons include, by way of example, drawing a line, an arrow or another connecting object between or passing through the icons. In some aspects of the invention, the connecting objects are marked with one or more visual metrics identifying a value for the linking attribute. Linking attributes include, by way of example, participation in a biological pathway or cellular process, biological location, association with a disease, possession of a specific function or structure or the quantity or quantities thereof. In some aspects of the invention, the connecting objects have directionality. In some aspects of the invention, one or more pieces of text are used as a visual metric/identifier.

User/Icon Interaction

In some aspects of the invention, the graph allows users to interact with the data analysis package to analyze the data set. In various embodiments one or more icons can be selected by a computer mediated interaction with the graph. Computer mediated interactions, by way of example, comprise inputs through a computer mouse, a computer keyboard, various peripheral computer devices or a script. In some embodiments an icon is selected by hovering a cursor on the display over or in the vicinity of the icon. In some aspects of the invention, one or more visual metrics associated with the icon display a change when the icon is selected. In some aspects of the invention, a piece of information related to the icon is displayed upon the selection of the icon. In various aspects of the invention, the selection comprises clicking/activating a computer mouse while the cursor controlled by the computer mouse is on or in the vicinity of the icon. In most embodiments, the cursor is considered to be in the vicinity of an object, when the object is close enough to be at least the closest selectable object to the cursor. In some aspects of the invention, a plurality of icons is selected based on combined input from peripheral computer input devices or a script.

Filters

In some aspects of the invention, the available features from a database are filtered down to a subset. In some aspects of the invention, only the filtered subset of features is represented by icons on the graph. In some aspects of the invention, the software analysis package applies a filter on the features based on the content of the data set. In some aspects of the invention, the software analysis package applies a filter on the features based on the particular constitution of the data set. Individual data points/members of the data set are analyzed by the software analysis package to determine the particular constitution of the data set. In some aspects of the invention, a filter is applied upon one of the various methods of icon selection. In some aspects of the invention, a filter is applied based on instructions from a script. In some aspects of the invention, the features comprise biological properties and the data set comprises one or more types of biological content.

In various aspects of the invention, the members/data points of the data set are filtered down to a subset. In some aspects of the invention, only the filtered subset of members/data points is represented by icons on the graph. In some aspects of the invention, a filter is applied upon one of the various methods of icon selection. In some aspects of the invention, a filter is applied based on instructions from a script. In some aspects of the invention, a filter on the members/data points is applied based on the selection of icons representing the members/data points. In various aspects of the invention, a filter on the members/data points is applied based on the selection of icons representing the features obtained from the ontological database. In some aspects of the invention, the features comprise biological properties and the data set comprises one or more types of biological content.

In various aspects of the invention, a plurality of different types of filters are applied in combination and the graph reflects the results of the filter combinations. In some aspects of the invention, the set of selectable icons are updated based on the set of active filters.

History

In some aspects of the invention, the application of various filters is recorded by the software analysis package. In some aspects of the invention, the recording is a chronological recording. In various aspects of the invention, one or more of the applied filters are displayed on a secondary graph or on a list. In some aspects of the invention, the list or the graph of filter is chronological. In some aspects of the invention, the graph or the list of applied filters comprises icons representing individual filter applications. In some aspects of the invention, one or more icons representing a filter application are selectable by any means of computer mediated user interaction. Various methods of icon selection are discussed supra.

Chronological display of filter applications allow for a historical representation of user interactions with the data analysis package. In some aspects of the invention, one or more icons representing a filter are marked by a visual metric. Various types of visual metrics and methods of marking an icon with a visual metric are discussed supra. In some aspects of the invention, a visual metric associated with an icon identifies an attribute related to the filter represented by the icon. In some aspects of the invention, the filter attribute relates to the number of the icons eliminated by the filter. In various aspects of the invention, an icon representing a particular filter in a chronological filter application list or graph is selected to remove one or more filters. In some aspects of the invention, a plurality of icons is selected. In some aspects of the invention, the filter associated with the selected icon is removed. In some aspects of the invention, the filter or filters following the selected icon are removed. Other rules for managing the filters represented by the icons based on the one or more selected icons are possible and will be obvious to the person having ordinary skill in the art.

Script

In some aspects, the invention provides methods for the use a script on the data analysis package. In some aspects of the invention, the script comprises rules governing the application of filters. In some aspects of the invention, the steps of a first user interaction with the data analysis package are recorded and exported to a script. A script generated from recorded user history allows repeating the same analysis steps during a plurality of data analysis rounds. In some aspects of the invention, the plurality of data analysis rounds use separate user provided data sets. In some aspects of the invention, a user criterion for data analysis is directly entered into a script not requiring previous interaction with the data analysis package for data analysis. In some aspects of the invention, the user criterion relates to the application of filters. In some aspects of the invention, the user criterion relates to the visualization of the data. In some aspects of the invention, the user criterion relates to rules governing the use of a visual metric. In some aspects of the invention, a script is entered through the user interface to be used in data analysis.

Filter and Script and History

According to various embodiments of the invention, the user provided data set and the associated features are filtered by a user to enhance the visualization of the data. Accordingly, a filter history is generated from the combination of the applied filters. In various aspects of the invention, the filter history is stored in the data analysis package. Optionally, the applied filter history, or a portion of it, can be extracted as an output or saved in the system. In various aspects of the invention, the system executes a script comprising instructions about a set of filters. Consequently, the user provided data set and associated features can be filtered in an automated way. In some aspects of the invention, the extracted filter history is an executable script. In some aspects of the invention, the extracted filter history is converted into an executable script. Thus, data visualization with the data analysis package of the present invention provides methods to automate data visualization.

Auxiliary Input/NLP

In some aspects of the invention, the data analysis package accepts one or more pieces of auxiliary input. In some aspects of the invention, the auxiliary input is entered in plain text. In some aspects of the invention, the auxiliary input is processed by natural language processing. In some aspects of the invention, the content of the auxiliary input is considered by a scoring algorithm in association with the user provided data set and the features associated with the data set to bias the display of the most relevant pieces of information. In some aspects of the invention, one or more features are preferentially displayed. In some aspects of the invention, a filter is applied to the data set or the features associated with the data set based on the auxiliary information. In some aspects of the invention, the data set is a biological data set and the auxiliary input comprises user criteria including the specific design of the experiment that was performed to generate the data set or the purpose or focus of the study.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1. Pathways Involved in Metastatic Progression by RNA Sequence

Breast cancer is a complex disease that is comprised of many genetic subtypes. The Claudin-Low subtype presents features of stem-cells, and might behave as tumor-initiating cells in breast cancer. They have strong EMT (Epithelial-to-Mesenchymal Transition) that confer to the cells migratory and invasive properties. These features allow the metastatic process to take place in the body. The luminal breast cancer subtype is characterized by the presence of luminal markers such as CD24 or MUC1. These two different breast cancer subtypes are compared to identify specific markers for claudin-low subtype to better understand pathways involved in metastatic progression. Such information is important as it would allow for therapeutics to be developed to stop metastatic progression in cancer patients.

The data of five cell lines representing either (A) Claudin-Low (condition) breast cancer subtype and (B) Luminal (control) breast cancer are investigated using RNA-sequence analysis to examine gene expression and investigated using the current invention for the goal of identifying specific pathways involved in metastatic progression. The RNA sequence data is uploaded to the system. The system identifies 1719 differentially expressed, mapped genes FIG. 6A, 601. The top gene in the report by the system is TGFB1, ranked by gene expression and connectivity. TGFB1 is known to be a regulator of EMT processes in cancer cells. The top ranked processes identified by the system is the migration of tumor cell lines; the top disease is carcinoma.

Example 2. Validation Study to Verify Diagnostic Markers for Lung Cancer by Quantitative Real-Time PCR (Qpcr)

Whether biomarker analysis in endobronchial epithelial lining fluid (ELF) collected by bronchoscopic microsampling may be useful for a definitive preoperative diagnosis of lung cancer is investigated.

The gene expression of 16 known genes in epithelial lining fluid samples close to nodule and from the contralateral site from patients with (A) Malignant or (B) Benign (noncancerous) diagnosis is compared using qPCR analysis. The QPCR data is then uploaded to the system and analyzed using the modules.

Figure 5C:
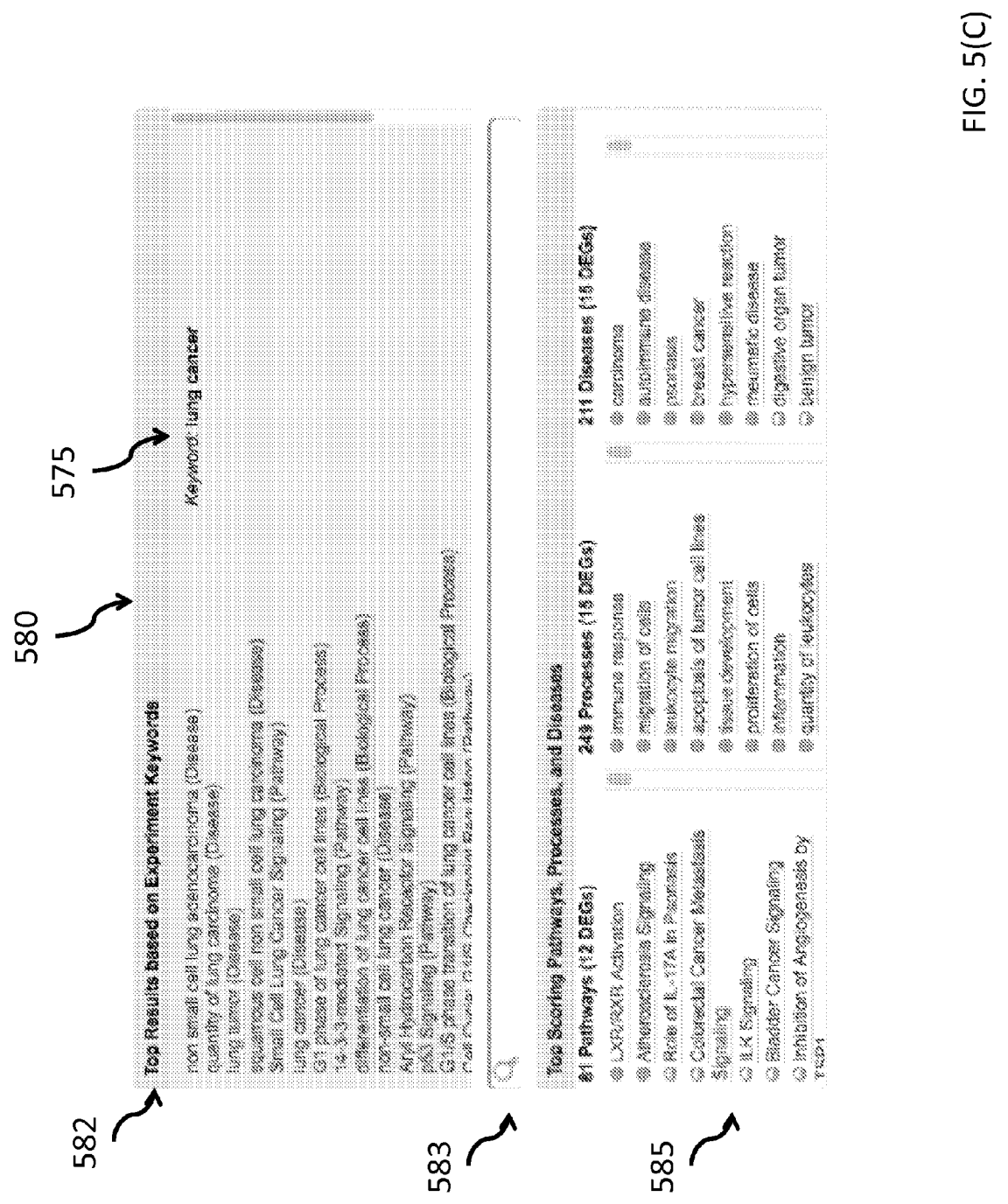

The report generated from system confirms that all 16 genes are differentially expressed between malignant and benign samples (FIG. 6(B)). The top gene identified by the report is MYC, a known cancer gene (FIG. 5A). The report confirms that the 16 genes from the endobronchial epithelial lining fluid are good indicators of the presence of lung cancer. The top disease identified by the system is carcinoma as detailed in FIG. 5(C), 585. The biological processes identified by the system are shown in FIG. 8(D), 810.

Example 3. Investigation of GRHL2 in Breast Cancer Cell Line

In light of the high degree of similarity between the epithelial-mesenchymal transitions (EMTs) occurring in wound healing processes and the cancer stem cell-like compartment of tumors, including TGF-β-dependence, the role of a Grainyhead gene (GRHL2) in oncogenic EMT using the breast cancer cell line MDA-MB-231 is investigated. GRHL2 is expressed in the breast cancer cell line MDA-MB-231. Functionally, GRHL2 suppresses TGF-β-induced, Twist-induced or spontaneous EMT, enhances anoikis-sensitivity, and suppresses mammosphere generation in mammary epithelial cells.

The system report shows 1565 of mapped genes differentially expressed in the data set, generates a report, and identifies cell movement as the top ranked biological process and tumorgenesis as the top disease.

What is claimed is:
1. A method comprising the steps of:
   (a) determining a set of experimental design criteria;
   (b) inputting the experimental design criteria into a system for prioritizing experimental results;
   (c) generating a biological data set using the experimental design criteria;
   (d) inputting the biological data set into the system for prioritizing experimental results;
   (e) querying by the system for prioritizing experimental results an ontological database for relationships based upon the experimental design criteria;
   (f) comparing by the system for prioritizing experimental results the relationships to the biological data set generated using the experimental design criteria; and
   (g) prioritizing by the system for prioritizing experimental results the biological data set based upon the comparison; wherein the system for prioritizing experimental results comprises a stand-alone computer, a multi-component computer, or a networked computer.
2. The method of claim 1, wherein the generating the biological data set comprises sequencing a nucleotide, gene expression determination by qualitative RT-PCR, gene chip hybridization, mass spectrometry data, antibody readout of gene expression products such abundance, phosphorylation status or activation state.

* * * * *